(12) United States Patent
Drasler et al.

(10) Patent No.: US 11,612,484 B2
(45) Date of Patent: Mar. 28, 2023

(54) TWO COMPONENT MITRAL VALVE DEVICE AND METHODS

(71) Applicants: William Joseph Drasler, Minnetonka, MN (US); William Joseph Drasler, II, Minnetonka, MN (US)

(72) Inventors: William Joseph Drasler, Minnetonka, MN (US); William Joseph Drasler, II, Minnetonka, MN (US)

( * ) Notice: Subject to any disclaimer, the term of this patent is extended or adjusted under 35 U.S.C. 154(b) by 306 days.

(21) Appl. No.: 17/037,810

(22) Filed: Sep. 30, 2020

(65) Prior Publication Data

US 2021/0022865 A1 Jan. 28, 2021

Related U.S. Application Data

(63) Continuation of application No. 16/211,115, filed on Dec. 5, 2018, now Pat. No. 10,813,759, which is a continuation of application No. 15/457,626, filed on Mar. 13, 2017, now Pat. No. 10,172,710.

(60) Provisional application No. 62/495,955, filed on Sep. 28, 2016, provisional application No. 62/493,780, filed on Jul. 15, 2016, provisional application No. 62/391,828, filed on May 10, 2016, provisional application No. 62/497,708, filed on Nov. 29, 2016.

(51) Int. Cl.
*A61F 2/24* (2006.01)

(52) U.S. Cl.
CPC .......... *A61F 2/2445* (2013.01); *A61F 2/2409* (2013.01); *A61F 2/2418* (2013.01); *A61F 2/2433* (2013.01); *A61F 2/2463* (2013.01); *A61F 2220/0016* (2013.01); *A61F 2220/0075* (2013.01); *A61F 2230/0052* (2013.01); *A61F 2230/0067* (2013.01); *A61F 2230/0093* (2013.01); *A61F 2250/006* (2013.01); *A61F 2250/0039* (2013.01); *A61F 2250/0069* (2013.01)

(58) Field of Classification Search
CPC ..... A61F 2/2412; A61F 2/2415; A61F 2/2442
See application file for complete search history.

(56) References Cited

U.S. PATENT DOCUMENTS

2016/0361159 A1* 12/2016 Huber ................. A61F 2/90

* cited by examiner

*Primary Examiner* — Jason-Dennis N Stewart

(57) ABSTRACT

A method for transcatheter delivery to a native heart valve needing replacement. A first component is attached to the native annulus upstream of the native leaflets maintaining native leaflet function, and is held to the native annulus by barbs that are activated by a torus balloon after the first component is fully expanded. The torus balloon can be implanted along with the support frame. A limiting cable restricts further expansion of the first component and holds a second component that contains the replacement leaflets.

18 Claims, 34 Drawing Sheets

Fig. 3C
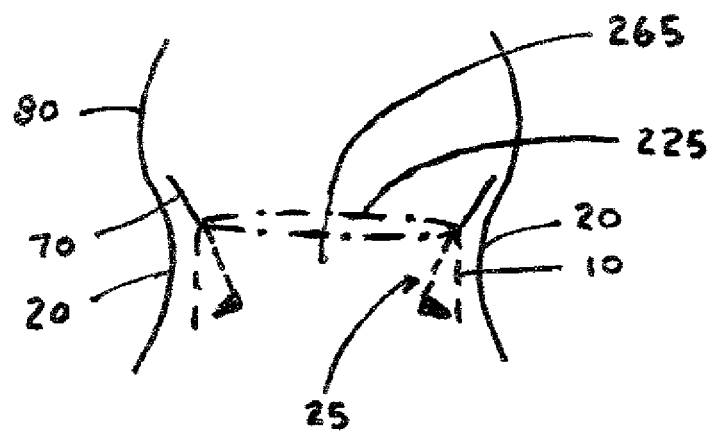
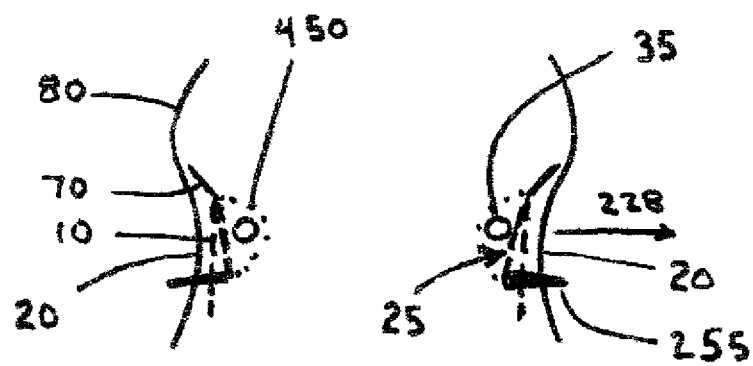
Fig. 3D

Fig. 9C
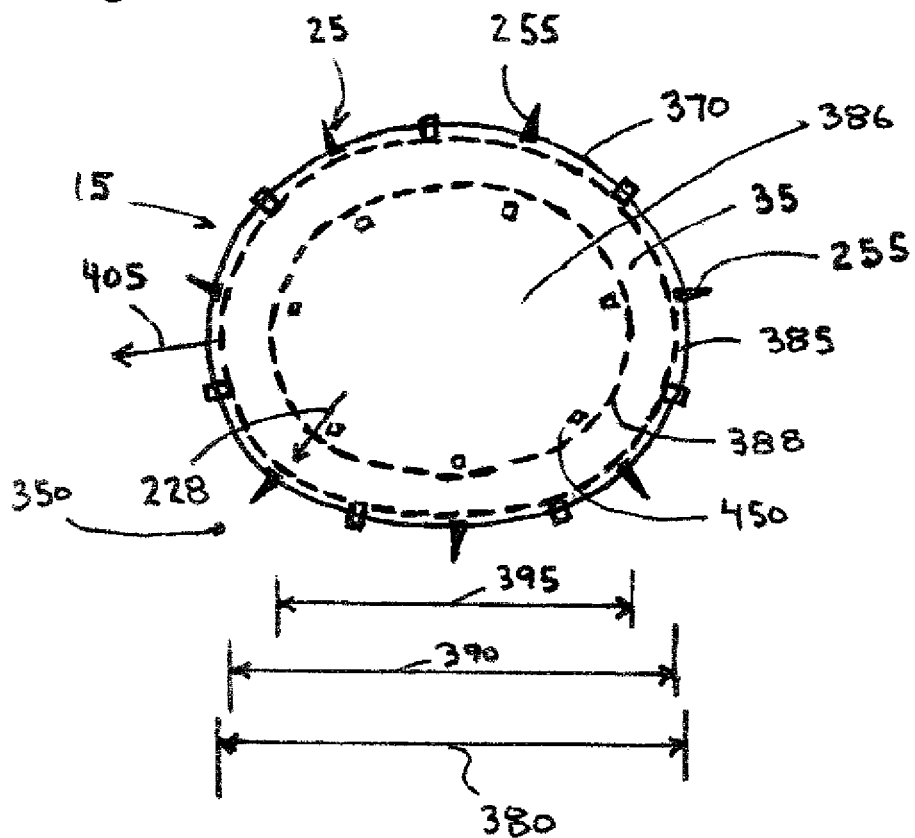
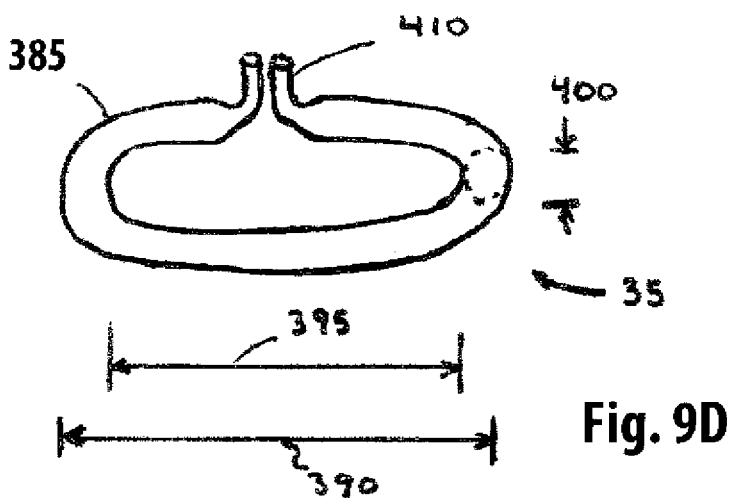
Fig. 9D

Fig. 10A
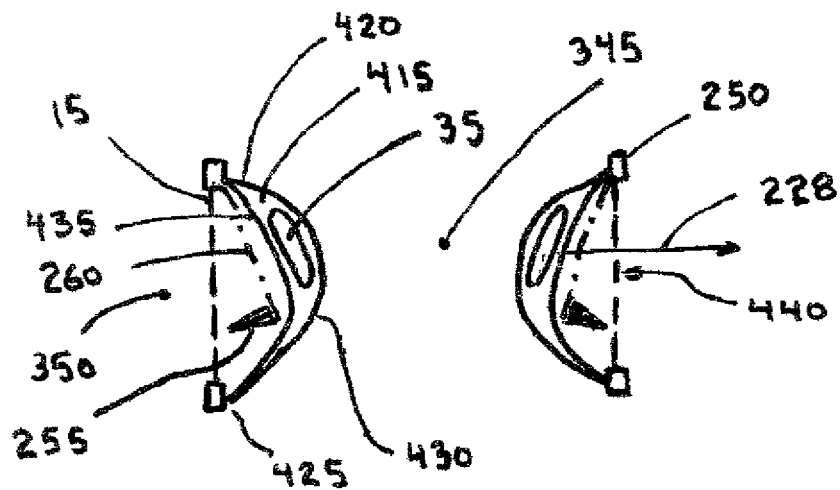
Fig. 10B
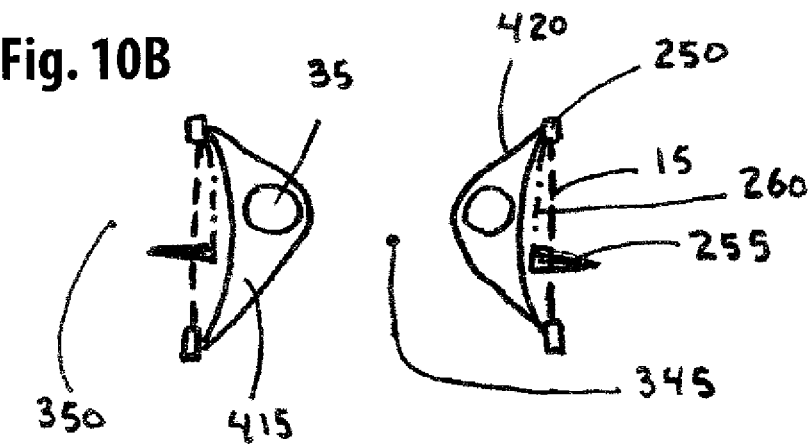
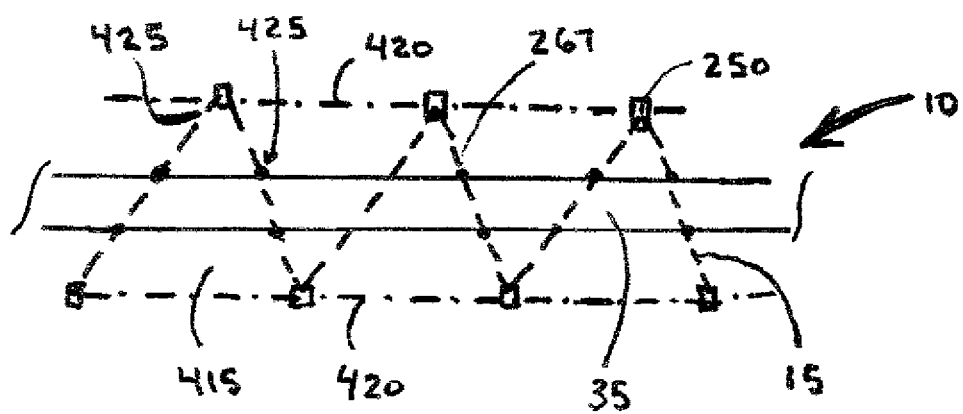
Fig. 10C

Fig. 12C
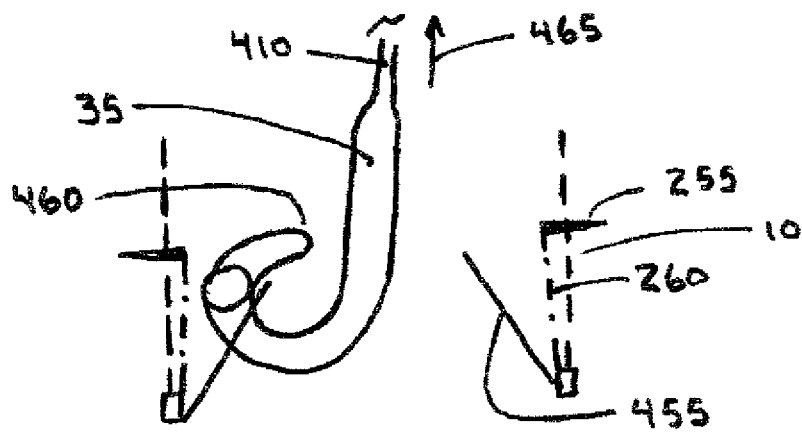
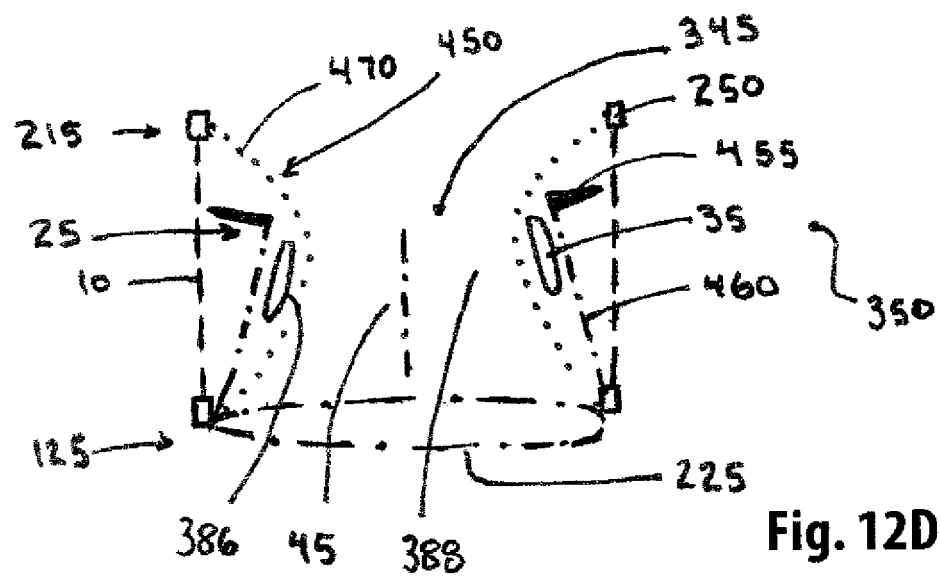
Fig. 12D

Fig. 18
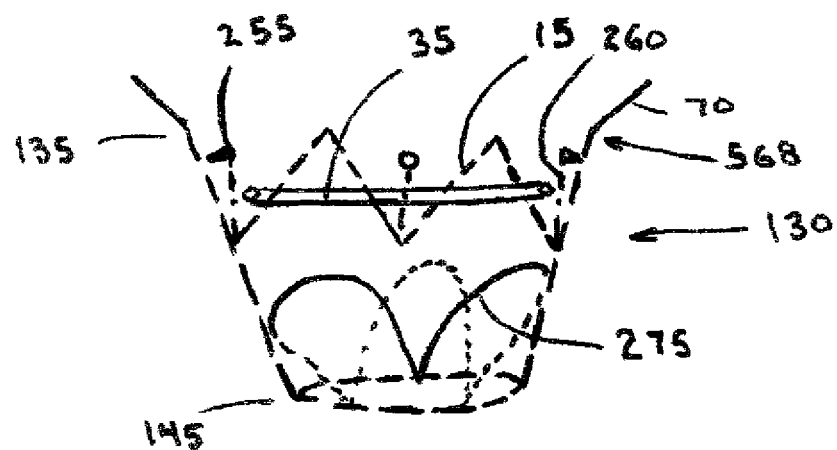
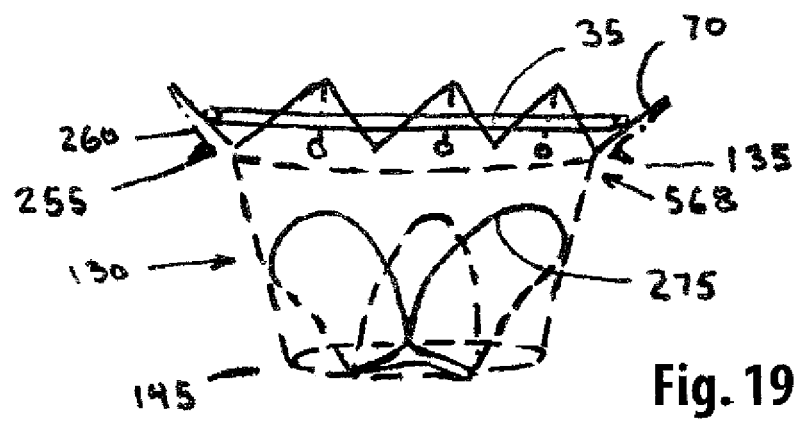
Fig. 19

Fig. 20A
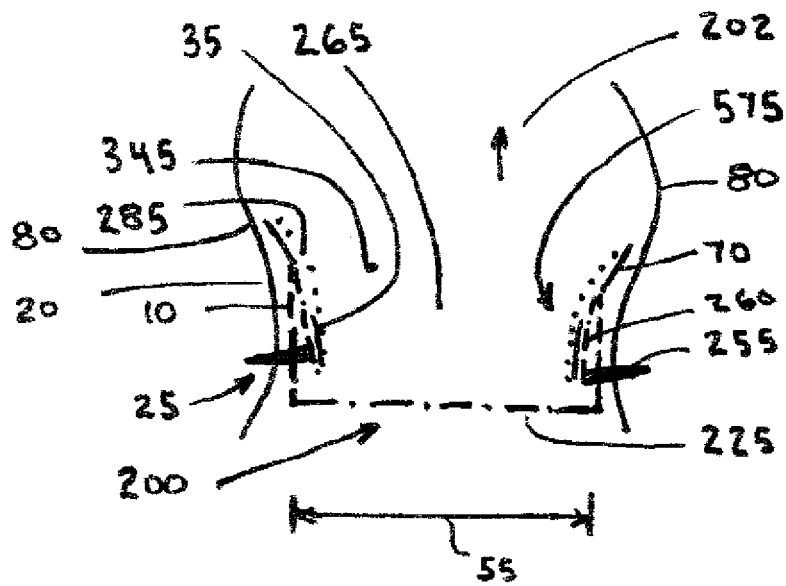
Fig. 20C
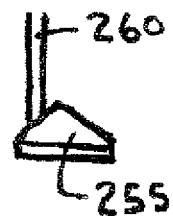
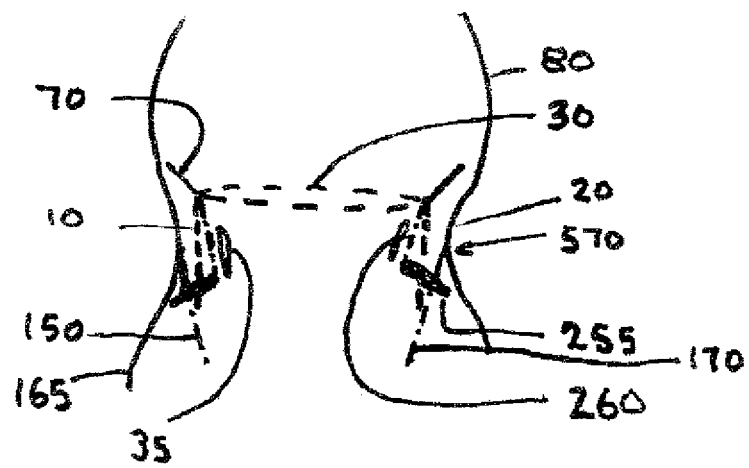
Fig. 20B

Fig. 24E
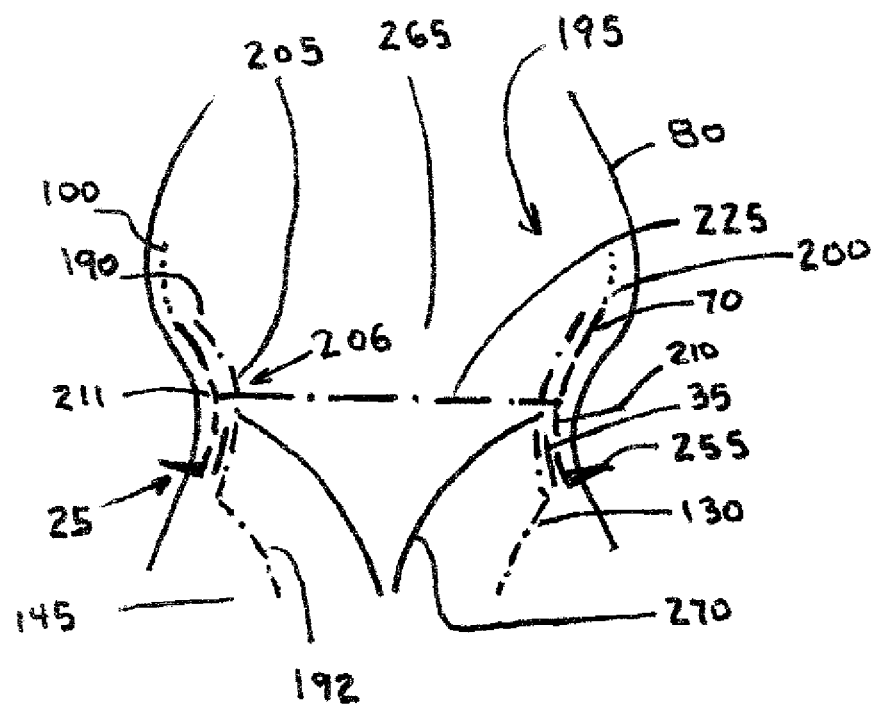
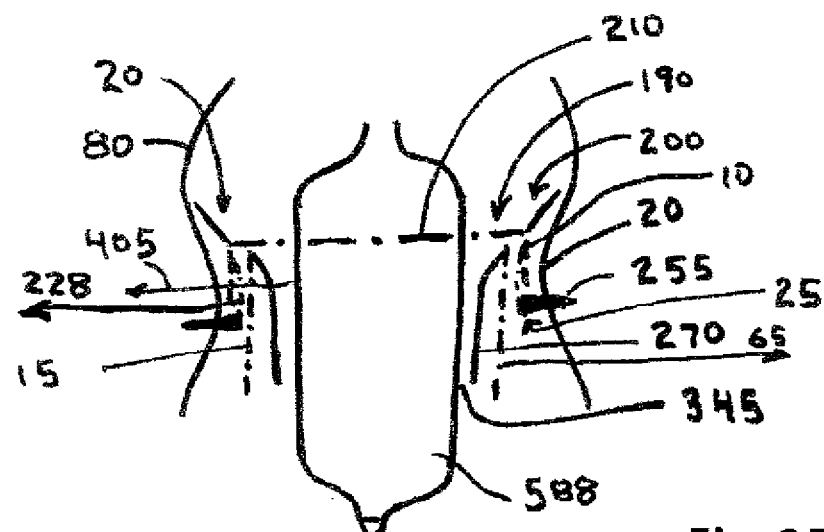
Fig. 25

TWO COMPONENT MITRAL VALVE DEVICE AND METHODS

CROSS REFERENCE TO RELATED APPLICATIONS

This patent application is a continuation of application Ser. No. 16/211,115 filed 5 Dec. 2018 entitled Two Component Mitral Valve by William J. Drasler and William J. Drasler II, the entire content of which is hereby incorporated herein by reference in its entirety, which is a continuation of application Ser. No. 15/457,626 filed 13 Mar. 2017 entitled Two Component Mitral Valve and naming William J. Drasler and William J. Drasler II as inventors, the entire content of which is hereby incorporated herein by reference in its entirety.

BACKGROUND OF THE INVENTION

Valves of the heart including the aortic valve and mitral valve can become hardened from atherosclerotic plaque and calcium and no longer function normally. Alternately these valve can prolapse and allow blood to pass through the valve in a retrograde manner that is opposite to the normal direction of flow through the valve. Such regurgitant flow can require repair or replacement of the valve. Surgical repair or replacement of such valve is often the gold standard at present for those patients able to withstand the rigors of surgery. An alternate and less invasive approach would be desirable via access to the valve from the femoral vasculature, vasculature of the arms, the apex of the heart, aortic access, or via other less invasive sites.

Transcatheter aortic valve replacement (TAVR) has evolved to become an accepted less invasive procedure for replacing diseased or incompetent aortic valves in high risk patients. Such less invasive surgical procedures are not as well developed for replacing abnormally functioning mitral valves.

Often the regurgitant mitral valve is a result of excessive expansion of the left ventricle (LV) leading to abnormal tension and angulation imposed on the mitral valve leaflet. The mitral valve leaflet is often unable to coapt properly with its neighboring leaflet and will therein allow retrograde blood flow to occur through the valve. The mitral valve annulus is more elastic, in part, than the aortic annulus and can expand in diameter reducing the ability of the mitral valve leaflets to coapt properly; one should not expand a stent into the mitral annulus to push it further outwards as is done with TAVR procedures onto the aortic valve annulus.

The mitral anatomy also provides that the anterior mitral leaflet not only helps close the mitral annulus during systole, but also provides one surface of the left ventricular outflow track (LVOT) during systolic pumping of blood out of the LV. It is therefore not acceptable to expand a stent indiscriminately outwards as is done in TAVR due to the potential for blockage of the LVOT by the anterior mitral valve leaflet.

The use of barbs or other fixation members to hold the TMVR device securely to the native mitral apparatus can create a set of potential clinical issues that are problematic to the patient. Expansion of barbs prior to full apposition of the TMVR stent against the mitral annulus, for example, can obviate the ability of the barbs to position themselves and the stent-valve frame uniformly around the perimeter of the mitral annulus. Furthermore, activation of barbs via a standard dilation balloon can block blood flow through the mitral annulus during balloon inflation causing the patient to temporarily go without oxygen supply to the brain with its ensuing consequences. Additionally, inflation of a standard balloon can cause the positioning of the stent-valve to become instantaneously displaced and hence inappropriately located across the mitral annulus due to blood pressure and blood flow generated by the LV.

The delivery profile of TMVR devices is generally greater than those for TAVR due to the larger diameter of the mitral annulus in comparison to the aortic annulus. This profile limitation has forced many of the TMVR devices to be delivered via the apex of the heart rather than through a more favorable transvascular and transseptal delivery approach. The apical approach is not well suited to patients that are older in age or are of higher risk. What is needed is a TMVR device that is of a lower profile such that it can be delivered via a transvascular and transseptal approach. The device should be easily positioned across the mitral annulus and secured to the native mitral apparatus without chance for device migration. The TMVR device should eliminate regions for blood stagnation that can lead to thromboemboli that could potentially result in stroke and should not restrict blood flow out of the LVOT.

SUMMARY

Embodiments of the present invention contain a stent that is expanded via a mechanical means such as a balloon; other embodiments are formed from a self-expanding material and are released via withdrawal of a sheath in a manner similar to that taken with current TAVR devices.

In one embodiment the device is a single member stent-valve that is able to be used for Transcatheter Mitral Valve Replacement (TMVR) has a SE stent frame with a cylindrically-shaped or a curved waist portion and an upper bulb that is attached to the waist. This waist portion makes direct contact with the mitral annulus and ensures a tight seal against the mitral annulus; the upper stent bulb extends into the left atrium (LA) and outwards against the wall of the into the LA to provide additional seal against the LA to mitral annulus junction and to heal into the tissues above the mitral annulus to ensure that the mitral annulus does not expand further over time. The waist of the SE stent frame can have a limiting cable attached around its perimeter to ensure that the waist cannot expand further beyond a prescribed perimeter upon release from an delivery sheath that can ensure that an outward force is not being continuously applied to the mitral annulus. The outward force exerted by the SE waist to reach its full perimeter and expand the mitral annulus outward to a round shape can also be increased beyond the forces normally applied by a standard SE stent frame due to the presence of a limiting cable.

In one embodiment a stent frame housing is attached to the waist of the stent frame and extends into the left ventricle (LV) to provide a housing for the replacement leaflets. The replacement leaflets are formed from a tissue material, a synthetic polymeric material, or a composite material which can include a metal such as Nitinol (NiTi); the replacement leaflets are formed from a material that can be implanted within the body for periods of years without degradation or causing an adverse reaction to the body. The housing of this invention can have a shape of a cone that has its top cut off forming a frustum; the top of the frustum extending on the downstream or outflow end of the housing that is closest to the apex of the heart. The smaller diameter of the outflow end provides two major advantages. First, the frustum-like shape does not push the native anterior leaflet of the mitral valve outwards into the LVOT which can impede blood flow out of the LV. Second, the frustum-shaped housing also allows the native mitral leaflets to be adequately exposed to blood flow across the native mitral leaflet surfaces (the inner flow surfaces that contact the blood flow from the LA to the LV and the outer surfaces that faces the myocardial wall) such that thrombosis is not generated and thrombo-emboli are not released with potential migration to the brain and resultant stroke.

The leaflets contained within the frustum-shaped housing can have a frustum-like shape. The replacement leaflets form a crown-like shaped attachment to the frustum-shaped housing; the nadirs of the crown-shaped attachment at the base of the leaflets forms a perimeter at the base of the housing that is significantly larger than the perimeter of the housing at the outflow end of the housing. The free edges of the replacement leaflets do not come into direct contact with the top of the frustum-shaped housing at the outflow end; the spacing between the free edges of the replacement leaflets from the housing allows blood flow to rinse the leaflets during diastole and prevent thrombosis from occurring.

A fabric or covering is attached to some or all of the SE stent portion of the housing to prevent regurgitant flow through the TMVR; the covering can extend throughout the entire stent structure, including the waist, upper bulb, and housing portions to ensure that retrograde blood leakage is not obtained. The covering can be formed from a fabric material such as a woven or knitted fabric or a polymeric sheet material; the material for the fabric can be nondistendable fabric such as PET or Nylon that resists expansion of the covering upon exposure to expansion forces. Alternately, the covering can be formed in some embodiments from an expandable material such as polyurethane or spandex that will allow expansion of the covering; the restraining forces from a limiting cable attached along a perimeter of the waist or housing can serve to limit excessive expansion of the housing beyond a specified diameter and is necessary to maintain replacement leaflet coaptation.

The replacement leaflets contained within and attached to the housing portion of the stent can form a bileaflet valve similar to that found in the venous system or native mitral valve of the body, or the replacement leaflets can form a trileaflet valve similar to that found in a native aortic valve. The material for the valve leaflets can be bovine, porcine, or other animal pericardium or other tissue, collagen, fibrin, or other valve material including polymeric or composite materials used or anticipated for use in replacement valves. Alternately, a synthetic valve material can be used including material such as polyurethane, ePTFE, NiTi, or composite materials used in implanted devices. Attachment of the leaflets to the housing portion of the stent follows a curved or crown-shaped path that is similar to that found in the attachment of aortic valve leaflets or venous valve leaflets to their respective conduit. Polymeric or metal fibers or members can be contained within the leaflet structure or attached to the leaflet structure to provide both structural strength and provide flexing characteristics to the leaflets and also assist as members that can be directly attached to the stent frame. The crown-shaped attachment of the leaflets of the present invention can have a frustum-like shape in the respect that the base of the leaflets follows a perimeter that is larger than the perimeter of the free edge of the leaflets by at least 30%. Bileaflet replacement mitral valve leaflets are also anticipated for use with the present invention, a bileaflet valve can be oriented such that the major axis of the native mitral annulus is oriented with the commissures of the bileaflet valve to allow for improved coaptation of the leaflets over a greater range of ovality of the mitral annulus and result in less regurgitation and improved durability for the replacement leaflets.

The waist, upper bulb, and housing portion of the stent frame can be formed from any stent geometry such as open-cell or closed-cell stent wall construction. An additional expansion limitation element- such as a limiting cable may be placed into the stent geometric structure that limits the amount of radial expansion that the waist portion or the housing can attain. The upper bulb portion of the frame on the LA side of the waist is able to expand freely and extend in diameter further than the waist.

Balloon expandable (BE) or self-expanding (SE) barbs are located along the perimeter of the waist of embodiments of the present invention to provide fixation of the stent frame to the mitral annulus. In one embodiment, the barbs are formed from a BE material such as stainless steel, for example. The BE barbs remain in an inactive configuration until the waist is expanded into contact with the mitral annulus. A post-dilation step is then performed using an expandable or dilation balloon to push against the BE barbs and activate them into a configuration that engages the tip of the barb with the tissues of the mitral annulus. The barbs, when activated, provide stability to the stent frame against migration toward the LA due to blood pressure and flow generated by the LV.

A dilation balloon used for delivery or expansion of specific embodiments of the present invention can be formed from a shape having a diameter approximately equal to that of the mitral annulus in the waist portion and an alternate diameter that matches the shape and diameter of the stent frame and tissue structure in another portion. The balloon can have a torus or doughnut shape to allow blood flow across the annulus with the balloon inflated. The delivery system for some specific embodiments may include such a balloon to dilate various components of the present invention.

In another embodiment for fixation of the stent frame to the annulus the barbs are formed from a SE material; the SE barbs (formed from NiTi, for example) are held by a control fiber in an inactive position until the waist has been positioned against the annulus and has been fully expanded to its final diameter. The barbs can be released or activated by applying tension to the control fiber once the waist of the stent frame has been determined to be positioned accurately adjacent the annulus.

In yet another embodiment the valve of the present invention consists of a dual member stent-valve formed from two components that are delivered separately. The first component or support member contains a waist that forms a portion of the stent frame that is firmly attached to the mitral annulus (via barbs) and forms an outer ring structure into which a smaller diameter stent-valve can be placed; the outer ring structure can be formed by a limiting cable that is placed along the perimeter of the stent frame. The first component provides a fixed perimeter that holds a second component stent-valve via a frictional fit or via geometric locking of the first and second components. The first component forms an adapter that allows a second component (containing the replacement leaflets) to be implanted within its open central lumen as a second step. The embodiment for the first component that is comprised of a waist or waist frame is intended to allow complete unobstructed function of the native valve leaflets (by locating the stent frame waist across the mitral annulus and above the native mitral leaflets, for example) until the second component is inserted into and attached to the first component. Alternately, an upper bulb and/or a housing can be attached to the waist to form the first component. The stent frame is delivered to the location requiring a replacement valve contained in a small diameter non-deployed configuration within a sheath. The SE waist is released from the sheath and allowed to expand adjacent the mitral annulus; the stent frame has an upper bulb located above the waist in the LA to assist with positioning the stent frame waist across the annulus. The upper bulb has a larger diameter than the waist to prevent migration of the valve toward the LV and to provide a seal between the stent frame and the wall of the LA and mitral annulus. The equilibrium waist diameter is sized to be slightly larger (approximately 2 mm larger) than the effective diameter of the annulus to ensure that it makes direct contact along the entire perimeter of the mitral annulus and prevents leakage between the stent frame and the mitral annulus.

The second component of this embodiment is a stent-valve; the stent-valve having an expandable stent frame and replacement leaflets attached to the stent frame. In one embodiment the stent-valve has a frustum-like shape frame body that houses the replacement leaflets and having a smaller diameter at the outflow end of the frustum-shaped body by 30% (range 25-35%) than the diameter of the mitral valve annulus or the diameter of the inflow end of its frustum-shaped body. The stent-valve can be a modified TAVR device or a stent-valve with a frustum-like or hyperboloid-like shape for its frame. A TAVR device can be modified to form a frustum-like second component that is inserted and placed into the housing of the first component of the present invention. For example, the skirt or covering of a stent-valve device could be removed such that the covering of the first component housing serves to provide the function of preventing leakage of blood past the valve leaflets of the stent-valve device. The second component is delivered after the first component has been successfully positioned and attached across the mitral annulus.

In another embodiment the second component can be a cylindrically shaped stent-valve similar to some stent-valves used for TAVR implantation. The cylindrically shaped stent-valve can be held into contact with the first component via friction, geometric, or locking members to the waist of the first component. In one embodiment the SE waist of the second component is positioned adjacent to the waist of the first component. Release of the frustum-shaped stent-valve body of the second component is accomplished by removal of an external sheath that was holding the SE stent-valve and its contained replacement leaflets in a collapsed configuration. In another embodiment the second component could be formed instead from a BE stent body and delivered to the first component housing via mounting onto a dilation balloon that is shaped to fit within the first component housing.

The diameter of a mitral valve annulus is typically 35 mm and ranges from 28-40 mm in most patients; some patients could have an enlarged mitral valve annulus that is larger than 48 mm; some mitral annulus can be as small as 25 mm. The stent frame of the first component of the present embodiment has a waist that is located adjacent the mitral annulus and is approximately 35 mm for an average diameter to match the diameter of the mitral annulus. The aortic valve annulus is significantly smaller than the mitral valve annulus with an average diameter of approximately 24 mm and ranging from 19-29 mm. The use of a limiting cable located within a curved waist of the first component; the curved waist having a convex shape that extends into the open lumen of the first component provides a locking member for frictional or geometrical locking of the first component with the second component; the second component having a small 25 mm stent frame diameter that is similar to the diameter of a TAVR device The activation of BE fixation elements such as BE barbs to hold the stent frame from migration can be accomplished using a torus-shaped balloon (i.e., torus balloon) rather than a standard large diameter cylindrically-shaped dilation balloon. The torus balloon has a central opening similar to the opening of a doughnut that allows blood flow to cross the balloon without impeding flow through the mitral annulus. The central opening of the torus balloon allows the BE barbs to be activated while blood flow through the mitral annulus is maintained without blockage as would be imposed by a cylindrical or conically shaped balloon without a central opening.

The torus balloon of one embodiment of the present invention is attached to the waist or other region of the stent frame and saline is used to inflate the torus balloon after the waist portion of the stent frame is positioned properly adjacent to the mitral annulus. The inflated torus balloon pushes the fixation elements or fixation barbs outward into penetration within the mitral annulus. Prior to inflation of the balloon, the stent frame can be withdrawn into the delivery tube and repositioned across the mitral annulus, if necessary. Upon activation of the BE barbs, the inflation fluid delivery tube is detached from the torus balloon and the inflation tube is removed from the device. The saline inflation fluid is allowed to leak out of the torus balloon allowing the torus balloon to return to a flattened deflated configuration and the torus balloon can be implanted along with the stent frame.

Summary of Removable Torus Balloon

In one embodiment the torus balloon is intended to be attached to the stent frame and is implanted along with the stent frame into the tissues of the heart. In another embodiment, the torus balloon is removable from the stent frame such that the torus balloon can first be inflated to activate the BE barbs and then be removed from the tissues of the body thereby leaving the other portions of the stent valve implanted adjacent the mitral annulus of the heart.

In another embodiment of the mitral valve device SE fixation elements are held in an inactive configuration toward the inside or luminal side of the stent frame. A feature that is formed onto the barb is designed to interface with a control fiber that holds the SE barb in an inactive configuration. Upon release of the control fiber via application of a tension force in the control fiber, the SE barb springs back to its equilibrium configuration with the barb extending outwards to the outside of the stent frame and into the mitral annulus. The bards extend into the mitral annulus along a perimeter of the mitral annulus. Their depth of penetration into the mitral annulus is less than the depth that would allow penetration into the circumflex artery that could otherwise cause negative sequellae.

In another embodiment the torus balloon can be formed with a segmented configuration formed from a series of larger diameter spherical segments separated by a series of smaller diameter cylindrical segments. The larger diameter spherical segments are placed adjacent to the inside of the barb struts to push the barbs outwards upon inflation of the segmented torus balloon. The smaller diameter cylindrical segments connect each spherical segment to each other and also the balloon port to provide an inflation lumen through which each of the spherical segments can be inflated. The smaller diameter cylindrical segments maintain a lower profile for the torus balloon in both its delivery configuration as well as during inflation and as the balloon is implanted.

In one embodiment positioning for the cylindrical segments on the outside surface of the stent frame provides the stent-valve with an advantage by not pushing the stent frame further away from the mitral annulus as the torus balloon is inflated. In another embodiment with the cylindrical segments positioned on the inside of the stent frame a greater area for blood flow through the central lumen of the torus balloon will be provided.

BRIEF DESCRIPTION OF THE DRAWINGS

FIG. 3C is a perspective view of the waist and upper bulb of a frame having barbs attached and found in an inactive configuration with barb tips on the inside of the frame.

FIG. 3D is a perspective view of the waist and upper bulb of a frame having barbs attached and found in an active configuration with barb tips on the outside of the frame.

FIG. 9C is a top plan view of the torus balloon in an inflated configuration showing the barb tips extending to the outside of the frame perimeter.

FIG. 9D is a perspective view of the torus balloon showing the inner and outer diameters and showing the balloon ports for inflation.

FIG. 10A is a sectional plan view through the waist showing a torus balloon in a deflated configuration located adjacent to the barb struts and contained within a pocket of a balloon holder that is attached to the frame.

FIG. 10B is a sectional plan view through the waist showing a torus balloon in an inflated configuration located adjacent to the barb struts and the barb tips being activated to extend outside of the frame.

FIG. 10C is a plan view of a torus balloon attached to stent struts of the frame waist.

FIG. 12C is a perspective view of the torus balloon being removed from its releasable attachment to the frame following inflation of the torus balloon, activation of the barb tips, and deflation of the torus balloon.

FIG. 12D is a sectional view of the frame waist showing a torus balloon in contact with a barb strut; the torus balloon is supported opposite to the barb strut by a backing fiber that is attached to the frame.

FIG. 18 is a perspective view of a single member stent valve having a torus balloon in a deflated configuration along the perimeter of the frame waist and located adjacent to the barb struts.

FIG. 19 is a perspective view of a single member stent valve having a torus balloon located along the perimeter of the upper bulb and located adjacent to the barb struts.

FIG. 20A is a plan view of a first component or support frame located adjacent the native valve annulus having the barbs activated by a torus balloon and extending into the annulus; a limiting cable limits further expansion of the frame.

FIG. 20B is a plan view of a first component or support frame located adjacent the native valve annulus having the barbs activated by a torus balloon and extending into the base of the native valve leaflets.

FIG. 20C is a perspective view of a barb tip having a flattened shape.

FIG. 24E is a sectional view of a dual member stent valve having a first component or support frame located adjacent to the annulus and having barb tips activated by a torus balloon; the support frame has a concave waist region; the valve frame containing replacement leaflets form the second component and is positioned on the inside of the support frame and has a concave waist that locks with the concave waist of the support frame.

FIG. 25 is a sectional view of a balloon expandable second component placed within the open central lumen of a first component or support frame; a cylindrical dilation balloon expands the second component into contact with the support frame.

DETAILED DESCRIPTION

Figure 1A:
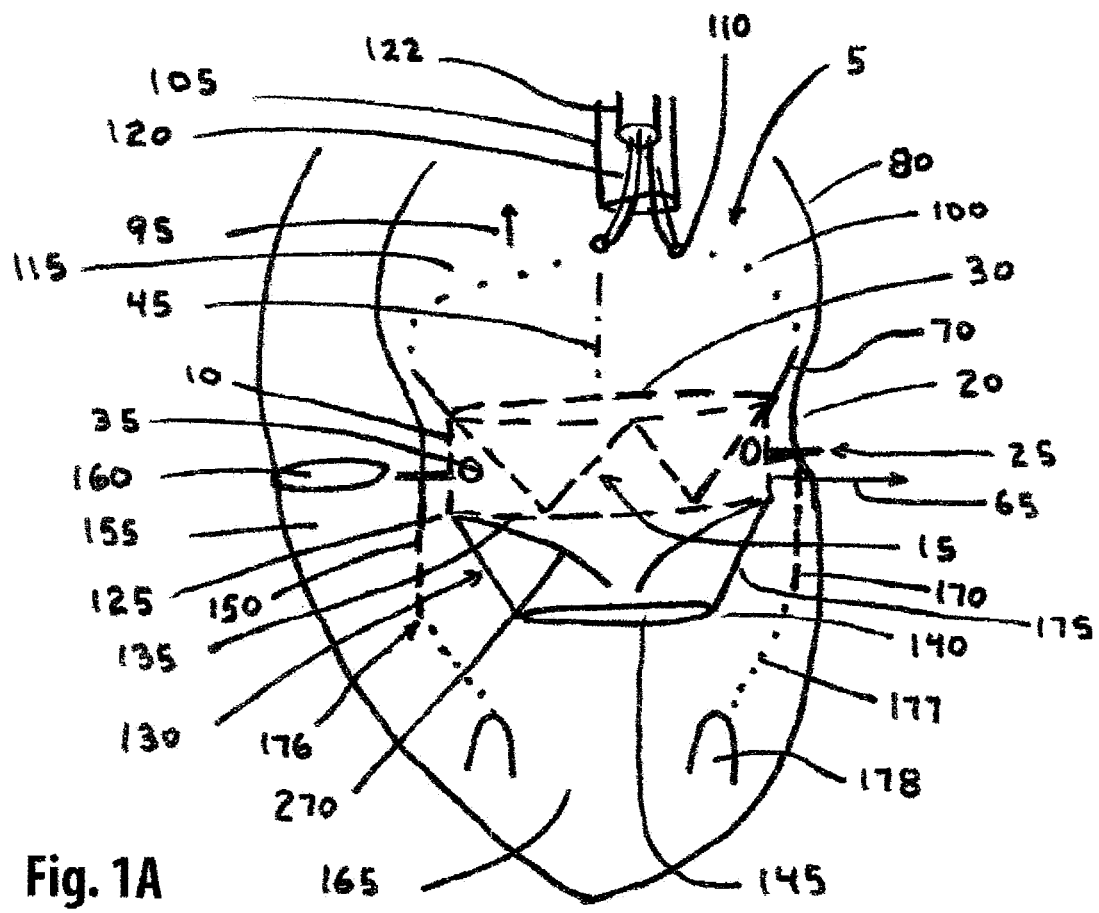
FIG. 1A is a perspective view of a single member heart valve in an expanded configuration positioned across the native mitral valve annulus.

One embodiment of the present invention comprises a single member stent-valve that is intended as a transcatheter replacement valve for a valve of the heart; the single member stent-valve (5) is intended to be delivered within the lumen of the native heart valve and expanded outwards forming a functioning valve device having replacement leaflets. The valve device will be described in an application for its use as a transcatheter mitral valve replacement (TMVR) although it is understood that the invention can be applied to other valves found within the heart. The invention further comprises a dual member stent valve comprised of two components, a first component or support member and a second component or valve member. The first component is delivered across the annulus of the heart and affixed to the annulus or other native tissues of the heart; the first component does not interfere with function of native valve leaflets such that the mitral valve is fully functional while awaiting the delivery and implant of a second component. The first component does not itself contain any replacement leaflets, and has an open lumen that allows unimpeded blood flow in both the upstream and downstream direction such that it can be positioned accurately across the mitral annulus without hemodynamic forces imposed on the first component. The second component or valve member of the dual member stent-valve is delivered subsequent to the first component and is placed within the open central lumen of the expanded first component; the second component contains the replacement leaflets that control blood flow in an antegrade or downstream direction from the left atrium (LA) to the left ventricle (LV). In describing various embodiments of the invention, it is understood that the single member stent-valve can have a fixation elements or barbs that function to hold or attach the frame of the single member stent-valve against the annulus tissues of the native heart valve to prevent migration of the frame; the same fixation elements can be found in the first component of a dual member stent-valve. Additionally, it is understood that the replacement valve leaflets found in the single member stent-valve are attached to the stent frame to direct blood flow in a downstream direction; the leaflets can be attached to the stent frame of the second component of the dual member stent-valve in the same manner as that found in the single member stent-valve.

The first component or support member of the dual member stent-valve provides, in itself an invention that functions as an adapter that can be implanted within the tissues of a native heart valve. Following implantation of the first component or adapter, a second device such as a stent-valve already available on the market can be implanted into the open central lumen of the first component. The second component can be, for example, a balloon expandable (BE) stent-valve or a self-expanding (SE) stent-valve used for transcatheter aortic valve replacement (TAVR) or other similarly sized stent valve device application. Alternately, the second component can comprise one of the embodiments of the second component that are presented in the present application. The reference numerals and reference names from each embodiment of this specification can be applied to other embodiments bearing the same reference numerals or reference names found in this specification.

One embodiment for the frame of the single member stent-valve (5) of the present invention is shown in FIGS. 1A-1D; the waist (10) of the single member stent-valve (5) frame (15) can be implanted adjacent to the annulus (20) of the native mitral valve as shown in FIG. 1A. The waist (10) of the single member stent-valve (5) can have barbs (25) located along the waist perimeter (30) as shown in FIG. 1A and further described in other embodiments of the invention; the barbs (25) can be activated by dilation of a torus balloon (35). The single member stent-valve (5) frame (15) is formed from an elastically deformable material such as Nitinol, Elgiloy, or other elastic, metal, plastic, or composite material. The wall structure of the portions of the frame (15) can be an open cell zig zag structure, a closed cell structure, a combination of open and closed cell or any other wall structure geometry that has been used or proposed for use in stents or stent-valves for vascular therapy.

The frame (15) is comprised of a cylindrical stent or a curved stent that forms the waist (10) of the present embodiment; the waist (10) is located adjacent to the valve annulus (20) (20) such as the mitral valve annulus (20). The waist (10) can have a non-cylindrical or curved shape that forms a curved waist (40) along its perimeter that is in contact with the native valve annulus (20) as shown in FIG. 1D and extends with a concave region (42) radially inward toward the central axis (45) of the frame. For the curved waist (40) the waist central diameter (50) has a smaller diameter than either the waist inlet diameter (55) or the waist outlet diameter (60). The waist central diameter (50) is 5 mm smaller (range 2-10 mm smaller) than the waist inlet diameter (55) or waist outlet diameter (60). The waist (10) is formed with a stored energy that exerts a frame outward force (65) onto an average sized annulus (20) of 35 mm diameter (range 25-48 mm) that is equivalent to the force provided by a 5 atm balloon (range 4-7 atm) of the same diameter. The large outward force of the waist (10) pushes the waist (10) into the mitral annulus (20) and forms a seal between the waist (10) and the mitral annulus (20). The waist (10) is attached to or contiguous with the upper bulb (70) which extends outwards from its attachment to the waist; the upper bulb (70) extending into the LA (80) with an upper bulb inlet diameter (75) that is larger than the waist inlet diameter (55). The upper bulb (70) extends outwards with an upper bulb angle (85) that can be at a 90 degree angle with respect to the waist (10) axial direction (90) or at a 45 degree angle or at an intermediate upper bulb angle. The upper bulb (70) serves to provide an improved seal between the upper bulb (70) and the annulus (20) and wall of the LA (80) as the upper bulb (70) undergoes healing with the mitral annulus (20) and surrounding tissues will serve to hold the mitral annulus (20) from further dilation; also, the upper bulb (70) serves to locate the waist (10) such that it is positioned adjacent to the annulus (20). Attached to or contiguous with the upper bulb (70) and extending upstream (95) into the left atrium (LA) are recapture struts (100); these struts are somewhat weaker in outward force than the waist outward force and have a larger overall equilibrium diameter and shape that matches the larger and curved or rounded surface found in the left atrium (LA). The recapture struts (100) allow the waist (10) and frame (15) of the present invention to be released from a delivery sheath (105) and placed into contact with the mitral annulus (20) and recaptured back into the delivery sheath (105) if the position of the waist (10) with respect to the mitral valve annulus (20) is not in position along the length of the axial direction (90) of the frame. The recapture struts (100) can be retained within a delivery sheath (105), for example, while the stent waist (10) has been released into contact with the mitral annulus (20). The frame (15) can be repositioned, if necessary, a second time across the mitral annulus (20). A holding feature (110) located at the proximal end (115) of the frame (15) allows the recapture struts (100) to be held by one or more control fibers (120) that extends through the delivery sheath (105) to a location outside of the body. A pusher member (122) is used to push the stent valve frame (15) out of the delivery sheath (105).

Attached to or contiguous with the distal or waist outlet end (125) (toward the distal end of the waist) is the housing (130). The housing (130) has the shape of a conical surface having its tip cut off at its top forming a frustum and provides a housing in one embodiment for replacement leaflets (270) which will serve to direct antegrade blood flow downstream from the LA to the LV and restrict retrograde blood flow from the LV to the LA. The larger housing base (135) of the frustum is attached to the waist, and the housing top (140) of the frustum-shaped housing (130) is located at the housing outlet end (145). Alternately, the housing (130) can have the shape of a one-sheeted hyperboloid of revolution that has been truncated as shown in FIG. 1C; the base of the hyperboloid is located adjacent to and attached to the waist (10) and the truncated portion that forms the top of the hyperboloid is located at the outlet end or outflow end of the housing (130). Both the frustum and the truncated hyperboloid are shapes that get continuously larger in diameter as they extend along their axial direction (90) from the housing top (140) to the housing base (135) of the frustum-shaped housing (130); the housing (130) for this embodiment does not contain a cylindrical region.

Figure 1B:
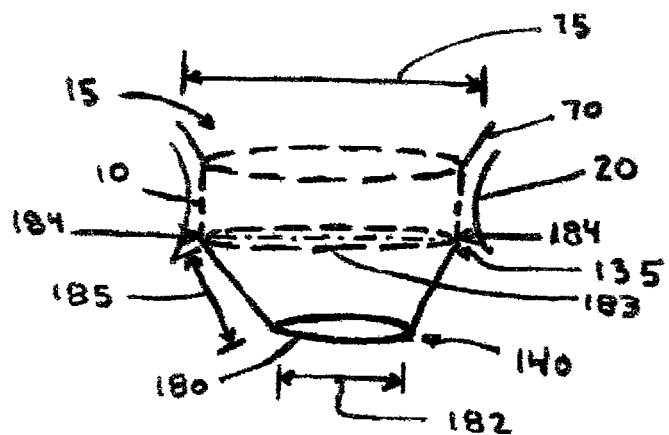
FIG. 1B is a perspective view of the frame of a single member valve with a frustum-shaped housing.
Figure 1C:
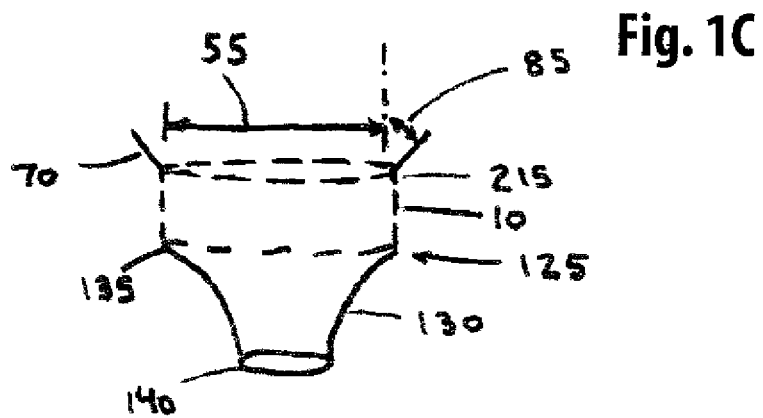
FIG. 1C is a perspective view of a frame having a housing with a shape of a hyperboloid of revolution.
Figure 1D:
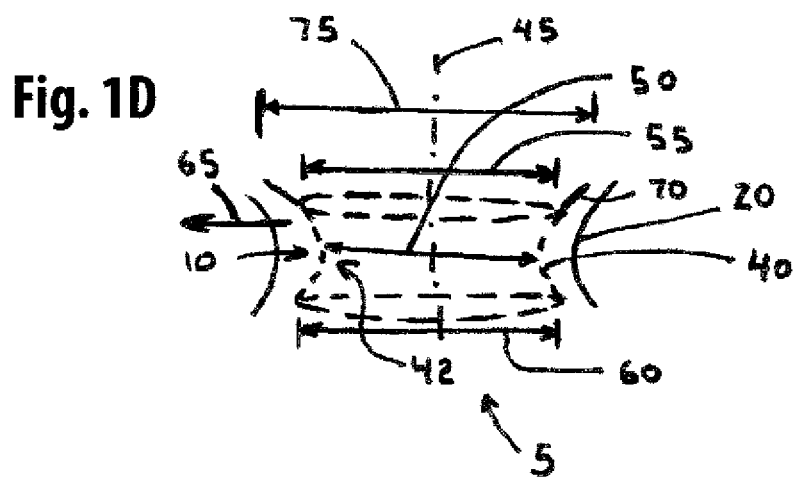
FIG. 1D is a perspective view of a frame having a curved or concave waist.

With the frame (15) implanted across the mitral annulus (20) as shown in FIGS. 1A and 1B the frustum-like shaped housing (130) (including the hyperbolic-shaped housing (130)) does not impinge upon the native anterior mitral leaflet (150); the left ventricular outflow tract (LVOT) (155) is not restricted from flow of blood out of the aortic valve (160) due to systolic contractions of the left ventricle, LV (165). As shown in FIG. 1B, the native anterior mitral leaflet and native posterior mitral leaflet (170) are able to approximate the housing outer surface (175) and prevent the formation of a low blood flow region that would be susceptible for formation of thrombus or thromboemboli that could lead to the formation of a stroke. The native free edges (176) of the native anterior mitral leaflet (150) and native posterior mitral leaflet (170) are attached via cordae tendineae (177) to papillary muscles (178) to prevent leaflet eversion during the cardiac systolic cycle. The housing base (135) of the frustum-like housing (130) is expanded outward to a perimeter that is equal to the perimeter of the mitral annulus (20); the effective diameter of the mitral annulus (20) (i.e., diameter of a circle have a specified perimeter) is an average of 35 mm (range of 25-48 mm); the housing top (140) of the frustum-like housing (130) has a housing top perimeter (180) and housing top diameter (182) that is 30% smaller (range 25-35% smaller) than the housing base perimeter (183) and housing base diameter (184) of the housing base (135) in its expanded configuration; the diameter of the top of the frustum is 25 mm (range 18-30 mm). The housing length (185) of the frustum-like housing (130) from the housing top (140) to the housing base (135) is 20 mm (range 10-30 mm).

Figure 1E:
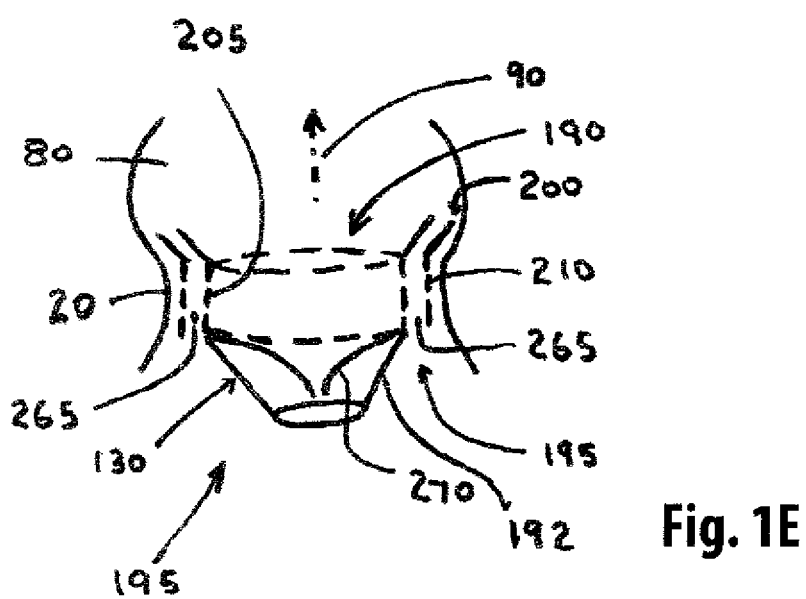
FIG. 1E is a perspective view of a dual component stent valve having a first component or support frame located against the annulus and a second component or valve frame positioned within the first component.

The stent-valve frame (15) as described in FIGS. 1A-1D can also be used as an embodiment for a second component (190) of a dual member stent valve (195) as shown in FIG. 1E. The second component (190) can have a valve frame (192) similar to the stent frame (15) structure as described for the single component stent-valve; the second component (190) is delivered into the open central lumen (265) of the first component or support frame (200). The second component waist (205) would, however, be delivered adjacent the first component waist (210) as shown in FIG. 1E; the first component waist (210) would be located adjacent and in contact with the native valve annulus (20). Also, the second component (190) may not contain the barbs (25) as described for the single component stent-valve; the ) would contain barbs (25) for fixation of the dual member stent-valve as described in other embodiments of this patent application.

Figure 2A:
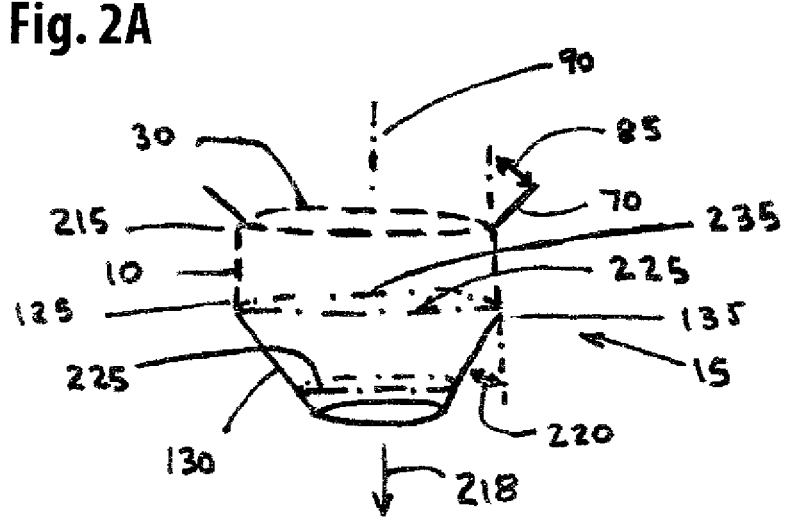
FIG. 2A is a perspective view of frame for a single member heart valve or a frame for a first component having two limiting cables located along a perimeter of the waist and the frustum housing.
Figure 2B:
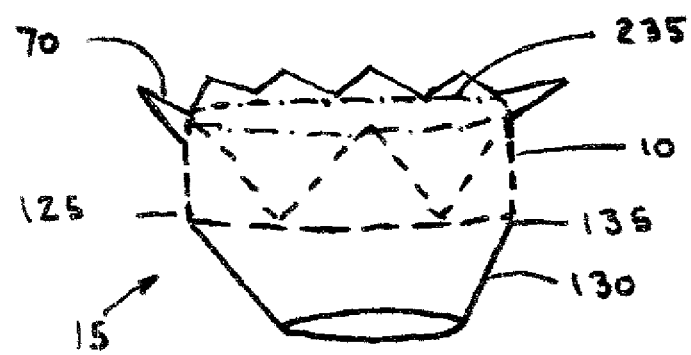
FIG. 2B is a perspective view of the frame showing the upper bulb in a perspective view.

FIGS. 2A and 2B show a side and perspective view of waist, upper bulb (70) and housing (130) of the frame (15) comprising the single member stent-valve (5) or the second component (190) of the dual member stent valve (195) of the present invention; replacement leaflets would be attached to the frame as described in other embodiments. The upper bulb (70) extends from the waist inlet end (215) with a bulb angle (85) of 45 degrees off of the axial direction (90) (range 20-90 degrees). The housing base (135) is attached to the waist outlet end (125); the housing (130) extends in a distal direction (218) toward the housing top (140) with a housing angle (220) (measured with respect to the axial direction (90)) of 11 degrees for a frustum (range 6 to 22 degrees); the housing angle (220) is 30 degrees (range 10-45 degrees) for a hyperboloid-shaped housing (130). A limiting cable (225) can be attached to the stent frame (15) or can be contiguous with the stent frame (15) along the waist perimeter (30) to limit the amount of radial expansion that the waist (10) is allowed to extend; the limiting cable (225) can also be attached along a perimeter of the housing (130). The cable can be formed from multifilament materials such as stainless steel, polyethylene terephthalate, Nitinol, and other polymer or metal materials, alloys, or composites. The cable is very soft in its ability to bend due to the multifilament strands of very small diameter filaments, typically having a filament diameter of 10 microns (range 5 microns to 100 microns). The cable is able to be easily folded back upon itself by application of a bending force equal to 50 grams (in earth gravitation). The limiting cable perimeter (235) is set to be 3 mm larger (range zero to 9 mm larger) than the perimeter of the annulus (20) such that the waist (10) of the stent with it large outward force is able to make direct contact around the perimeter of the annulus (20) without influence of the cable constraint; the cable prevents any further force to be exerted against the annulus (20) once the cable has reached its full perimeter. For a 35 mm annulus (20) effective diameter, for example, a 35-37 mm effective diameter of the cable would be used having a cable perimeter that is zero to 6 mm larger than the perimeter of the annulus (20) and a cable effective diameter (i.e., diameter of a circle with the perimeter of the cable) that is zero to 2 mm larger than the effective diameter of the annulus (20). The housing (130) gets continuously smaller as it extends in the axial direction (90) from the base to the top of the housing (130).

Figure 3A:
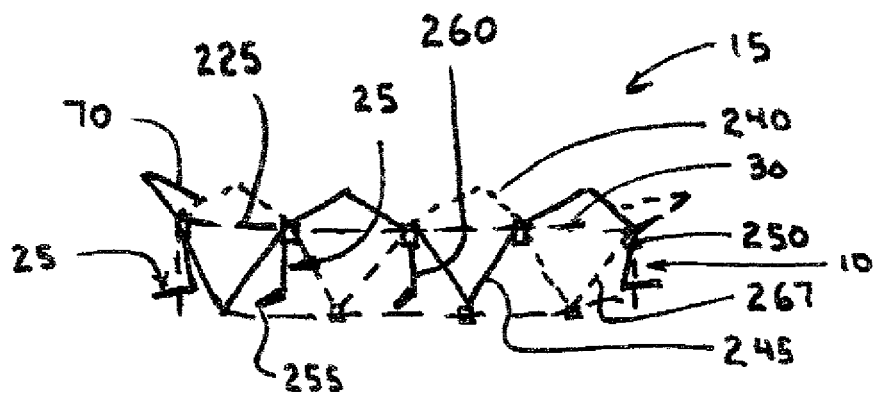
FIG. 3A is a plan view of the waist region of a frame having barbs attached via ferrules to the frame.
Figure 3B:
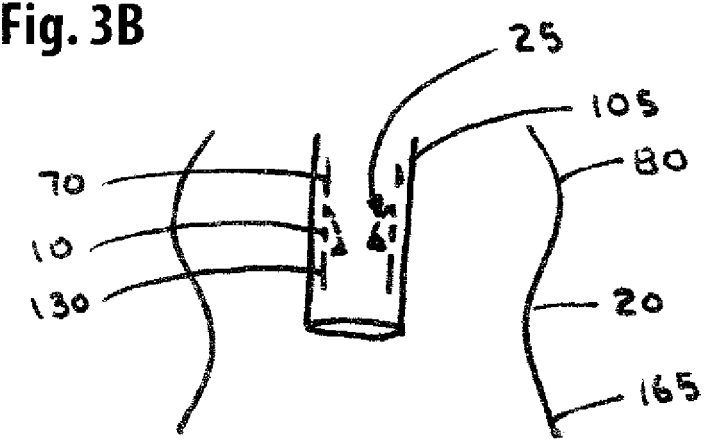
FIG. 3B is a plan view of a stent valve in a smaller diameter configuration positioned within a delivery catheter.

FIGS. 3A-3D show one embodiment of the waist (10) and upper bulb (70) portions of the frame (15) that can be applied to the single member stent-valve (5) and also to the first component (200) of the dual member stent-valve (195). In this embodiment a balloon expandable (BE) set of barbs (25) are located around the waist perimeter (30). The waist (10) is constructed by interleaving a first zig zag stent (240) with a second zig zag stent (245) such that first and second zig zag stents are held together by ferrules (250) placed along the frame or waist perimeter (30). The upper portions of the zig zag stents form the upper bulb (70) and the lower portions of the zig zag stents form the waist. A multiplicity of barbs (25) (range 8-40) are attached to the ferrules (250) such that the barb tip (255) does not extend to the outside of a circle formed by the waist (10) when the stent frame (15) is located within the delivery sheath (105) to reach its expanded configuration as shown in FIG. 3B or after release from the delivery sheath (105) as shown in FIG. 3C. The barb strut (260) is formed from a BE material such that upon exposure to a dilation balloon such as a torus balloon (35) as shown in FIG. 3D (or other shaped dilation balloon), the barb is forced outwards into the annulus (20) via a balloon outward force (228) of the torus balloon (35) onto the barb (25).

The frame waist (10) as shown in FIGS. 3C, 3D, 4C, and 4D can be a portion of a single member stent-valve frame (15) that contains replacement leaflets; alternately the frame waist (10) can be a portion of the first component (200) of a dual member stent-valve (195); the first component (200) of the dual member stent valve (195) does not contain replacement leaflets and serves as an adapter into which a second component (190) that contains replacement leaflets can be positioned and implanted into the central lumen (265) of the adapter.

The barb strut (260) of this embodiment can be formed from stainless steel or plastically deformable metal, polymer, or biodegradable material. The barb tip (255) is formed with a pointed shape that extends in a direction perpendicular to the barb strut (260) and directed toward the tissue of the mitral annulus (20) when it is activated to expand into the annulus via inflation of the torus balloon (35). The barb strut (260) can have a diameter of 0.003 inches (range 0.002-0.006 inches).

The barb tip (255) can be formed from a metal, polymer, or from a biodegradable material such as polylactic acid, for example. The barb tip (255) extends outwards for a distance of 2 mm (range 1 to 4 mm) such that the barb tip (255) will not be able to reach outwards beyond the mitral annulus (20) and extend into the circumflex artery or other inappropriate tissue. The barb should have adequate surface area to ensure that the stent frame (15) does not migrate toward the LA (80) due to pressure and force applied by the LV (165) onto the stent frame; the barb strut (260) can be formed with a flattened shape (see FIG. 20B), for example, to maximized the area of the barb tip (255) that is resisting the migration force imposed by the LV (165) blood pressure. The flattened barb tip (255) can have a dimension ranging from 0.003-0.010 inches in each perpendicular direction forming the barb tip area. Each structural element of the waist (10) (i.e., a zig zag repeat segments, for example) can contain one or more barbs (25) such that the number of barbs (25) along the perimeter of the waist (10) can range from as few as 8 to 40 or more barbs (25). Under the condition that over 40 barbs (25) are placed along the waist (10) of the present stent frame, the length of the barb tip (255) can be reduced to less than 2 mm; for a smaller number of barbs (25), the barb length would extend out at length nearer the upper tip distance range. Approximately 16 barb tips (255) (range 8-40 barb tips) are positioned equally along the perimeter of the waist (10) and extend radially into the native heart tissue for a distance of 3 mm (range 2-5 mm) to hold the stent-frame waist (10) from migrating toward the LA (80) due to LV (165) pressures of 200 mm Hg.

The barbs (25) ensure that the frame (15) of the present invention along with the frictional forces provided by the waist (10) and upper bulb (70) will not migrate towards the LA (80) during the systolic cycle of the heart and also assist in preventing migration into the LV (165) during diastole. It is understood that the barb struts (260) can be formed to be contiguous with the waist (10) portion of the frame (15) or can be attached to the waist (10) portion of the frame (15) via alternate attachment methods including adhesives, brazing, welding, thermal bonding, swaging, crimping with ferrules, and other attachment methods.

Found along the waist perimeter (30) of the single member stent-valve (5) or the first component (200) of the dual member stent-valve (195) embodiment is a limiting cable (225); additional limiting cables (210) can also be located along other perimeters of the frame. The limiting cable (225) can extend through each of the ferrules (250) that are located along a perimeter of the frame; the ferrules (250) can be crimped closed to prevent the stent frame struts (267) of the waist (10) portion of the stent frame (15) from extending outwards beyond a specified preset perimeter. The limiting cable (225) is formed from multiple filaments or other construction and construction materials described previously that are very flexible. The presence of the limiting cable (225) allows the waist (10) portion of the frame (15) of a single member stent-valve (5) to exert a larger (larger than a standard stent of the same diameter) frame outward force (65) prior to being limited by the limiting cable (225) (i.e., equal to a 6 atm (range 2-20 atm) dilation balloon of 35 mm diameter) to ensure that the annulus (20) is formed into a round shape and that direct contact is made between the waist (10) and the annulus (20) along the entire perimeter such that a good seal is created to prevent leakage of blood between the frame (15) and the annulus (20). For a dual member stent-valve assembly the presence of a limiting cable (225) in the waist (10) of the support component or first component (200) that is positioned adjacent to the annulus (20) to provide a defined perimeter ring into which a second component (190) (or valve component) can be delivered to form a frictional or geometric lock between the first component (200) and second component (190); this is further described in later embodiments. The limiting cable (225) prevents the waist (10) from continuing to exert an outward force onto the annulus (20) that can result in unwanted dilation of the annulus (20) which is often times already too large in diameter and is the cause of the mitral regurgitation that is being addressed by the present mitral valve replacement device. A torus shaped dilation balloon (35) (described further in later embodiments) can be dilated to generate a balloon outward force (228) to push the barb tips (255) outwards into the native mitral valve annulus (20) or adjacent tissue to fixate the stent-valve and prevent migration of the stent-valve. Backing member or backing element (450) provides the support for the torus balloon (35) to push against to generate the outward force (228) to move the barb (25) outwards during balloon inflation. The dilation balloon can alternately be replaced by a cylindrically shaped braided expansion member or other expansion member that allows blood flow to pass freely across the expansion member while in an expanded configuration.

Figure 4A:
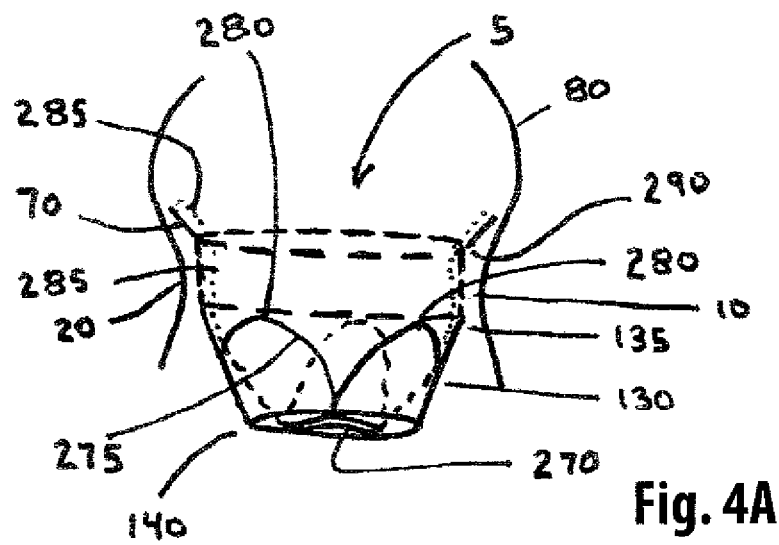
FIG. 4A is a perspective view of a single member frame having replacement leaflets attached within a frustum shaped housing and having a waist located adjacent to the native valve annulus.
Figure 4B:
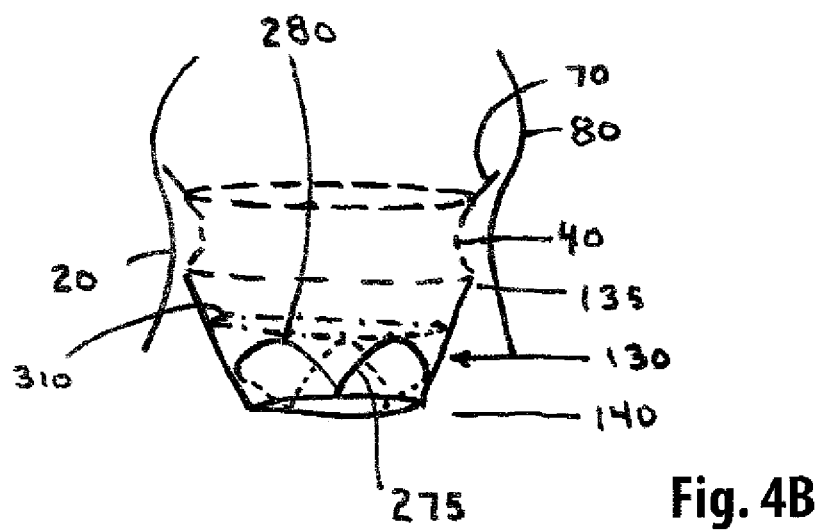
FIG. 4B is a perspective view of a single member frame having replacement leaflets attached within a portion of the frustum-shaped housing and a curved or concave waist located adjacent to the native valve annulus.
Figure 4C:
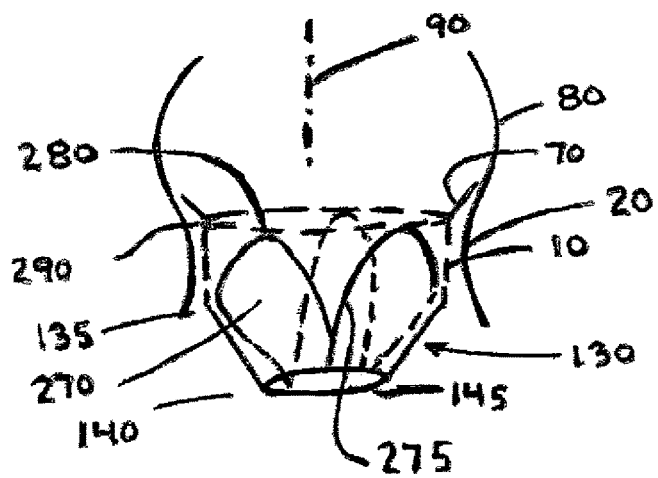
FIG. 4C is a perspective view of a single member frame having replacement leaflets attached within a frustum shaped housing and within the cylindrically-shaped waist located adjacent to the native valve annulus.
Figure 7D:
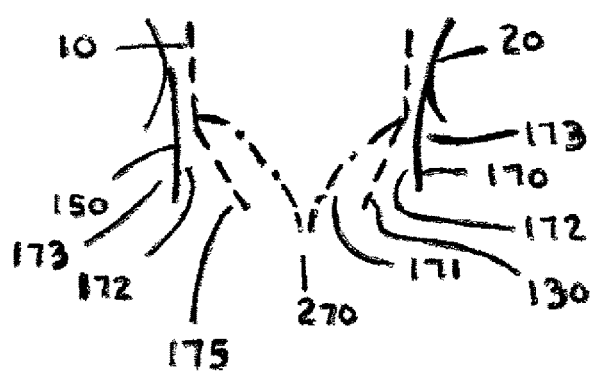
FIG. 7D is a plan view of the single member stent valve identifying the surfaces of the replacement leaflets and the native valve leaflets and flow features of the present design intended to prevent thromboemboli from forming.

FIGS. 4A to 4B show the frustum-shaped or hyperboloid-shaped housing (130) (i.e., frustum-like housing (130)) attached downstream to the cylindrically-shaped waist or curved-shape waist (40) that is located adjacent to the annulus (20). The device as shown in FIGS. 4A-4C can be a single member stent-valve (5) that contains replacement leaflets (270) and is delivered with the frame waist (10) adjacent to the mitral annulus (20). In this embodiment three leaflets are located within the housing (130), however, the present invention can instead include only two leaflets or up to four leaflets. The leaflets are attached to the wall of the housing (130) in a crown-shaped leaflet attachment (275) having the nadirs (280) of the leaflets located at the base of the housing (130) as shown in FIG. 4A, the nadirs can alternately be located between the housing base (135) and the housing top as shown in FIG. 4B or can be located in the waist. The attachment of the leaflets to the housing (130) can be via direct attachment of the leaflets to the struts (267) of the housing frame (130) or to the fabric or covering (285) that is attached to all or part of the housing frame (130). Various forms of attachment of the leaflets can be used including suturing, adhesives, polymer bonding, thermal bonding, and other forms of attachment. In an alternate embodiment the leaflets can be attached to both the housing (130) and the waist (10) as shown in FIG. 4C where the nadirs of the leaflet attachments (275) are located at the junction (290) of the waist (10) and the upper bulb (70) such that the housing length (185) extending in an axial direction (90) from the waist (10) to upper bulb junction (290) to the housing outlet end (145) is reduced, thereby reducing the liklihood for impingement of the housing (130) onto the anterior native mitral leaflet.

In an alternate embodiment, the device shown in FIGS. 4A-4C can be a second member or second component (190) of a dual member stent-valve (195); the second member that contains replacement leaflets (270) would be implanted within the lumen of a first member (or support member) that is initially implanted across the mitral annulus (20) and attached to the native heart tissue via barbs (25) as described in other embodiments.

Figure 5A:
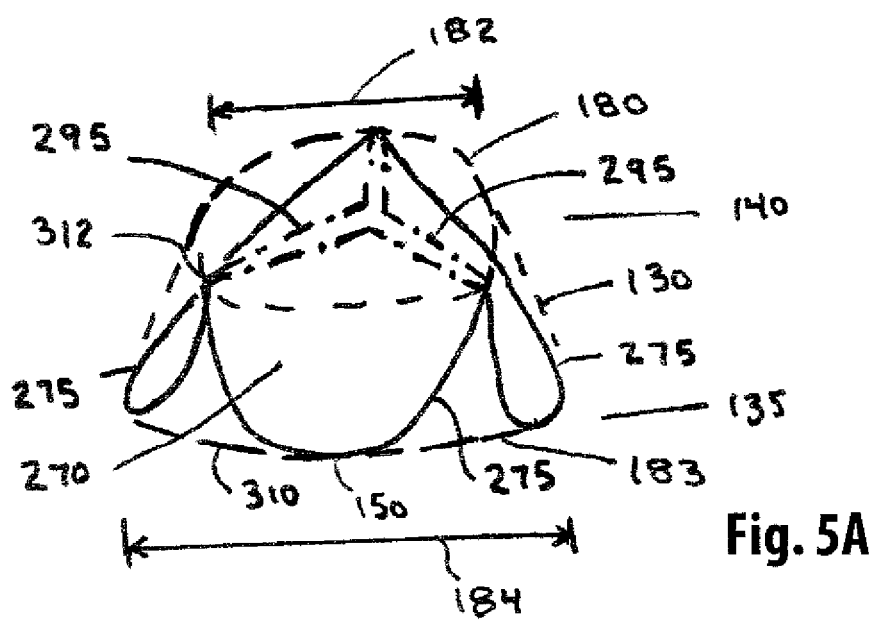
FIG. 5A is a perspective view of frustum shaped leaflets having a free edge perimeter that is smaller than the leaflet base perimeter located at the nadirs of the leaflets.
Figure 5B:
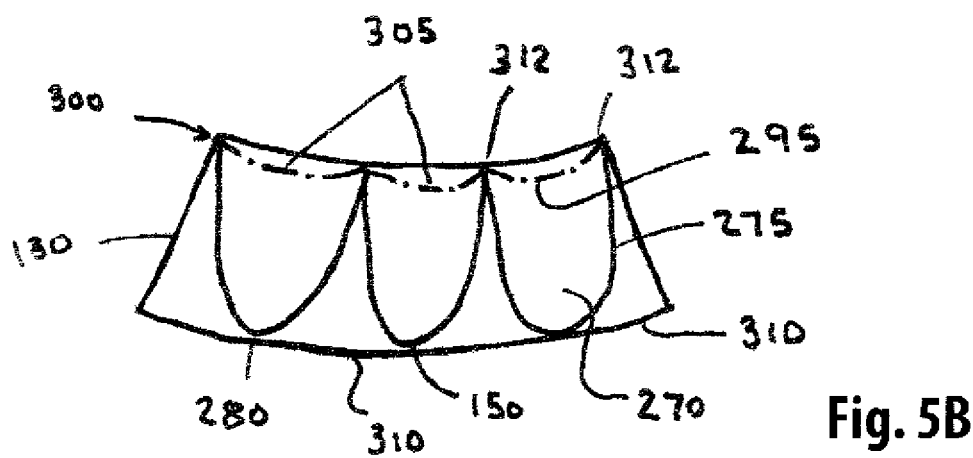
FIG. 5B is a plan view of frustum-shaped leaflets that have been splayed out onto a flat surface showing a smaller free edge perimeter than the leaflet base perimeter.

As shown in FIG. 5A and 5B the leaflets themselves form a frustum-like shape or hyperboloid-like shape that fits precisely within the frustum-shaped or hyperboloid-shaped housing (130). Each leaflet has a free edge (295) that forms a leaflet top (300) and that resides at or near the level of the housing top (or downstream end) of the housing (130); the leaflet free edge (295) has a smaller leaflet free edge perimeter (305) than the housing top perimeter (180); the nadirs (150) of the leaflet attachment (275) to the housing (130) follow a leaflet base perimeter (310) that coincides with the larger housing base perimeter (183) located at the housing base (135). The pressure forces from the LV acting on the free edges (295) of the leaflets and the leaflet regions nearest the free edges (295) are lower due to the reduced area of exposure at the smaller downstream end of the frustum; the leaflets are less likely to undergo stress fracture failure. The housing base perimeter (183) is equal to Pi*D where D is the housing base diameter (184); the housing top perimeter (180) is Pi*d where d is the housing top diameter (182) . FIG. 5A shows a perspective view of the free edges (295) of the leaflets coaptation with each other to prevent flow of blood during systole from the housing top toward the housing base. Upon cutting the frustum-shaped housing (130) along one side and splaying it open as seen in FIG. 5B, one can view the free edges (295) of the three leaflets and the crown-shaped attachment of the leaflets to the frustum-shaped housing (130). The replacement leaflets (270) are attached to the housing top at three commissures (312); the free edges (295) of the leaflets also join to their neighboring leaflet at the commissures (312). The replacement leaflets (270) are attached to the housing (130) along the frustum-like shape of the housing (130) and thereby themselves have a frustum-like shape when the cut edge is closed as shown in FIG. 5A.

The replacement leaflets (270) can be formed from various types of tissues including pericardial tissue or tissues taken from a variety of animal sources. The tissues are often treated via a crosslinking process including glutaraldehyde processing, for example. Other leaflet material include polymer film, ePTFE, Dacron fabric, polyethylene terephthalate film or fabric, polyurethane, composite materials Including Nitinol formed as a composite thin leaflet, or other thin and strong materials that are suitable for implant. A metal frame such as Nitinol, for example, or alternately, fibers can be sandwiched between or contained between polymeric film or tissue film members to provide strength and proper flex characteristics to the replacement leaflets (270); leaflet axial strain of up to 15% is attained during the systolic portion of the heart contraction cycle in comparison to diastole; circumferential strain is limited to less than 10% during systole.

Figure 6A:
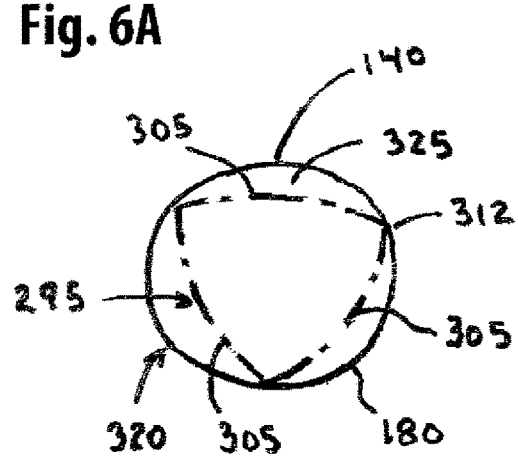
FIG. 6A is a plan view of the cross-section of the housing top viewing the leaflet free edges in an open configuration and having a spacing between the leaflet free edges and the housing top of the frame.
Figure 6B:
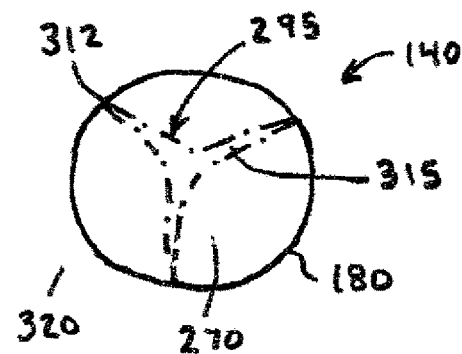
FIG. 6B is a plan view of the cross-section of the housing top viewing the leaflet free edges in a closed configuration.

FIGS. 6A and 6B show an end view of the housing top (140). FIG. 6A shows the leaflets in an open condition as found during diastole; the free edges (295) of the leaflets do not make contact with the housing wall (320) at the housing top (140). The leaflet free edge perimeter is 10% (range 5-20%) less than the housing top perimeter (180). This perimeter difference provides a gap or spacing (325) between the free edges (295) of the leaflets and the housing top between respective commissures (312) to allow for blood flow to the back side or LV (165) side of the replacement leaflets (270) during systole to ensure that the leaflet is properly cleansed by blood flow and reduce thrombus formation, and also provide direct access for blood pressure to assist in closing the leaflets during systole when the native leaflets can be pushed via blood pressure into contact with the housing (130). The leaflet free edge can be seen to be attached to the housing top at each of the three commissures (312). FIG. 6B shows the free edge of the leaflets at the level of the housing top in a closed configuration as found during systole. Here the free edges (295) are seen coapting or touching the free edge of a neighboring leaflet forming a leaflet coaptation (315) to prevent blood flow from the LV (165) to the LA. In an alternate embodiment the spacing (325) can be eliminated allowing the leaflet free edge (295) to come into direct contact with the housing top (140) or other surface of the housing (130).

Figure 7A:
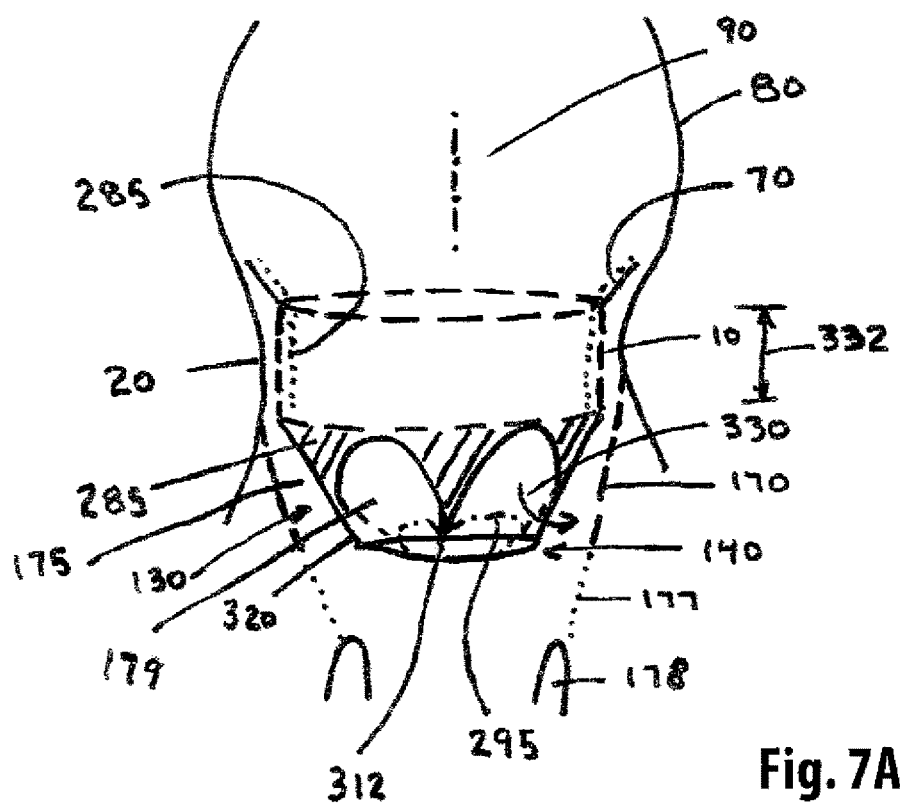
FIG. 7A is a perspective view of single member stent valve having a covering over a portion of the housing and providing an open area for blood flow through the open frame housing during diastole.
Figure 7B:
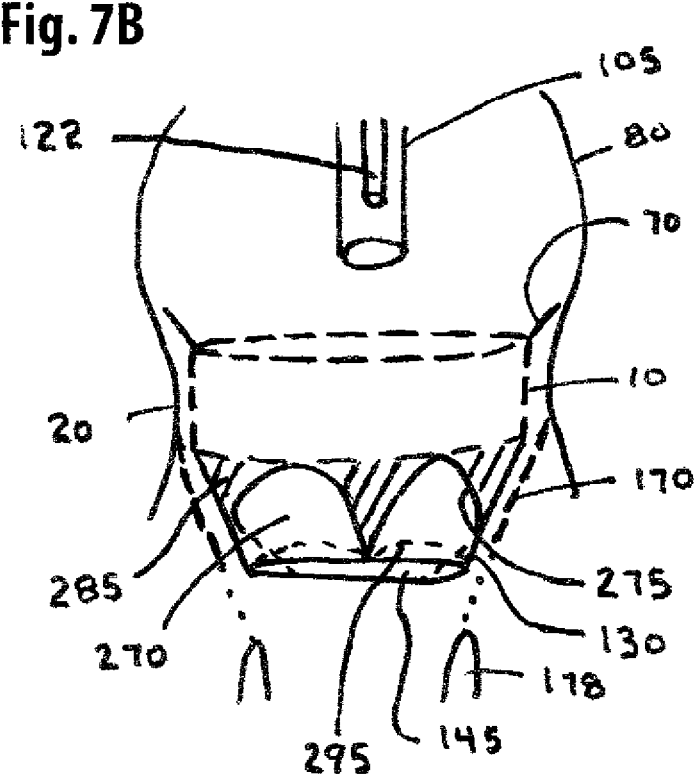
FIG. 7B is a perspective view of single member stent valve having a covering over a portion of the housing and providing an open area for blood flow through the spacing between the frame and the free edges and through the open frame housing during systole.
Figure 7C:
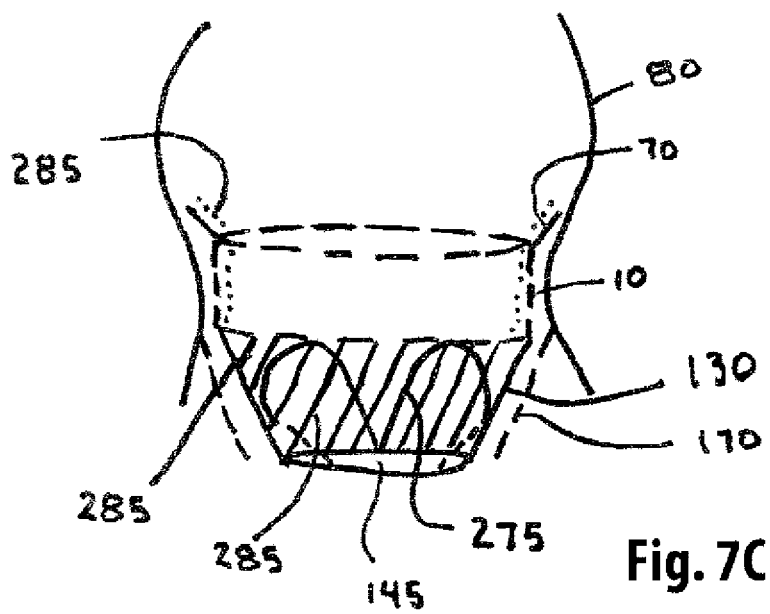
FIG. 7C is a perspective view of single member stent valve having a covering over the entire housing and providing an open area for blood flow through the spacing between the frame and the free edges during systole.

FIGS. 7A-7C show the waist, the upper bulb (70), and housing (130) and the fabric or covering (285) that is attached to all or part of the single member stent-valve frame. The fabric can be sewn, bonded by adhesive, or otherwise attached to the frame (15) of the waist, the upper bulb (70), or the housing (130). The fabric can be formed from an expanded polytetrafluoroethylene (ePTFE), Dacron, a woven fabric, or other thin material that will not let blood flow across its wall thickness. As shown in FIGS. 7A and 7B the fabric is attached along the entire perimeter of the waist (10) and along the entire waist length (332) in the axial direction (90); the fabric extends at least to cover the surface of the housing (130) extending from the housing base (135) to crown-shaped line of attachment of the leaflets to the housing (130). The fabric can also extend to cover the surface of the upper bulb (70) to assist in preventing leakage between the frame (15) and the surrounding tissues of the annulus (20) and LA. The fabric extends to each of the three commissures (312). The remainder of the housing surface (175) is an open housing surface (179) (i.e., without a covering (285)) that allows radial blood flow (330) through the non-covered wall of the housing (130) through the open housing surface (179). As shown in FIG. 7A radial blood flow (330) can occur at the early start of systole into the outlet end of the housing and flow out of the open housing surface (179) as systolic blood flow that will keep the outer surfaces (171) of the replacement leaflets (270) clean and free of thrombotic deposition. During diastole a diastolic blood flow of blood can occur in the form of a recirculation pattern through the open housing surface(179); this blood flow can also help to keep the outer surfaces (171) of the replacement leaflets (270) clean. The native leaflets have blood flow across their inner or central surfaces (172) from the systolic radial blood flow and from the diastolic blood flow to maintain the native leaflets in a condition of pivotal movement at its attachment to the mitral annulus (20) from a leaflet location adjacent the housing outer surface (175) during middle to late systole as shown in FIG. 7B to a location that is removed or separated from the housing outer surface (175) toward the lateral wall of the LV (165) during early systole and during diastole as shown in FIG. 7A.

As shown in FIG. 7C, in an alternate embodiment the fabric or covering (285) can be attached to the entire outer surface of the housing (175). The fabric can also be attached along the waist (10) and can be attached to the upper bulb (70). In this embodiment the native leaflets would tend to position themselves against the housing outer surface (175) during early systole, late systole, and during diastole since blood cannot flow across the housing wall (320) if the housing (130) has a fabric or covering (285). The inner surface (172) of the native leaflets would tend to become attached to the fabric that is located on the housing outer surface (175). The frustum-like shape of the housing (130) allows the native leaflet to lie flat against the outer surface of the housing (175) without restriction from the chordae tendineae. Also, no aspect of the present frame (15) pushes outward on the leaflet with a radial outward component that would limit the ability of the native leaflets from moving into direct apposition with the entire housing outer surface (175). The native leaflets that are in contact with the present housing (130) tend to become healed against the housing outer surface (175) across their entire inner surface thereby eliminating any source for thrombus. Since the housing has a frustum-like shape, the native leaflets can fit snugly against the housing outer surface (175) without the presence of pockets or open areas that can result in thrombus formation. Thus, the shape of the frustum or hyperboloid housing (130) is necessary to ensure that the native leaflets can approximate the housing outer surface (175) and not be held away from the housing (130) by the chordae tendineae or by any structure of the stent-valve frame (15) that can hold the native leaflet from making full approximation with the housing outside surface (175). The outer native leaflet surface (173) would remain free of thrombus due to the direct access to blood flow during systole and the recirculation blood flow in the LV (165) during diastole thereby preventing thrombus formation on the outer surface of the native mitral valve leaflets.

The device of FIGS. 7A-7C and alternately describe a second component (190) (or valve member) of a dual member stent-valve (195). The second component (190) would be delivered into the open central lumen (265) of a first component (200) that was delivered initially across the native mitral annulus (20). The second component waist (205) of the second component (190) stent-valve frame (15) would be positioned adjacent to the waist (10) of the first component (200) as described in subsequent embodiments.

During the method of use for the single member stent-valve (5) the delivery sheath (105) enters the mitral annulus (20) with the waist (10) of the frame (15) located adjacent to the mitral annulus (20) and the sheath is withdrawn partially while holding the pusher member (122) in a fixed position (see FIG. 1A). As the delivery sheath (105) is withdrawn the waist (10) expands out into contact with the mitral annulus (20), the upper bulb (70) expands out into contact with the LA, and the housing (130) is positioned across the native leaflets of the mitral valve. The recapture struts (100) are being held by the release cords that are extending within the pusher tube. If the operator does not consider that the waist (10) is properly positioned adjacent to the mitral annulus (20), the stent-valve can be withdrawn back into the delivery sheath (105) by pulling back with tension onto the pusher while maintaining position of the delivery sheath (105); alternately the stent-valve can be withdrawn by applying tension onto the pusher while advancing the delivery sheath (105) forward under compression. If the position of the stent-valve is acceptable, the recapture struts (100) are released by the release cords such that the recapture struts (100) expand outwards with low radial force into contact with the wall of the LA. The recapture struts (100) are thinner and more flexible than the struts (267) of the waist (10) and the upper bulb (70); their purpose is to allow the frame (15) to be withdrawn into the delivery sheath (105) and the entire frame (15) can be repositioned relative to the axial position of the waist (10) with the annulus (20) or for improved axial alignment such that the device axial direction (90) is collinear with the axial direction (90) of the mitral annulus (20).

As described in earlier embodiments shown in FIGS. 3B-3D balloon expandable fixation elements such as barbs (25) can be attached to the waist portion (i.e., the waist (10)) of the stent frame (15) (i.e., the waist (10), the upper bulb (70), and the housing (130)) of the stent-valve of the present invention. A dilation balloon having a cylindrical shape, hour-glass shape, or other shape can be used as a post dilatation tool to activate the barbs (25) comprised of a barb strut (260) and barb tip (255) by pushing the barb tips (255) outwards into the tissues of the mitral annulus (20). Such a dilation balloon would also block the blood flow across the mitral annulus (20) when it was being inflated thereby negatively affecting blood flow output from the heart to critical tissues of the body including the brain. Furthermore, an inflated balloon can be pushed toward the LA (80) via LV (165) pressure during systole; interaction of the inflated balloon with the stent frame (15) can cause the stent frame (15) to also move toward the LA (80) placing the stent frame (15) in an incorrect position with the waist (10) no longer positioned appropriately adjacent the mitral annulus (20). To address these concerns a torus-shaped balloon (i.e., torus balloon (35)) is presented that activates the balloon expandable fixation elements by applying a balloon outward force (228) to pushes the barbs (25) outwards into the tissues of the mitral annulus (20) and allows blood flow through the central regions of the torus balloon (35) during balloon inflation. The torus balloon (35) in one embodiment is inflated with saline or other similar physiological fluid or solution; the saline is provided an exit opening or balloon port that is used to inflate the torus balloon (35) and also provide a leakage path for fluid to leak out of the torus balloon (35) after the barbs have been activated to an outward position into the annulus or other valve tissue. The leakage path can be via the balloon port; alternately, the fluid can leak out of the balloon via migration of the fluid through the material (such as ePTFE) used to form the wall structure of the torus balloon. The torus balloon (35) of one embodiment is permanently attached to the stent frame (15) and hence is implanted along with the stent frame (15) within the heart; in other embodiments the torus balloon (35) can be removed from the stent frame (15) after the torus balloon (35) has been inflated to activate the barbs (25) and subsequently deflated. In still another embodiment the torus balloon (35) can be filled with a curable polymer, gel, or foam and is retained within the torus balloon (35) and is not allowed to leak out of the balloon following activation of the barbs (25).

Figure 8A:
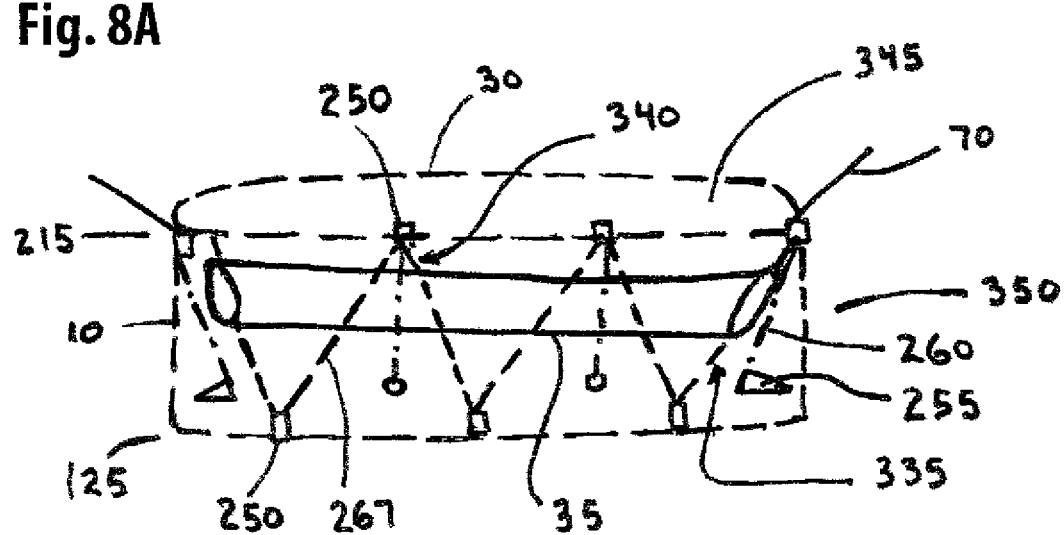
FIG. 8A is a perspective view of a waist region of a frame having barbs attached along a perimeter of the frame and a torus balloon attached along a perimeter of the frame, the torus balloon is not inflated and the barbs are not activated and hence are on the inside or luminal side of the frame.

FIGS. 8A-8D show an embodiment for the waist (10) of the stent frame (15) for a single member stent-valve (5) or for the first component (200) of a dual member stent-valve (195). The frame waist (10) is attached to the annulus (20) via barbs (25) which are activated to force the barbs (25) outward into the annulus (20). The waist (10) of a first component (200) is positioned upstream (95) of the native mitral valve leaflets to reduce interference with native mitral leaflet function. The waist (10) is shown with a torus balloon (35) attached to the waist (10) of the stent frame (15) although it is understood that the torus balloon (35) could be attached to the upper bulb (70) of the stent frame (15) or to the housing (130) of the single member stent-valve. The waist (10) in this embodiment has a frame (15) with from an open cell wall structure but it could equally be formed from a closed cell construction or other wall structures found in stent and stent-valve devices. In this embodiment the waist (10) is formed from a zig zag structure (335) having generally straight stent struts (267) that are joined or contiguous with bent regions (340). This embodiment is shown having ferrules (250) that are located along a perimeter at the waist inlet end (215) or upstream end and waist outlet end (125) or downstream end although it is understood that other stent frame (15) structures without ferrules (250) can be used without deviating from the present invention. The ferrules (250) can be used to attach the barb strut (260) to the waist (10) as shown in FIG. 8A; alternately the barb strut (260) can be formed contiguously with the stent struts (267) or can be attached to the stent frame (15) via an attachment method such as welding, brazing, or via adhesives and not require the ferrules (250) as part of the stent frame. The barb struts (260) are formed from a balloon expandable (BE) material such as stainless steel or other plastically deformable material used in stent construction. At one end of the barb strut (260) is a barb tip (255) that is sharp and pointed outwards toward the outside (350) of the stent frame. The barb tip (255) is 2 mm long (range 1-5 mm) such that it can extend to the outside of the stent frame (15) by 2 mm upon activation into the mitral annulus (20) to hold the stent frame (15) from migration toward the LA. The barb tip (255) can be formed into a flattened shape to enhance the area of contact with the tissue to prevent migration of the stent frame. When the barb tip (255) is inactive, it rests within the frame luminal side (345) and does not extend to the frame outside (350). Located adjacent to and in direct contact with the barb strut (260) towards the inside of the stent frame (15) is the torus balloon (35). The torus balloon (35) of this embodiment is in direct contact with the stent struts (267) and also with barb struts (260). The torus balloon (35) is adjacent to the annulus (20) but does not make contact with the mitral valve leaflet surface on the side of the leaflets that is adjacent to the LV (165) wall or adjacent to the LVOT. In some embodiments the torus balloon (35) is in direct contact with the mitral annulus (20). The torus balloon (35) can be attached directly to the frame struts (267) or the ferrules (250) of the waist (10) of the stent frame (15) via adhesives, sutures, or other bonding methods. Alternately, the torus balloon (35) can be attached to the frame (15) via balloon attachment members (355) that attach to frame attachment sites (360) located on the stent frame. The balloon attachment members (355) are aligned with the barbs (25) in a radial direction such that the balloon attachment members (355) provide a backing support to transfer the outward forces (228) of balloon inflation onto the barbs (25) to move the barbs (25) radially outwards during balloon inflation. The balloon attachment members (355) can be formed from polymer or metal fibers or sutures that can support tension of 5 lbs. (range 1-10 lbs.). The balloon attachment members (355) can be attached to the torus balloon (35) at balloon attachment sites (365); balloon attachment sites (365) for joining the attachment members (355) to the torus balloon (35) can be made via adhesives, fiber attachment, and other bonding methods.

Figure 8B:
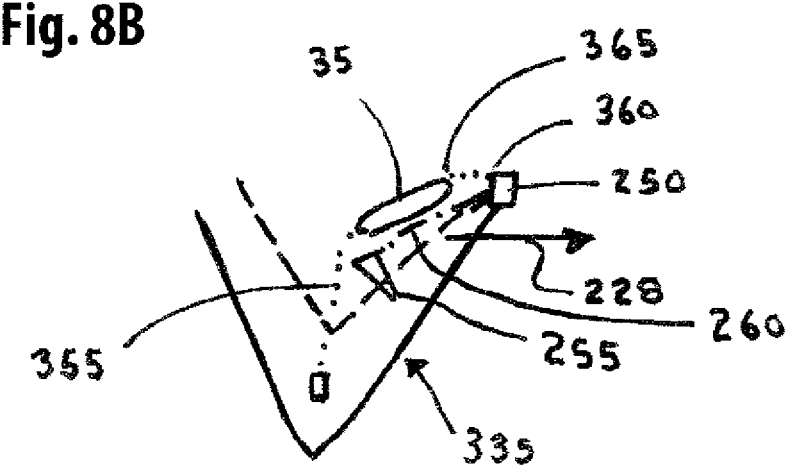
FIG. 8B shows a perspective side view of two frame stent struts and the attachment of the balloon to the frame and attachment of the barb struts to the frame via ferrules; the torus balloon is not inflated.
Figure 8C:
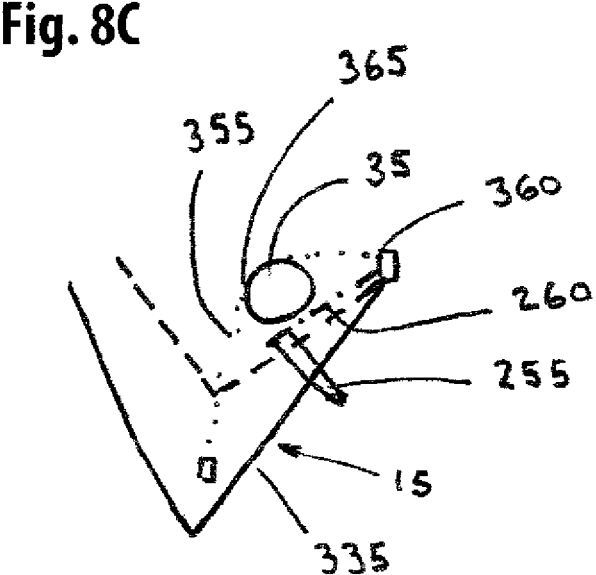
FIG. 8C shows a perspective side view of two frame stent struts and the attachment of the balloon to the frame and attachment of the barb struts to the frame via ferrules; the torus balloon is inflated and the barb tips extend to the outside of the frame.
Figure 8D:
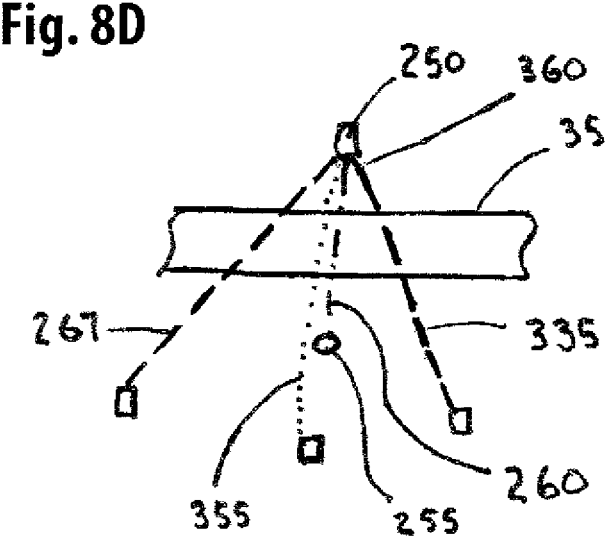
FIG. 8D shows a perspective frontal view of two frame stent struts and the attachment of the balloon to the frame and attachment of the barb struts to the frame via ferrules.

Shown in FIGS. 8B-8D are specific portions of the stent frame (15) as described in FIG. 8A. In FIG. 8B stent struts (267) located at the right side of the waist (10) in FIG. 8A are depicted along with a deflated torus balloon (35) located adjacent to the inside of the barb strut (260). The torus balloon (35) is attached to the stent frame (15) at the stent struts (267), the bent regions, or at the ferrules (250) via attachment members (355). The attachment can be made via a cable or a stent frame member that attaches directly to the torus balloon (35) or provides a support that directs the torus balloon (35) inflation radially outwards into a direction that applies a radially directed balloon outward force (228) against the barb thereby advancing the barb tip (255) into the annulus (20) located outside (350) of the perimeter of the stent frame waist. Upon inflation of the balloon as shown in FIG. 8C the barb strut (260) is pushed outwards placing the barb tip (255) extending outside (350) of the stent frame and into the tissue that surrounds the stent frame (15). A frontal view of the torus balloon (35) located behind a barb strut (260) and also behind (i.e., on the luminal side (345) of) two stent struts (267) is shown in FIG. 8D. The torus balloon (35) can be attached directly to stent struts (267); such balloon attachment sites (365) can be formed with adhesives, polymeric coatings, and other bonding methods. The barb tip (255) faces forward (i.e., toward the observer) and will be pushed further forward as the torus balloon (35) is inflated. Inflation of the torus balloon (35) will push the barb tip (255) outwards to the outside (350) of the stent frame; the torus balloon (35) of this embodiment will remain on the inside of the stent frame (15) and hence will not push the stent frame (15) away from the mitral annulus (20).

Figure 9A:
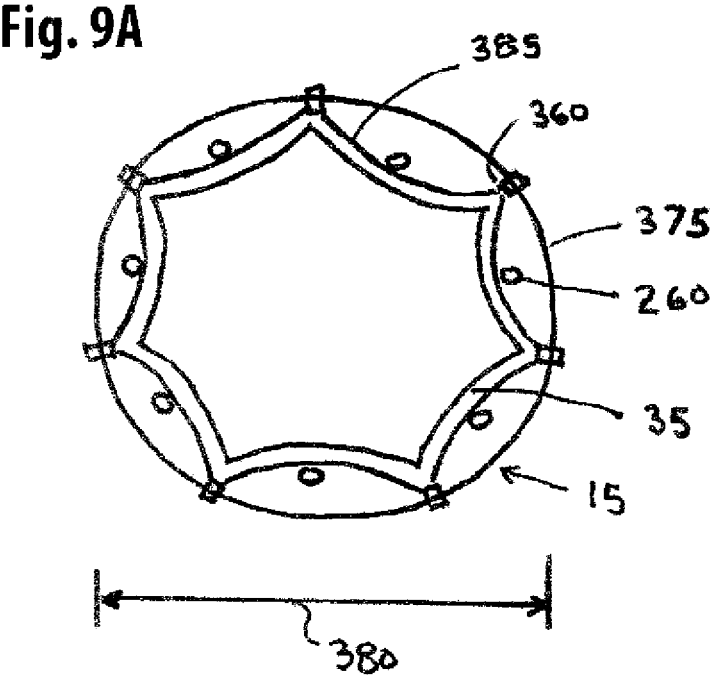
FIG. 9A is a top plan view of the torus balloon attached to the frame with barb struts located to the outside of the outer torus balloon perimeter.
Figure 9B:
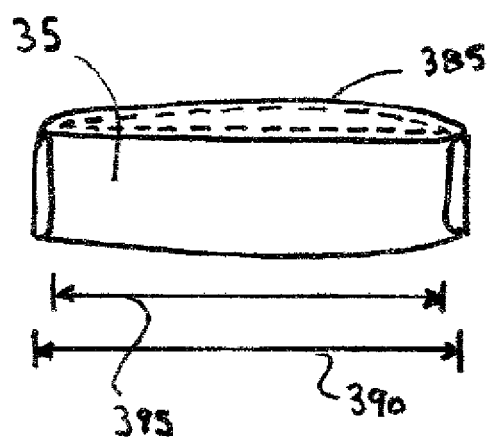
FIG. 9B is a perspective view of the torus balloon showing the balloon diameters and perimeter.

FIGS. 9A and 9C show a top view of the waist (10) region of the stent frame (15) with the torus balloon (35) having balloon attachments (365) made directly to the stent frame (15) or to the ferrules (250). The waist (10) can be a portion of a stent frame (15) of a single member stent-valve (5) or for a first component (200) (i.e., support member) of a dual member stent-valve (195). The balloon attachments of the balloon to the stent frame (15) can be via an adhesive, via thermal bonding, via encapsulation of the stent struts (267) with a polymer, via sutures, or via other attachment methods available to the medical device industry. The torus balloon (35) is attached to stent frame (15) along the stent frame perimeter (375); the torus balloon (35) extends around the inside of the barb struts (260). As shown in FIG. 9A the torus balloon (35) is in a deflated configuration, the inner perimeter and outer perimeter (385) of the torus balloon (35) in a deflated configuration having a flattened shape and similar inner and outer perimeter (385) as seen in FIGS. 9A and 9B;

the torus balloon (35) extends around the inside or frame luminal side (345) of the barb struts (260) and also can be attached to the stent frame.

As shown in FIG. 9C the torus balloon (35) is inflated thereby interfacing with and applying a radially directed balloon outward force (228) to the barb strut (260) causing the barb tip (255) to extend to the outside (350) of the stent frame (15) by 3 mm (range 2-5 mm). The torus balloon outer perimeter (385) of the inflated torus balloon (35) of this embodiment has a balloon outer perimeter (385) that is equal to (range equal to 2 mm greater than) the stent frame perimeter (375) in the waist. The torus balloon inner perimeter (388) is supported by a backing element (450) to allow the inflated torus balloon (35) to push or move the barbs (25) outwards with an outward force (228) such that the barb tips (255) extend to the outside (350) of the stent frame (15). The torus balloon outer diameter (390) is equal to the stent frame diameter (380) of the waist (10) and has a diameter of 35 mm (range 28-45 mm). As shown in FIG. 9D the torus balloon inner diameter (395) in an inflated configuration is smaller than the torus balloon outer diameter (390); the torus balloon cross sectional diameter (400) is 3 mm (range 2-10 mm). The larger torus balloon cross sectional diameter obtained during balloon inflation will provide greater travel distance for the barb strut (260) to extend outwards from an inactive to an active configuration. The larger torus cross section diameter also provides a greater outward force (228) from the torus balloon (35) against the stent frame. The small torus balloon cross sectional diameter will not impact to a significant degree the profile of the stent-valve frame (15) in its delivered configuration and will allow a unrestricted blood flow through its central region in an inflated configuration. The torus balloon inner diameter (395) in an inflated configuration is 25 mm (range 15-31 mm). The torus balloon perimeter (388) provides an open central torus balloon lumen (386) that will not restrict blood flow from the LA to the LV when the torus balloon (35) is inflated.

Inflation of the torus balloon (35) not only activates the barb causing the barb tip (255) to extend into the tissues of the mitral annulus (20) but the torus balloon (35) also improves the contact of the stent frame (15) with the mitral annulus (20). Inflation of the torus balloon (35) causes the torus balloon cross section to take a circular cross sectional shape. This circular cross sectional shape counteracts the desire of the torus balloon (35) to form a kink along its perimeter and hence provide an outward frame expansion force (405) to push the stent frame (15) into intimate contact with the mitral annulus (20). The greater the inflation pressure the greater the outward frame expansion force (405) that can be applied to the stent frame. To improve the outward frame expansion force (405) as well as the balloon outward force (228) pushing on the struts the inflation pressures can exceed 10 atmospheres (range 5-20 atm), if necessary for full frame expansion and for full barb activation. A fiber winding or a braid can be contained within the wall of the torus balloon (35) to provide increased strength to the balloon and allow for higher levels of inflation pressure. Although much lower pressures of 5 atm (range 2-10 atm) are needed to push the barb struts (260) outwards, using a larger inflation pressure will provide proportionally greater outward frame expansion forces (405) by the torus balloon (35) against the waist (10) of the stent frame. In some embodiments of the present invention, portions of the torus balloon (35) makes direct contact with the tissues of the mitral annulus (20) and the inflation medium is held within the interior of the torus balloon (35) following delivery and release of the stent-valve; in these embodiments the torus balloon (35) also contributes to forming an improved seal with the mitral annulus (20) to prevent perivalvular leak.

The torus balloon (35) can be formed from a variety of polymeric materials used to form dilation balloons used in angioplasty. A noncompliant material such as polyethylene terephthalate, for example, can be used to form the torus balloon (35). Alternately, a semicompliant material such as Nylon, Pebax, or a compliant material such as polyurethane can be used; the compliance curve will dictate the inflation pressure that is used to match the perimeter (375) of the stent frame (15) in an inflated configuration. The torus balloon (35) can be formed using balloon blowing processing, for example, in a torus-shaped mold that sets the torus shape into the equilibrium shape of the torus balloon (35). The torus balloon (35) can have one balloon port (410) located at one end of the torus balloon (35) and a dead-end or leak-tight blockage at the other end of the balloon; alternately, the torus balloon (35) can be formed with two balloon ports, one at each end of the torus balloon (35) as shown in FIG. 9D. The torus balloon (35) can also be formed into a complete loop or doughnut shape but with a balloon port to allow for inflation.

FIGS. 10A-10C show an embodiment having the torus balloon (35) contained in a balloon pocket (415) of a balloon holder (420) and having the balloon holder attached to the stent frame (15) via a holder attachment (425). The stent frame (15) can be used as a portion of a single member stent-valve (5) device or as a support member (i.e., first component (200)) of a dual member stent-valve (195). The first component (200) can be an adapter that is able to provide a fixed ring structure attached to the annulus (20) into which a second component (190) (i.e., valve member) can be positioned and implanted. FIG. 10A shows the balloon holder attached to the ferrule (250) of the waist (10) or attached to the stent frame (15) wall structure on the inside of the stent frame (15) or stent frame luminal side (345). The balloon holder wraps around the barb strut (260) toward the inside surface of the barb strut (260). The torus balloon (35) is placed within a balloon pocket (415) formed from the balloon holder in a deflated configuration as shown in FIG. 10A. The balloon holder provides protection to the torus balloon (35) from accidental puncture of the balloon and allows direct attachment of the balloon holder with the stent frame (15) without potentially damaging the torus balloon (35). The balloon holder has an inner layer (430) that faces the luminal side (345) of the stent frame (15) and an outer layer (435) that faces the barb strut (260). The balloon can either float freely within the pocket of the balloon holder or it can be held in place via an adhesive, for example. Upon inflation of the torus balloon (35), the balloon assumes a circular cross sectional shape and applies an outward force (228) against the barb and pushes the barb tip (255) to the outside (350) of the stent frame (15) as shown in FIG. 10B. As shown in FIG. 10C the balloon holder can be attached to the stent frame (15) at the ferrules (250), to the stent struts (267) of the waist, to the bent regions of the stent frame. The holder attachment can be made via sutures, adhesives, thermal bonding, entrapment of the stent frame (15) by the balloon holder, or other attachment methods.

The materials for the balloon holder (420) can include woven fabric, velour, fibrous films, porous films, polymer films that are commonly used in medical device implants. The balloon holder (420) can also serve as a skirt or fabric covering (285) that covers the stent frame (15) and prevents flow of blood across the stent frame wall (440) of the stent frame (15) from the inside or luminal side (345) to the outside (350) of the stent frame (15).

Figure 11A:
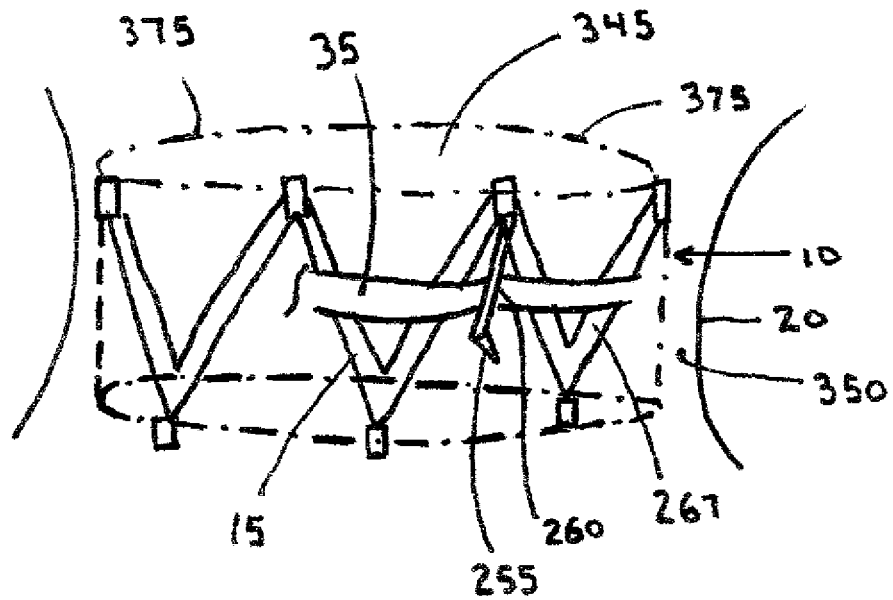
FIG. 11A is a perspective view of a torus balloon that weaves on the outside of two stent frame struts and on the inside of the barb struts as a portion of the drawing of FIG. 11A.
Figure 11B:
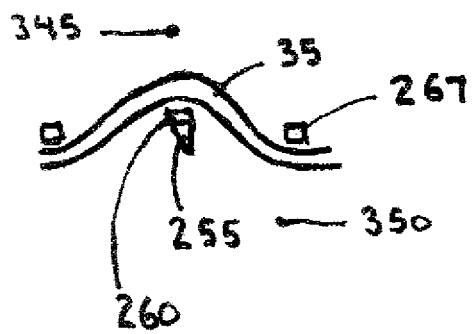
FIG. 11B is a plan view from the top of a frame waist showing the torus balloon extending on the outside of the frame struts and on the inside of the barb struts.
Figure 11C:
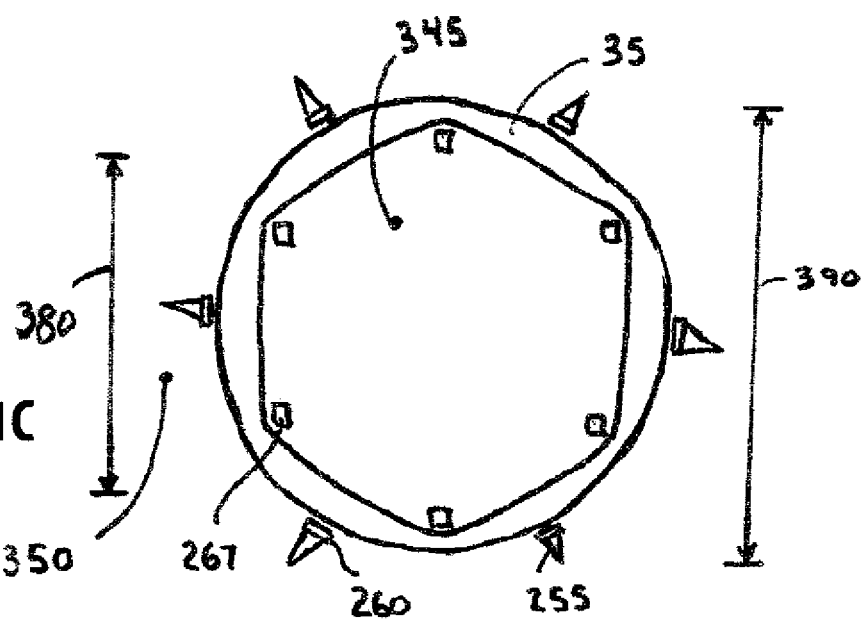
FIG. 11C is a plan view from the top showing the torus balloon weaving to the outside of the frame struts and inside of the barb struts; the balloon is inflated and the barb tips extend to the outside of the frame.

Another embodiment for placement and attachment of the torus balloon (35) within the waist (10) region of a stent frame (15) that is applicable to either a single member stent valve (5) or a first component (200) of a dual member stent-valve (195) is shown in FIGS. 11A-11C. FIG. 11A shows a waist (10) of a stent frame (15) with a deflated torus balloon (35) being placed along the outside (350) of the stent struts (267) and along the inside or luminal side (345) of the barb struts (260). The balloon can be attached to the stent struts (267) and/or the barb struts (260) via an adhesive, for example; the torus balloon (35) can alternately be allowed to move relative to the stent struts (267) and barb struts (260). FIG. 11B shows a top view of two stent struts (267) and a barb strut (260) located in between the stent struts (267); a portion of a torus balloon (35) is shown weaving to the outside of the stent struts (267) and to the inside of the barb strut (260). Upon inflation of the torus balloon (35) as shown in FIG. 11C, the barb tip (255) is pushed outwards placing the barb tip (255) to the stent frame outside (350) and outside of the stent frame perimeter (375) formed by the two stent struts (267). In this embodiment the inflated balloon outer diameter (390) is larger than the stent frame diameter (380) in the waist (10) at a location of the barb struts (260) and barb tips (255). The location of the torus balloon (35) on the outside (350) of the stent frame (15) and on the outside (350) of the stent struts (267) places the torus balloon (35) into direct contact with the tissues of the mitral annulus (20) and the torus balloon (35) forms a direct seal between the mitral annulus (20) and the stent frame. The torus balloon (35) can conform to irregularities in the shape of the mitral annulus (20) and form a continuous seal that will prevent perivalvular leaks between the stent-valve and the mitral annulus (20). The torus balloon (35) can serve as a skirt or fabric to seal the stent frame (15) from perivalvular leaks between the stent frame (15) and the mitral valve tissues. Specific embodiments that use a polymeric material as an inflation medium (i.e., a crosslinking polymeric fluid that converts to a solid or elastomeric matrix or gel or foam) for the torus balloon (35) and also have the means (such as a duckbill valve, for example) to retain the polymeric inflation medium within the torus balloon (35) are suitable candidates for forming such a seal between the torus balloon (35) and the tissues of the mitral annulus (20). Other embodiments can use saline inflation fluid that is able to leak out of the torus balloon (35) through balloon port (410) (normally used for torus balloon (35) inflation) over time as described earlier in other embodiments.

Figure 12A:
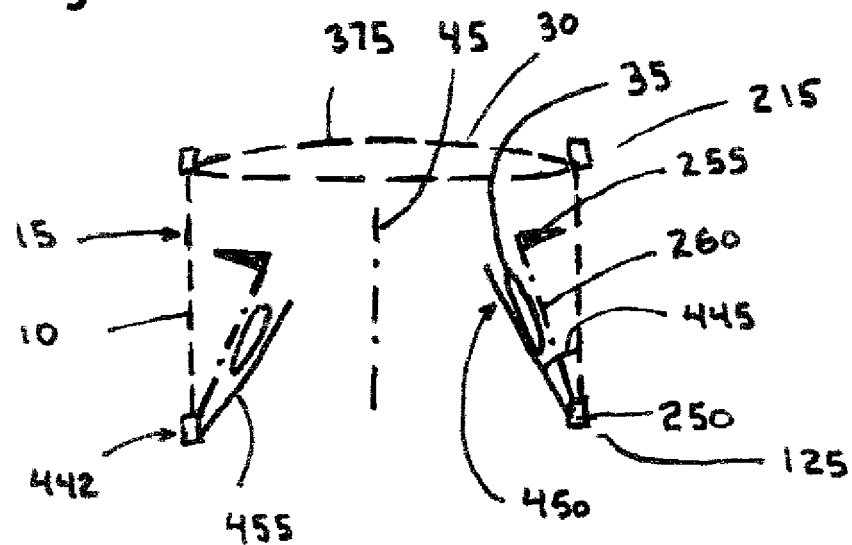
FIG. 12A is a sectional view of a frame waist having a backing arm attached to the frame and supporting the torus balloon on the inside perimeter of the torus balloon.
Figure 12B:
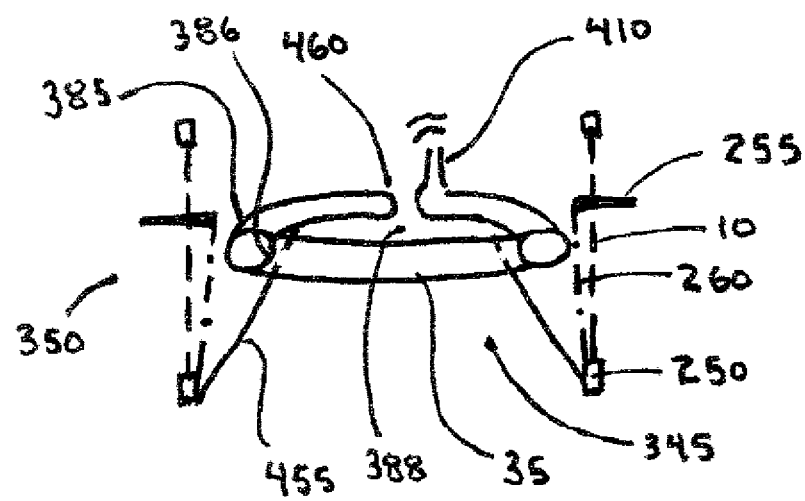
FIG. 12B is a perspective view of the frame waist having a backing arm located on the inside perimeter of the torus balloon; the torus balloon is inflated and activates the barb strut moving the barb tip to the frame outside.

FIGS. 12A-12C show yet another configuration for the torus balloon (35) placement along the waist perimeter (30) of the stent frame (15). The stent frame (15) can be used as a portion of a single member stent-valve (5) or as a portion of a first component (200) (or adapter) for a two-step (or dual member) stent-valve. In this embodiment the BE barb struts (260) are attached to the stent frame (15) via an frame attachment members (442) such as a ferrules (250) located at the waist outlet end (125). The BE barb strut (260) extends proximally within the inside of the stent frame (15) and has a barb tip (255) attached to the barb strut (260), the barb strut (260) extending outwards but remaining within the inside of the stent frame perimeter (375) as shown in FIG. 12A in an expanded configuration after the stent-valve has been released from the delivery sheath (105). A backing element (450) such as a stent arm (455) extends from the attachment member located at the waist outlet end (125) towards the waist inlet end (215) at a stent arm angle (445) such that the proximal end (115) of the stent arm (455) is located inwards from the barb strut (260) toward the stent frame centerline axis (45) and inward from the barb tip (255). The stent arm (455) can be a metal strut attached to the stent frame, the stent arm (455) being formed from a metal or polymeric material. The stent arm (455) is able to provide adequate support such that the barb strut (260) will bend preferentially as the stent arm (455) provides the back-up support for a torus-shaped balloon that is located between the barb strut (260) and the stent arm. The torus balloon (35) is located towards the inside of the barb strut (260) and towards the outside of the stent arm; the torus balloon (35) extends along the perimeter (375) of the stent frame (15) between stent arms and barb struts (260) located at a plurality of 16 (range 8-40) locations along the perimeter (375) of the stent frame; the torus balloon (35) is in direct contact with the stent arm (455) of the stent frame; tissue from the heart valve is not located between the stent frame (15) and the torus balloon (35).

FIG. 12A shows the torus balloon (35) in a deflated configuration with the barb tip (255) located on the inside of the stent frame; the stent frame (15) has been released from the delivery catheter and is in an expanded configuration. The torus balloon outer perimeter (385) matches approximately the expanded stent frame perimeter (375). During delivery of the stent frame (15) within the delivery sheath (105) in a nonexpanded configuration, the torus balloon (35) would be folded along its perimeter to allow for a smaller stent frame perimeter (375) and torus balloon (35) in its nonexpanded configuration within the delivery sheath (105). The torus deflated balloon is located between the barb strut (260) and the stent arm (455). One end of the torus balloon (35) is attached to a balloon port (410) that provides entry of inflation medium to inflate the torus balloon (35); the other end of the torus balloon (35) has a dead end or closed end (460) that does not allow escape of inflation medium from the torus balloon (35).

Upon inflation of the torus balloon (35) as shown in FIG. 12B, the barb strut (260) is pushed outwardly to the outside (350) of the stent frame (15) by the torus balloon (35) as the inflation forces from within the torus balloon (35) are transferred from the stent arm (455) through the torus balloon (35) to the barb strut (260) causing the barb strut (260) to extend outwards and placing the barb tip (255) to the outside (350) of the stent frame (15) and into the tissues of the mitral annulus (20). The torus balloon (35) of this embodiment is located along the perimeter on the inside or luminal side (345) of the stent frame. Following inflation of the torus balloon (35) and activation of the barbs (25) to extend outwards from the stent frame (15) and into the mitral annular tissues, the torus balloon (35) of this embodiment can be removed as shown in FIG. 12C. Upon application of tension (465) at the location of the balloon port (which extends throughout the shaft of the delivery catheter) the torus balloon (35) is pulled upwards such that it is removed from a location between the barb strut (260) and the stent arm (455) as shown in FIG. 12C. The torus balloon (35) which is formed from a soft flexible polymeric material is able to unwind (as shown in FIG. 12C) from its torus shape and be removed from its position between each of the plurality of barb struts (260) and stent arms as balloon port is placed under tension or during removal of the delivery catheter. The torus balloon (35) of this embodiment can be inflated with saline or other contrast medium to activate the barb struts (260) and barb tips (255).

The backing element (450) can alternately be a backing fiber (470) that extends from an attachment element such as a ferrule (250) located at the waist outlet end (125) of the stent frame (15) to an attachment element located at the waist inlet end (215) of the stent frame (15) as shown in FIG. 12D. The backing member (450) resides on the inside perimeter (388) of the torus balloon (35). The backing fiber can be formed from a multifilament or monofilament strand metal or polymeric fiber that is flexible but has high tensile strength such that it will not stretch upon exposure to inflation pressures imposed upon it by the torus balloon (35). The backing fiber extends on the inside portion (i.e., nearest the stent frame (15) central axis(45)) of the torus balloon (35); the torus balloon (35) is located adjacent the inside of the barb strut (260) as shown in FIG. 12D. Upon inflation of the torus balloon (35) with contrast medium (as described in FIGS. 12B), the barb strut (260) is pushed outwards such that the barb tip (255) extends outwards from the stent frame (15) and into the tissues of the mitral annulus (20). The backing element (450) provides the support such that the inflation forces from the inflated torus balloon (35) are transferred directly to the barb strut (260) causing the barb strut (260) to move outwards to the frame outside (350) during inflation of the torus balloon (35). The torus balloon (35) of this embodiment can be removed following activation of the barb tips (255) in a manner similar to that described in the embodiment of FIGS. 12A-12D by placing tension onto the balloon port and pulling proximally thereby unwinding the torus balloon (35) from its torus shape and removing it from the heart, the vasculature, and the body.

In an alternate embodiment the torus balloon (35) described in FIGS. 12A-12D can be attached to the stent frame, the barb struts (260), or the backing element (450) and can be implanted into the patient along with other portions of the stent frame (15) and stent valve. The attachment of the torus balloon (35) to a portion of the stent frame (15) can be made using an adhesive, sutures, thermal processing, or other methods available to bond polymeric or metal components together. In this alternate embodiment, the torus balloon (35) can be filled with either a saline based inflation medium which is allowed to drain or leak out of the balloon following balloon inflation. The torus balloon (35) alternately can be filled with a polymeric material that will cure or harden as described earlier; in this case, a check valve as described in earlier embodiments will be required to ensure that such polymeric material is confined to the inside of the torus balloon (35). As discussed in earlier embodiments, a limiting cable (225) can be attached anywhere along the axial length of the stent frame (15) or to the stent frame along a perimeter of the waist (10) in its expanded configuration and nonexpanded configuration.

Figure 13A:
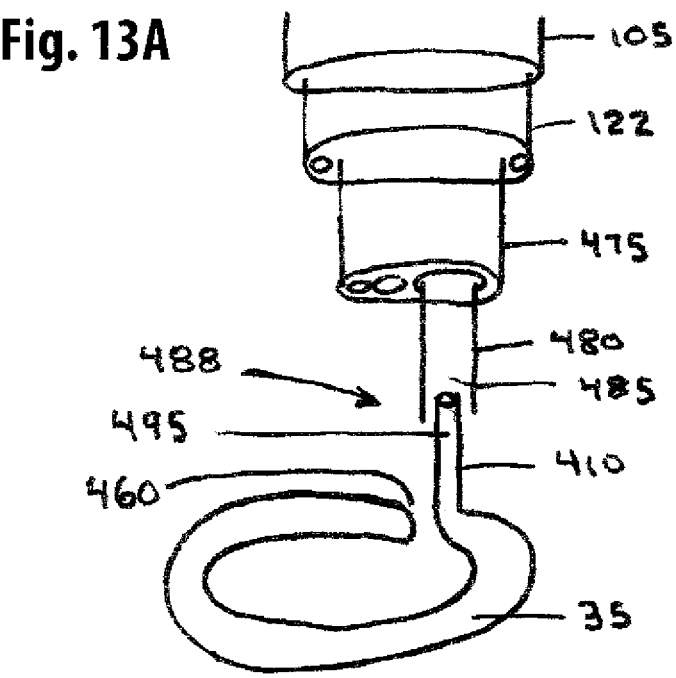
FIG. 13A is a perspective view of the delivery catheter, the pusher member, and the connection of the control shaft with the balloon port.
Figure 13B:
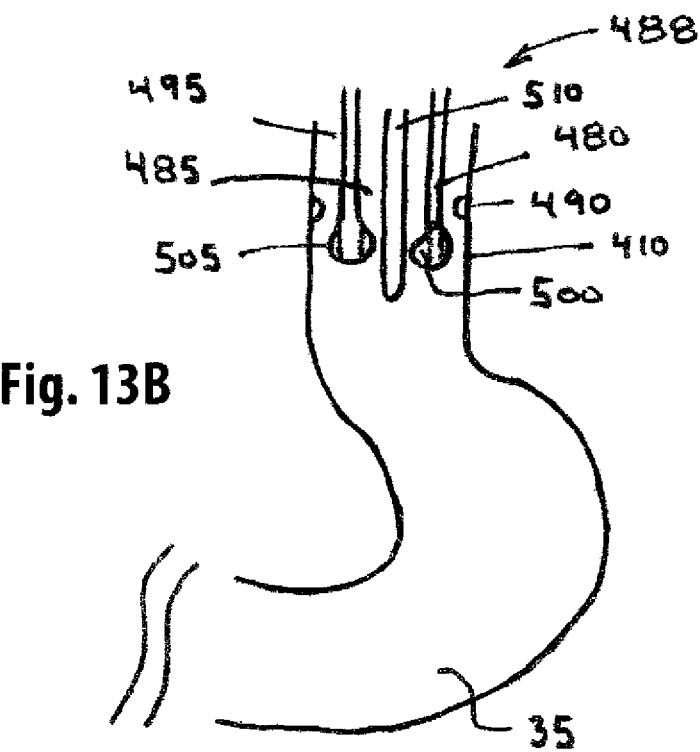
FIG. 13B is a plan view of a connection of the control shaft with the balloon port of the torus balloon using a locking intrusion.
Figure 13C:
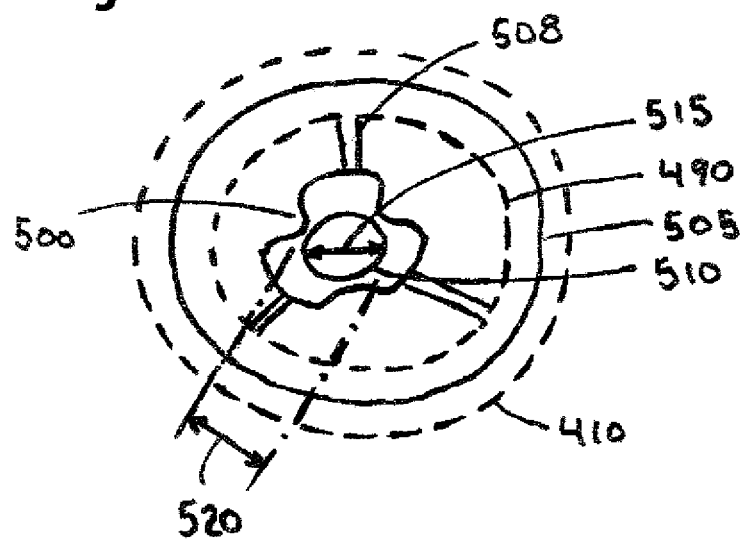
FIG. 13C is a cross-sectional view of the connection of the control shaft with the balloon port having a locking intrusion.
Figure 14:
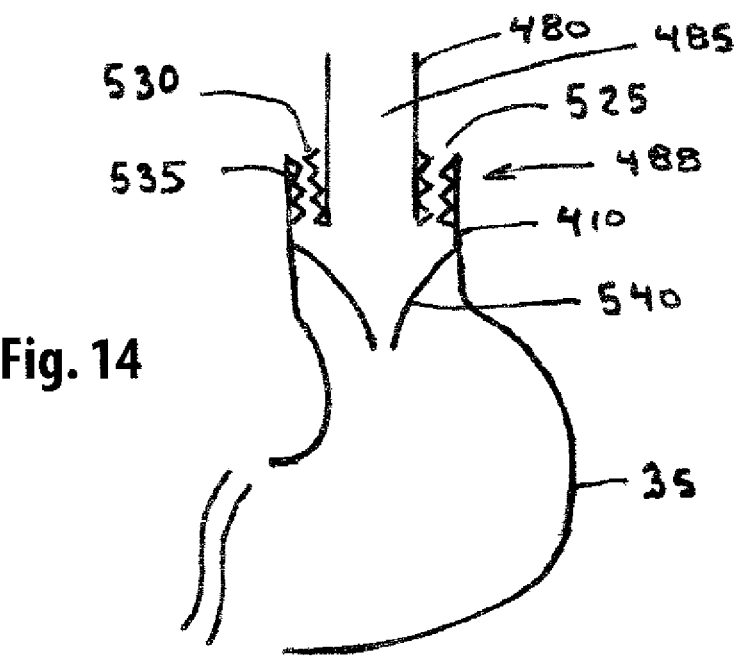
FIG. 14 is a plan view of a threaded connection of the control shaft with the balloon port.

The delivery of an inflation fluid to the torus balloon (35) and detachment of the torus balloon (35) from a control shaft is shown in FIGS. 13A-14. FIG. 13A shows the torus balloon (35) having one balloon port; the torus balloon (35) is understood to be attached to the waist (10) as shown in any of the embodiments described in FIGS. 8-12, but is shown here for clarity as only the torus balloon (35) component of the stent-valve system. A control tube (475) is located within a pusher tube (122) that is located within the delivery sheath (105) similar to that described earlier in the embodiment shown in FIG. 1A. The control tube (475) and the pusher tube (122) can be a single tube in some embodiments rather than two separate tubes. Contained within the control tube is a hollow control shaft (480) that provides a control lumen (485); the control shaft with and inner control lumen are used to provide inflation fluid to the torus balloon (35). The inflation fluid is delivered to the torus balloon (35) under pressure and hence the junction of the control shaft with the balloon port of the torus balloon (35) should not leak significant amount of inflation fluid such that inflation pressure can be attained and must be releasable by the operator at the proximal end (115) of the catheter.

FIGS. 13B and 13C shown one embodiment for a releasable attachment of the control shaft from the balloon port. The balloon port is formed with a locking intrusion (490) that extends inwards into the balloon port lumen (495). The control shaft is formed with 3 inner nubs (500) (range 2-5 nubs) that extend inward into the control lumen as shown in FIG. 13C. The control shaft also has an outer protrusion (505) that has an equilibrium diameter that is larger than the locking protrusion; control slots (508) located in the control shaft (480) allow the control shaft to expand to a larger diameter when a mandrel (510) has been inserted. The outer protrusion of the control shaft can be pushed past the locking protrusion (to engage the control shaft with the balloon port) as long as there is not a mandrel present within the control lumen of the control shaft. Once the control shaft is engaged with the balloon port, a mandrel (510) with a mandrel diameter (515) larger than an equilibrium (i.e., with no external forces impose upon it) nub diameter (520) is placed within the control lumen to form a locked nub diameter to lock the control shaft with the balloon port. Following inflation of the torus balloon (35) via the control lumen, the barb will be activated, and the torus balloon (35) is ready to be disengaged. To disengage the torus balloon (35), the mandrel is removed by applying tension to the mandrel by the operator; with the mandrel removed, the control tube can be removed from the balloon port by applying tension. The torus balloon (35) has therein been effectively inflated and released from the control shaft.

FIG. 14 shows an embodiment that provides a releasable connection (488) comprised of a threaded connection (525) of the control shaft (480) to the balloon port (410) via a screw mechanism. The distal end of the control shaft is fitted with an outer thread (530) that fits within an inner thread (535) located within the balloon port. The control shaft lumen extends through the threaded region to allow for inflation of the torus balloon (35). The control shaft is detached from the balloon port by turning to form a threaded release. A flapper valve (540) or duck-bill valve can be placed within the balloon port to prevent the inflation fluid from draining out of the torus balloon (35) after balloon inflation. Saline can be used as an inflation fluid and allowed to drain out of the torus balloon (35) as described in earlier embodiments. Alternately a polymeric material such as a crosslinking polyurethane, epoxy, silicone, or other polymer or fluid can be used to inflate the torus balloon (35) of this or other embodiments and remain within the implanted torus balloon (35). For the embodiments that use a polymeric inflation medium, the balloon can serve to make a conformal pressure dependent seal with the mitral annulus (20) as it makes direct contact with the tissues of the mitral annulus (20).

Figure 15:
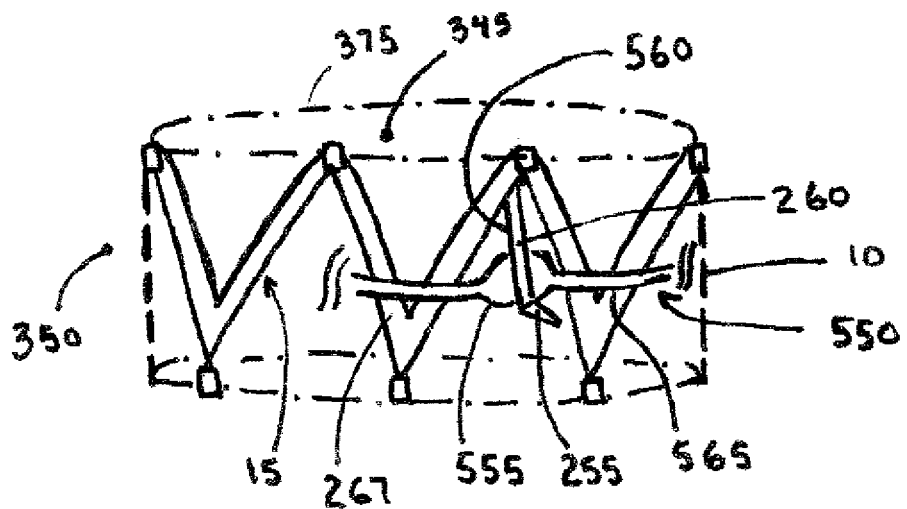
FIG. 15 is a perspective view of a torus balloon having a segmented spherical segment that makes contact with the barb strut.

FIG. 15 shows a side view of a segmented torus balloon (550) having a segmented shape that is located in the waist (10) of a stent frame (15) of the present invention used for a single member stent-valve (5) or a first member (200) of a dual member stent-valve (195). The stent frame (15) and barb struts (260) are similar to the frames and barb struts (260) shown in FIGS. 8A-12B. The stent frame (15) is formed from a SE material and the barb strut (260) is formed such that it is balloon expandable such that it can bend outwards due to an radially outward force (228) against the barb strut (260) generated by inflation of a segmented torus balloon (550). In FIG. 15 the spherical segment (555) of the segmented torus balloon (550) is located adjacent to the barb strut inside surface (560) (i.e., facing the inside (345) of the stent frame) and is inflated with inflation medium such that inflation of the spherical segment (555) will push the barb strut (260) outwards such that the barb tip (255) extends on the stent frame outside (350) of the stent frame (15) as shown for one of the plurality of barbs (25) located along the perimeter (375) of the stent frame. Each spherical segment (555) is located adjacent to an cylindrical segment (565) of a barb strut (260). Each spherical segment (555) is joined to an adjacent spherical segment (555) by a cylindrical segment (565) that retains a smaller diameter during its inflated configuration. The diameter for each inflated spherical segment (555) is 4 mm (range 3-10 mm) and the diameter of each cylindrical segment (565) is 2 mm (range 1-3 mm). The cylindrical segments do not enlarge in diameter as the segmented torus balloon (550) is inflated. At one end of the segmented torus balloon (550) is located a balloon port that is attachable to a fill tube or control shaft that provides inflation fluid to the segmented torus balloon (550). The other end of the segmented torus balloon (550) is dead-ended forming a closed end such that inflation fluid is not able to leak out of the closed end. The segmented torus balloon (550) of this embodiment provides an advantage over a uniformly cylindrical torus balloon (35) as presented in earlier embodiments. The segmented torus balloon (550) can provide a greater excursion or travel distance to the barb strut (260) due to the larger diameter spherical segment (555) while minimizing the profile for the torus balloon during delivery and during inflation of the segmented torus balloon (550) due to the smaller diameter cylindrical segments. During inflation of this segmented torus balloon (550), the cylindrical segments which are at least partially located on the outside (350) of the stent frame (15) do not provide an increased outward push against the mitral annulus (20) during inflation of the balloon since the cylindrical portions do not expand in diameter during inflation. In this embodiment, the inflation fluid is saline and the saline can be released or allowed to leak back into the patient's blood following inflation of the torus balloon in a manner described in earlier embodiments for the torus balloon (35). The balloon is implanted along with the remainder of stent frame (15) and the mitral valve device.

Figure 16:
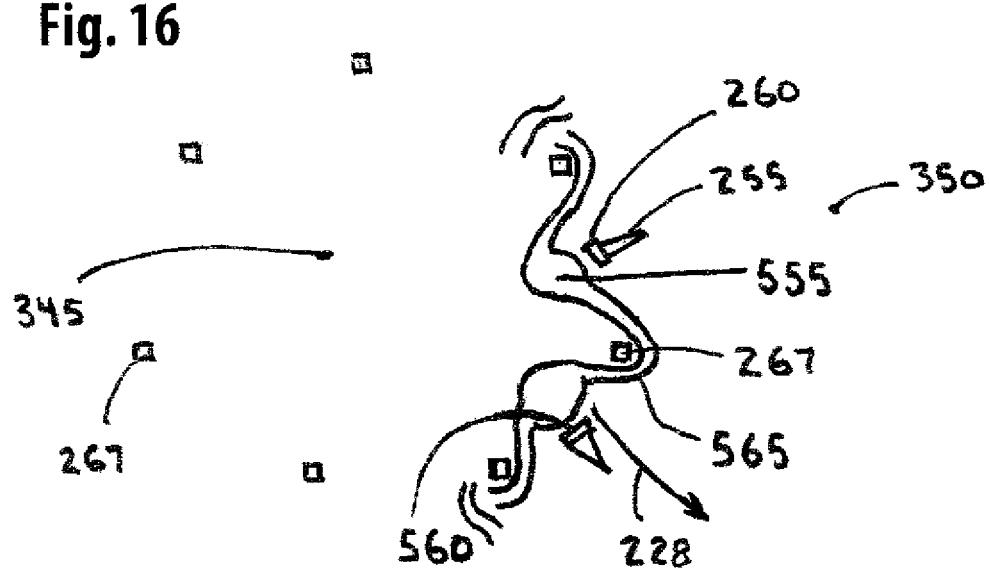
FIG. 16 is a sectional view from the top of the waist region showing the segmented torus balloon moving the barb tips to the outside of the frame during inflation of the torus balloon.

A top view of the segmented torus balloon (550) of this embodiment is shown in FIG. 16 in an inflated state. In FIG. 16 the cylindrical segment (565) is shown extending on the outside (350) of the stent frame (15) adjacent to the stent struts (267). The spherical segments (555) of the segmented torus balloon (550) are located adjacent to the cylindrical segment (565) of the barb struts (260) located facing the stent frame inside (345). During inflation the barb tip (255) is pushed outwards toward the stent frame outside (350) by the spherical segment (555) of the segmented torus balloon (550). The cylindrical portion retains its location on the outside (350) of the stent struts (267) and provides the force necessary to allow the spherical segment (555) to push the barb struts (260) outwards toward the outside (350) of the stent frame. The cylindrical segments can be attached to the stent struts (267) via balloon attachments to hold the segmented torus balloon (550) in position against the stent frame.

Figure 17:
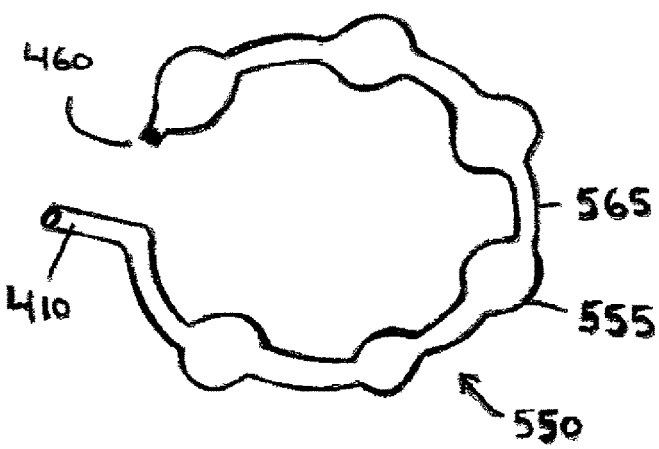
FIG. 17 is a plan view of a segmented torus balloon and a balloon inflation port.

The segmented torus balloon (550) can be formed from similar materials as described earlier for the torus balloon (35). The segmented torus balloon (550) as shown in FIG. 17 can be formed with a series of bulges or spherical segments (555) using polymeric materials and processing methods used to form current dilation balloons used in medical devices. The balloon can be formed with smaller diameter cylindrical segments in series with spherical segments (555); the balloon can have one balloon port located at one end of the balloon; the other end can be closed off and formed to be leak tight forming a closed end (460). Polymeric material for the segmented torus balloon (550) can include polyethylene terephthalate, nylon, Pebax, polyurethane, composites, copolymers, and other polymeric materials used to form dilation balloons for angioplasty and stent delivery catheters.

A shaped mold having regions with bulges can be used to form the segmented torus balloon (550) having spherical segments (555) and cylindrical segments. The mold has bulges or spherical mold segments located in series with smaller diameter cylindrical segments. Standard balloon blowing and molding techniques can be used to form the segmented torus balloon (550). The segmented torus balloon (550) can alternately be formed by bonding segments of cylindrical tubing to other segments having a spherical shape; such bonding can be accomplished via solvent bonding, adhesive bonding, thermal bonding or other suitable bonding method.

In other embodiments for the segmented torus balloon (550) of the present invention, the segmented torus balloon (550) can be inflated with a polymeric material and retained within the balloon via a valve as it is implanted as described for other embodiments for the torus balloon (35). Also, in other embodiments, the segmented torus balloon (550) can be located such that the cylindrical segments are located on the inside of the stent frame (15) and attached by balloon attachments as described in earlier embodiments for the torus balloon (35).

In further alternate embodiments of the present invention used as a single member stent-valve, the barb struts (260) that are used to hold the stent frame (15) adjacent to the mitral annulus (20) and prevent migration of the stent valve can be attached, joined, or contiguous with the upper bulb (70) or the housing (130) rather than attached, joined, or contiguous with the waist (10) of the stent frame. In one embodiment, as shown in FIG. 18, the stent frame (15) does not have a cylindrical waist (10) portion and instead has a frustum-shaped housing (130) that is directly joined to the upper bulb (70). The barb struts (260) of this embodiment are located within or attached to the housing (130) portion and the barb tip (255) is located near the bulb/housing junction (568). The BE barb struts (260) are pushed outward due to expansion of the torus balloon (35); the torus balloon (35) can be the segmented torus balloon (550) or a torus balloon that is cylindrical throughout as discussed in earlier embodiments. The torus balloon (35) can be located on the outside (350) of the stent struts (267) and outside (350) of the stent frame (15) as shown in FIG. 18 and having a segment of the balloon located on the inside of the barb struts (260) such that inflation of the balloon pushes the barb struts (260) outwards. The torus balloon (35) can alternately be located on the inside of the stent frame (15) such that inflation of the torus balloon (35) does not push the stent frame (15) away from the mitral annulus (20). The replacement leaflets (270) are located near the outlet end (145) of the housing.

Alternately, as shown in FIG. 19 for an embodiment of a single member stent-valve, the barb struts (260) and torus balloon (35) can be joined, attached, or contiguous with the upper bulb (70). In this embodiment, the upper bulb (70) is joined directly to the housing (130) and does not contain a cylindrical waist (10) region located between the upper bulb (70) and the housing (130). The barb tips (255) are located near the bulb/housing junction (568) such that the barb tips (255) are extended outwards via inflation of the torus balloon (35) and extend the barb tips (255) into the mitral valve annulus (20). The torus balloon (35) can be located such that it weaves in an out over the outside (350) of the stent struts (267) and adjacent the inside of the barb struts (260) as described in earlier embodiments. Alternately, the torus balloon (35) can be located on the inside surface of the stent frame (15) as well as the cylindrical segment (565) of the barb struts (260) as described earlier.

FIGS. 20A and 20B show an embodiment for a first component (200) (or support member) of a two component or dual member stent-valve. The support member (200) provides a ring like structure (via the limiting cable (225)) having a defined maximum perimeter (375) for the frame (15) that is attached to the mitral annulus (20) via barbs (25), and does not interfere with the function of the native mitral valve leaflets. A valve member (or second component (190)) that contains replacement leaflets (270) provides a second component (190) that is delivered within the central lumen (265) of the first component (200) and is held in place via a friction fit or via geometrical locking of the first component (200) with the second component (190). The first component (200) can be an adapter into which the second component (190) containing the replacement leaflets (270) can be positioned and implanted. The second component (190) can be a specific stent-valve such as presented in embodiments of this patent application; the second component (190) can alternately be an existing stent-valve, such as a BE or SE stent-valve used in TAVR procedures, for example.

The first component (200) has a self-expanding (SE) stent frame (15) that is comprised of a frame waist (10) that can be attached to or contiguous with the upper bulb (70). A valve member or second component (190) which will be discussed in a later embodiment is delivered subsequent to the delivery of the first component (200) within the open central lumen (265) located of the first component (200); the second component (190) is attached to the first component (200) via friction or geometrical fit to the first component (200) that is obtained by expanding the second component (190) within the first component (200). The SE stent frame (15) of the first component (200) can be formed from Nitinol, Elgiloy, or other elastic material used in the formation of vascular stents. The waist (10) is positioned adjacent the mitral annulus (20) and the upper bulb (70) may be located in the LA (80) adjacent to the mitral annulus (20); the upper bulb (70) has a diameter at its inlet end that is larger than the waist inlet diameter (55) to assist in positioning the stent frame (15) across the mitral annulus (20) with the upper bulb (70) resting in the LA, adjacent and upstream of the mitral annulus (20). Positioning of the stent frame (15) into contact with the native mitral valve apparatus tissue is performed via release from an external sheath using a pusher member (122) as described in earlier embodiments described in the present application and patent applications that are referenced in the present application. Recapture struts (100) can be attached to the upper bulb (70) or the waist (10) of the present stent frame (15) to assist in repositioning or removal of the first component (200) in a manner consistent with the stent embodiment described in earlier embodiments. The first component (200) serves to provide a stable location that will hold a second component (190) that contains the replacement leaflets (270) for the mitral valve system of the present invention. The first component (200) allows the second component (190) to be expanded within the inside of the first component (200) and the first component (200) has a specific waist diameter that provides the necessary frictional force against the second component (190) or geometrical shape to hold the second component (190) from migrating downstream and ensuring that leakage does not occur between the first component (200) and the second component (190). A limiting cable (225) can be placed along the perimeter (375) of the stent frame (15) of the first component (200) to limit the stent frame diameter (380) and perimeter (375) of the stent frame (15) from further expansion due to outward forces from the frame of the first component (200) or second component (190) or from an inflation balloon; the limiting cable allows the second component (190) to be expanded into the first component (200) under a greater force (greater than without the limiting cable (225)) that is at least equal to a 10 atm cylindrical dilation balloon to create a tight fit between the first and second component (190). The first component (200) must also be placed within the mitral valve apparatus in a manner that will not affect the functioning of the native mitral valve leaflets during the period of time while awaiting the placement of the second component (190) into the first component (200). In the present invention the first component (200) is placed above or superior to the mitral valve leaflets and extends from the junction (570) of the native mitral valve leaflets to the mitral annulus (20) and can come into contact with the junction (570) of the native mitral valve leaflets with the annulus (20). The native mitral valve leaflets are able to function while the first component (200) is placed adjacent to the mitral annulus (20) and other native tissues of the native mitral apparatus.

The upper bulb (70) of the first component (200) serves to help prevent migration of the first component (200) toward the LV (165), to provide a seal to prevent blood leakage between the first component (200) and the mitral tissues including the LA (80) wall, mitral annulus (20), and mitral leaflets, and to assist in positioning of the first component (200) across the mitral annulus (20) with the upper bulb (70) being located in the LA just proximal to the annulus (20). As shown in FIG. 20A, the barbs (25) which are comprised of barb struts (260) (range 8-20 in number) and barb tips (255) are located along the waist perimeter (30) (see FIG. 20B); the barbs (25) can be formed from a SE elastic material such as Nitinol, for example, or can be formed from a BE material such as stainless steel, for example or from other metals or polymers. Prior to delivery of the first component (200) the barbs (25) are in an inactive configuration located toward the inside of the first component (200) in the central lumen (265) as described in earlier embodiments. Upon activation of the SE or BE barbs (25) outwards to the outside (350) of the waist, the barb tips (255) penetrate the mitral annulus (20) as shown in FIG. 20A or penetrate the base of the native mitral leaflets near the mitral leaflet junction (570) with the mitral annulus (20). Activation of the barbs (25) into the mitral tissues prevents migration of the first component (200) upstream (202) towards the LA (80) and also prevents migration downstream into the LV.

The barb tips (255) can be formed from a material with a sharp tip that can penetrate the tissues of the mitral annulus (20) or the base of the native mitral leaflets. The barb tips (255) can be formed with a flattened shape such that the surface area of the flat barb tip (255) (see FIG. 20C) is maximized in a direction facing the LA (80) or LV to resist movement of the first component (200) towards the LA (80) or LV (165). A covering (285) can be attached to all or a portion of the frame waist (10) and upper bulb (70) frame to prevent blood flow from crossing the wall of the waist frame or the upper bulb (70) frame; the covering (285) can be located on the inside or outside surface of the stent frame

(15) and helps to ensure that perivalvular leakage around the stent frame (15) is minimized. The covering (285) material can be a thin polymeric film or weave, for example, as described in earlier embodiments. Attachment of the covering (285) to the frame (15) can be via sutures, adhesives, and various bonding methods.

One important aspect of the of the present invention is that the barbs (25) are not released or activated until the stent frame (15) has been expanded into the native mitral tissues and is in an expanded configuration. Activation of the barbs (25) after the SE stent frame (15) is expanded and placed into full contact along the entire perimeter of the waist (10) with the full perimeter of the mitral annulus (20) and other mitral tissues ensures that the barbs (25) are placed evenly around the perimeter of the mitral annulus (20) and mitral tissues. Since the mitral annulus (20) and base of the mitral valve leaflet junction (570) to the mitral annulus (20) is not actually round in shape in its native configuration, the mitral tissues will be forced into a round shape by the waist stent frame (15) prior to activation of the barbs (25). The rounding of the mitral annulus (20) by the stent frame (15) of the present invention is not restricted by undesirable premature activation of barb tips (255) into the mitral annulus (20) perimeter in an incorrect position which could occur if the barbs (25) were activated prior to full expansion of the stent frame perimeter (375) into contact with the perimeter of the annulus (20). Premature activation of the barb tips (255) would result in uneven spacing of the barbs (25) around the perimeter of the mitral annulus (20) or base of the mitral leaflet tissues and would not allow the mitral annulus (20) to fully enlarge to a round shape representative of the perimeter of the mitral annulus (20).

Another important aspect of the first component (200) of the present invention is that during activation of the barbs (25), the blood flow through the mitral annulus (20) or stent valve frame (15) should not be blocked. Blockage of mitral blood flow can result in high forces being placed onto the first component (200) during the systolic cycle of heart pumping; such forces can cause movement of the first component (200) towards the LA (80) negatively affecting the positioning of the first component (200) accurately in an axial direction (90) across the annulus (20). The use of a torus balloon (35) prevents the unwanted blockage of blood flow during delivery of the first component (200) and activation of the barbs (25) with the torus balloon (35). Additionally, mitral blood flow blockage can negatively impact oxygen transport to tissues fed by the outflow from the heart including the brain.

Figure 21A:
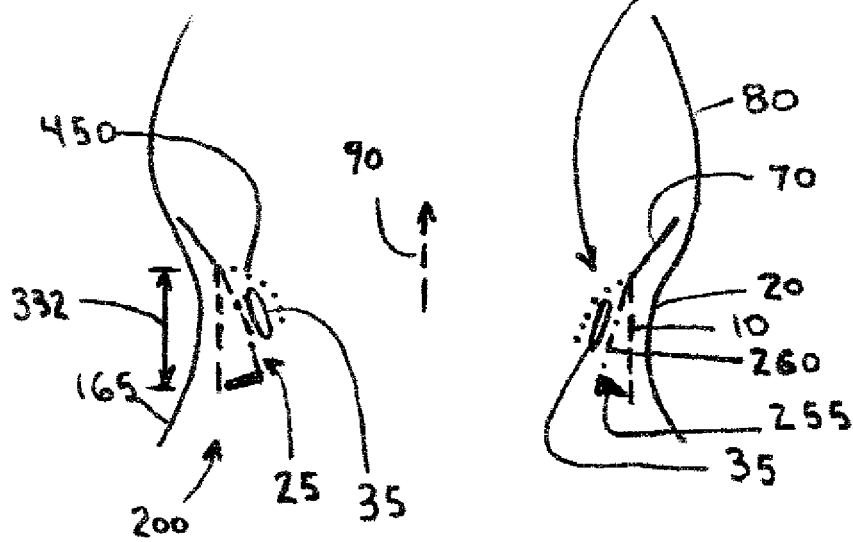
FIG. 21A is a sectional view of a first component or support frame with a backing member and having a torus balloon in a deflated configuration and barb tips inside of the frame.
Figure 21B:
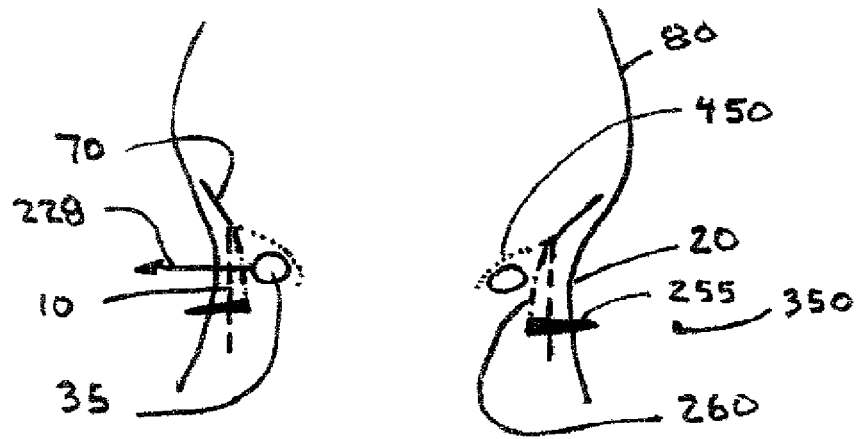
FIG. 21B is a sectional view of a first component or support frame with a backing member and having a torus balloon in an inflated configuration and barb tips outside of the frame.

FIGS. 21A and 21B show one embodiment for activation of BE barbs (25) that are located along a waist perimeter (30) of the first component (200) of the present embodiment or along the waist of the single member stent-valve (5) described earlier. The frame has been released and has expanded out to an expanded configuration (575); the barbs (25) have not been activated as shown in FIG. 21A. The first component (200) of this embodiment has an upper bulb (70) attached to the waist, the upper bulb (70) provides a benefit for proper placement of the first component (200) adjacent to the mitral annulus (20) and assisting with forming a seal between the frame (15) and the mitral annulus (20). The waist (10) of the first component (200) is similar to the waist that is described in earlier embodiments found in the present patent application. The waist can be cylindrical in shape or can have a concave or curved shape as will be described in other embodiments. The waist can have a waist length (332) in an axial direction (90) of 6 mm (range 3 mm-10 mm) and is formed from a stent structure that is open cell, closed cell, a combination of open and closed cell, or other structure found in vascular stents used in the medical device industry. The waist is placed adjacent to the mitral annulus or native mitral valve tissue such that the first component frame does not affect the movement or valvular function of the native mitral valve leaflets. In this embodiment, as described earlier for a single member stent valve (or one-step mitral valve device having the replacement leaflets (270) contained within the stent frame (15) that is attached or contiguous with a waist frame) a torus balloon (35) is inflated to apply an outward force (228) onto the barbs (25) causing the barb tips (255) to move outwards to the stent frame outside (350) and into the annulus (20) or tissue of the heart valve. In this embodiment a backing element (450) such as a stent arm (455) serves to provide a member that is attached to the stent frame (15) and provides the torus balloon (35) with a backing member of which the torus balloon (35) can be located in an uninflated configuration as shown in FIG. 21A and with the barb in an inactivated state. The inflated balloon can push against the barb strut (260) to cause the BE barb strut (260) to extend and plastically deform towards the outside (350) of the stent frame (15) and into the mitral tissues in an activated configuration as shown in FIG. 21B. The backing member (450) provides the support to allow the torus balloon (35) to push with an outward force (228) that is equal to its internal inflation pressure to extend the barb tips to the frame outside (350) and into the surrounding tissues of the heart valve. The first component (200) of the present invention can utilize any of the device mechanisms described in earlier embodiments of the present patent application to activate the barbs (25) into the mitral tissues. For example, the first component (200) can have the torus balloon (35) attached to the waist frame or the stent frame (15) as described in FIGS. 8A-8D and 9A-9D. Alternately, the torus balloon (35) for the first component (200) can be located in the waist (10) region of the first component (200) and can be located in a balloon holder and attached to the frame (15) and activated in a manner that is the same as that described in FIGS. 10A-10C. The torus balloon (35) of the first component (200) of the two step embodiment can have the torus balloon (35) located on the outside of the struts (267) of the frame waist (10) and on the inside of the barb struts (260) as shown in FIGS. 11A-11C. The torus balloon (35) of the first component (200) can be permanently attached to the first component (200) and implanted along with the first component (200) or can be removable as described in FIGS. 12A-12D. The torus balloon (35) of the first component (200) can be a segmented balloon as described in FIGS. 15 and 16.

Figure 22A:
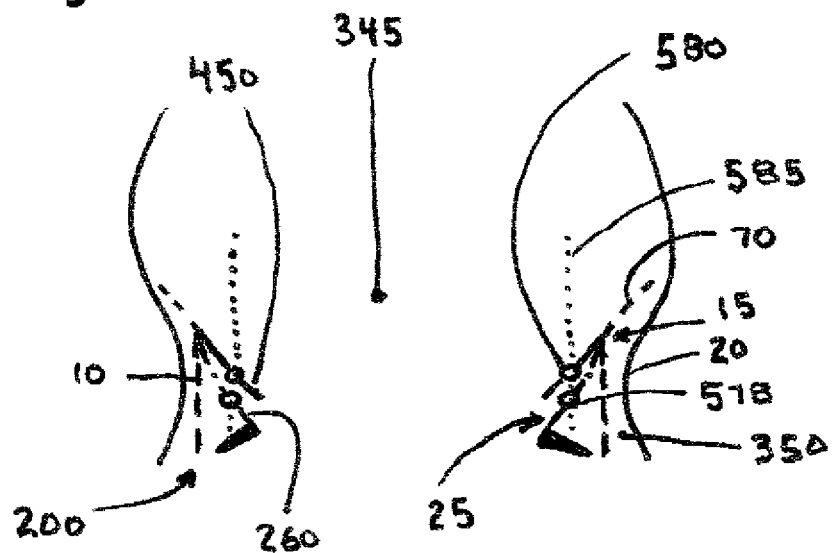
FIG. 22A is a sectional view of a first component or support frame having self-expanding barb struts held in an inactive configuration by a barb control fiber.
Figure 22B:
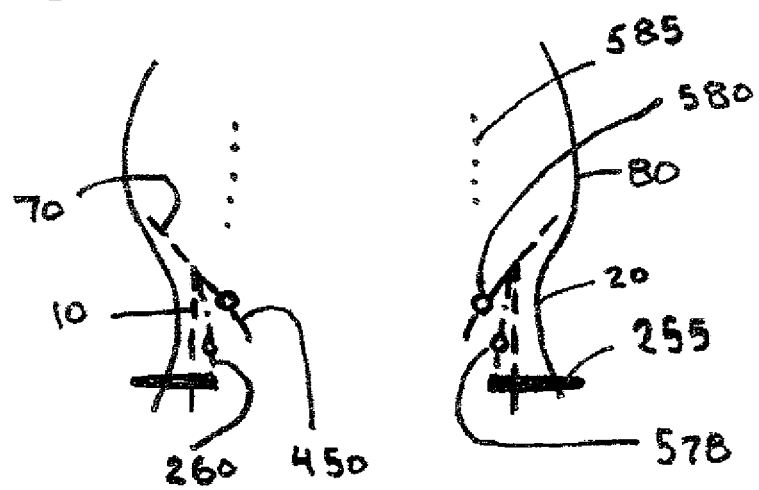
FIG. 22B is a sectional view of a first component or support frame having self-expanding barb struts that have been release by a control fiber and are in an active configuration with the barb tips outside the frame.

FIGS. 22A and 22B show another embodiment for the first component (200) for the mitral valve assembly of the present invention. This embodiment has a waist (10) and upper bulb (70) that is similar to that described in FIGS. 21A and 21B. The barb struts (260) for this embodiment are SE barb struts (260) rather than the BE barb struts (260) found in the embodiment of FIGS. 21A and 21B. This embodiment does not require the presence of a torus balloon to effect the active deployment of the barbs. The barb struts (260) are attached to the frame (15) in a manner similar to that described in earlier embodiments of the present patent application. The barb struts (260) have a barb feature (578) that allows passage of a barb control fiber (585). A backing element (450) such as a backing arm, for example, is attached to the stent frame (15) to provide a holding member that can hold the barbs (25) in an inactive configuration as shown in FIG. 22A. The backing arm has an opening feature (580) that allows passage of a barb control fiber (585). The barbs (25) are held in an inactive configuration towards the inside of the stent frame (15) via barb control fibers (585) that temporarily hold the barb struts (260) with respect to the backing elements (450) by connecting or interfacing between the opening feature of the backing arm and the barb feature of the barb strut (260). The barb struts (260) are release by applying tension via the operator to the control fibers (585) that extend to the proximal end (115) of delivery catheter located outside of the patient's body thereby releasing the barb struts (260) and placing the barb tips (255) to the outside (350) of the waist (10) stent frame (15) during barb activation as shown in FIG. 22B.

Figure 23A:
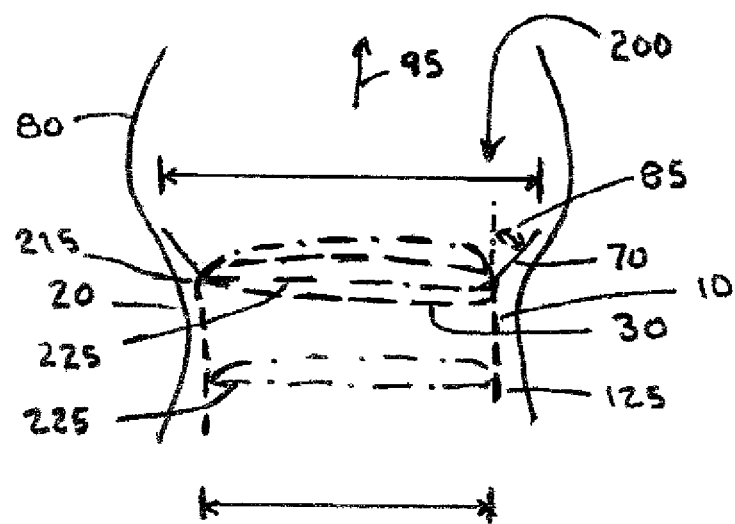
FIG. 23A is a perspective view of a frame waist for a first component or support frame having a limiting cable to limit the perimeter of the waist from further expansion.
Figure 23B:
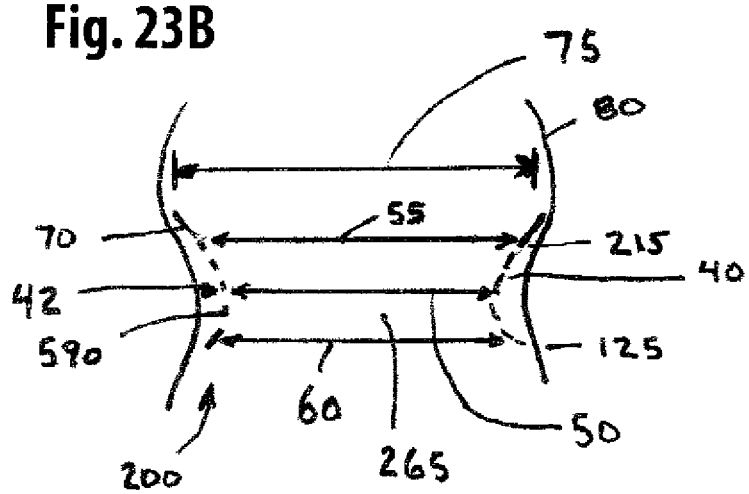
FIG. 23B is a perspective view of a frame waist of a first component having a concave region that forms a geometrical shape that can be used as a locking member for locking onto a second component or valve frame; the concave region also assists in providing a geometrical shape that fits the shape of the native valve annulus and holds onto the native valve annulus.

FIG. 23A shows a cylindrically-shaped waist (10) for the first component (200); the waist (10) being positioned adjacent the mitral annulus (20); the waist (10) can alternately be a portion of a single member stent-valve (5) as described in earlier embodiments. The upper bulb (70) is attached to the upstream end of the waist; the upper bulb (70) extends outwards to a larger upper bulb diameter (75) than the inlet waist diameter (55) as the upper bulb extends into the LA (80) at an upper bulb angle with respect to the waist of 45 degrees (range 20 to 90 degrees). One or more limiting cables (210) are attached to the waist, the limiting cables (210) extend around the perimeter (30) of the waist (10) and prevent the waist (10) from expansion to a larger perimeter than the perimeter of the limiting cables (225). As shown, one limiting cable (225) is located at the upstream end of the waist (10) near the waist inlet end (215) and one is located at the downstream end of the waist near the waist outlet end (125). The limiting cables (225) can be formed from polymeric or metal material and can be either a monofilament or multifilament strand. The limiting cable (225) is attached to the stent frame (15) via welding, brazing, adhesive bonding, swaging, or other attachment methods used in the medical device industry. The limiting cable (225) is described also in earlier embodiments found in the present patent application. FIG. 23B shows the waist (10) of the first component (200) having a curved shape or curved waist (40). The waist central diameter (50) is 3 mm (range 2-10 mm) smaller than the waist inlet diameter (55) at the upstream end (215) or the waist outlet diameter (60) at the downstream end (125) of the waist (10). The curved waist (40) shape for the first component (200) can provide a concave region (42) or hump which extend into the central lumen (265) space that would allow a groove or concave region (42) of a second component (190) to lock into position with respect to the first component (200) and would prevent the second component (190) from migrating upstream (95) toward the LA (80) or downstream toward the LV with respect to the first component (200).

Figure 24A:
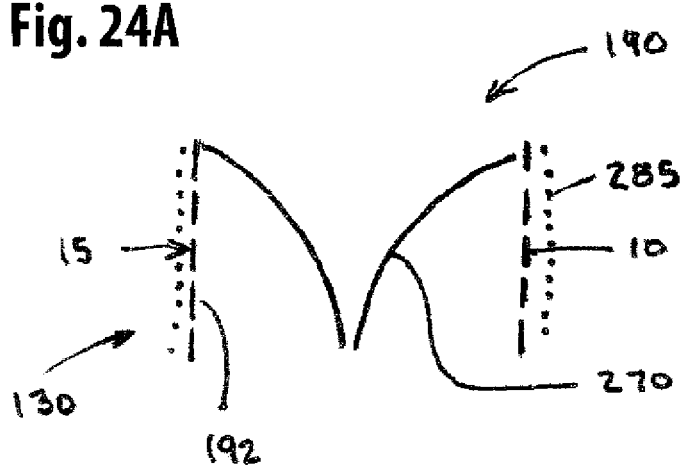
FIG. 24A is a plan view of a second component stent valve or valve frame that contains replacement leaflets.
Figure 24B:
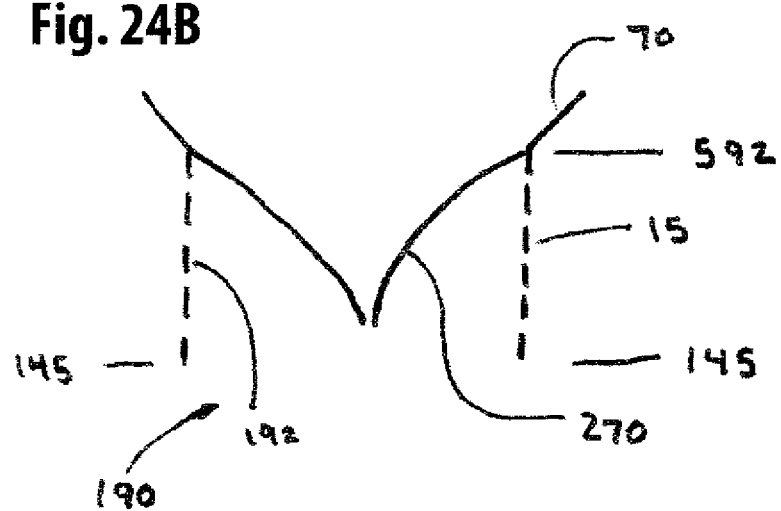
FIG. 24B is a plan view of a second component stent valve or valve frame that contains replacement leaflets; an upper bulb attached at the inlet end assists in axial placement of the second component and assists in providing a seal with a first component to prevent blood leakage between components.
Figure 24C:
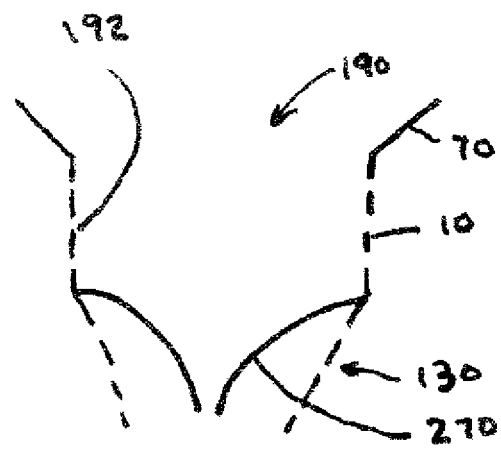
FIG. 24C is a plan view of a second component or valve frame containing replacement leaflets; the valve frame has a frustum shaped housing that houses the replacement leaflets.

Embodiments of the second component (190) of the two-step stent-valve system are shown in FIGS. 24A and 24B. FIG. 24A shows a stent-valve that could be used for a TAVR device or other stent-valve device application but instead is being applied as a second component (190) of a two-step mitral valve system. The second component (190) stent-valve has a valve frame (192) structure that contains replacement valve leaflets (270) attached to the frame (15) via crown-shaped attachments as described in earlier embodiments. The leaflet material and attachment of the leaflets to the valve frame (192) are as described in other embodiments of the present patent application. The stent-valve could have a BE stent-valve frame (192) that is formed from a BE material such as stainless steel or it can have a SE stent-valve frame (192) that is formed from Nitinol, for example. The stent valve of the second component (190) can have a cylindrically-shaped frame (15) as shown in FIG. 24A; the stent-valve can have an upper bulb (70) extend outwards into the LA (80) as shown in FIG. 24B; the stent-valve can have a frustum-shaped housing (130) that holds the replacement valve leaflets as shown in FIG. 24C. The frustum-shaped housing (130) provides an advantage over a cylindrically shaped housing (130) in that it does not impinge upon the LVOT blood flow area; the replacement leaflets (270) can be formed with a frustum shape as described in earlier embodiments of the frustum housing (130) thereby reducing the amount of force on the leaflet free edge when the leaflets are closed during systole.

Figure 24D:
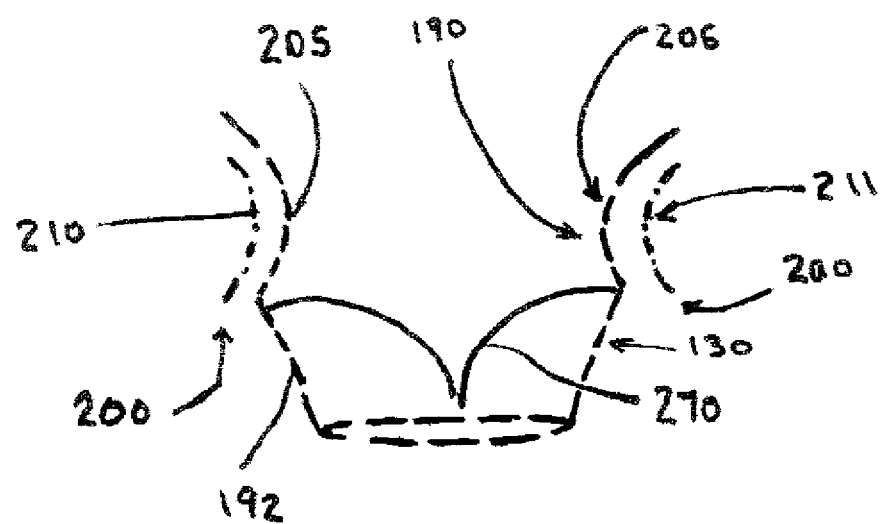
FIG. 24D is a sectional view of a dual member stent valve having a support frame having a concave waist and a valve frame located in the inside lumen of the support frame; the valve frame also having a concave waist that locks geometrically with the concave waist of the support frame.

The second component waist (205) of the second component (190) can have a second component concave region (206) that matches the curved shape of the first component concave region (211) of the first component waist (210) as shown in FIG. 24D. The second component waist (205) of the second component (190) can be delivered to a location within the mitral valve apparatus such that upon expansion of the second component (190) on the inside of the first component (200), the second component curved waist (205) tends to self-adjust itself such that the second component concave region (206) is located adjacent to the first component concave region (211). The second component concave region (206) will lock with respect to the first component concave region (211) thereby preventing migration of the second component (190) with respect to the first component (200). The first component concave region (211) is a locking region that is able to form a geometrical or locking fit with the second component concave region (206). Other locking region geometries are contemplated; the locking regions have a geometry that is distinguished from neighboring regions of the frame (15) adjacent to the locking region for the first component (200) or the second component (190).

FIG. 24E shows an embodiment of the dual member stent-valve (195) of the present invention having both the first component (200) and second component (190). The first component or support frame (200) was implanted initially within the lumen of the native mitral heart valve. The first component (200) has a SE stent frame (15) that was delivered via a delivery sheath (105) to a location adjacent to the mitral annulus (20) without affecting the native mitral valve function. An upper bulb (70) was extending outwards in the LA (80) to help position the frame (15) such that the waist extended across the annulus (20) and the upper bulb (70) was located in the LA. The profile of the first component or support frame (200) was very low due to the lack of replacement leaflets (270); hence the first component (200) was easily delivered by crossing the atrial septum. The first component (200) was allowed to expand out into contact with the mitral annulus (20) or other native mitral valve tissue without affecting movement of native mitral valve leaflets and not affecting their valvular function prior to activating the barbs (25) via a torus balloon (35) which is attached to the first component (200) as described in earlier embodiments. The torus balloon (35) allows blood to pass through the first component (200) and hence there is no shear forces or pressure forces that act to change the position of the first component (200). The torus balloon (35) can be inflated with saline such that leakage of inflation fluid is not of concern; detachment of the torus balloon (35) from the delivery catheter is easy since the inflation fluid is allowed to leak out of the torus balloon (35) as it is implanted. If the position of the first component (200) was not acceptable to the operator, it would have been withdrawn into the delivery sheath (105) via recapture struts (100) prior to activation of the barbs (25). The first component (200) has a limiting cable (225) around the perimeter (30) of the waist (10) to ensure that the second component (190) can be expanded into it and obtain a good frictional or geometrical fit.

Once the first component or support frame (200) has been delivered, a SE second component (190) is delivered into the open central lumen (265) provided by the first component (200). The second component waist (205) has a curved waist (40) with a second component concave region (206) that matches the first component concave region (211) of the first component (200) thereby locking the first component (200) with the second component (190). A covering on the first component concave region (211) and the second component concave region (206) assist in preventing leakage of blood from between the first component (200) and the second component (190). The second component (190) is released within the open central lumen (265) of the first component (200) and makes contact long a continuous perimeter with the first component (200) in the locking region or the concave regions such that blood flow is not allowed to leak between the first component (200) and the second component (190). The second component (190) can have a cylindrical housing (130) for the replacement leaflets (270) or the downstream end (145) of the housing (130) can be smaller in diameter than the housing inlet end (592) to ensure that the LVOT is not impeded.

The second component (190) can alternately be formed with a BE frame (15) and can be delivered via a cylindrical dilation balloon (588) or an expandable mechanical devices that can enlarge to form a larger configuration that would expand out a BE stent-valve. The BE second component (190) can have a second component concave region (206) that fits the first component concave region (211) of the first component (200). The BE second component (190) can be expanded under large inflation pressures or expansion forces such that the BE stent frame (15) of the second component (190) is deformed plastically around the limiting cable (225) of the first component (200) to cause a frictional and geometrical fit with the first component (200).

Figure 26A:
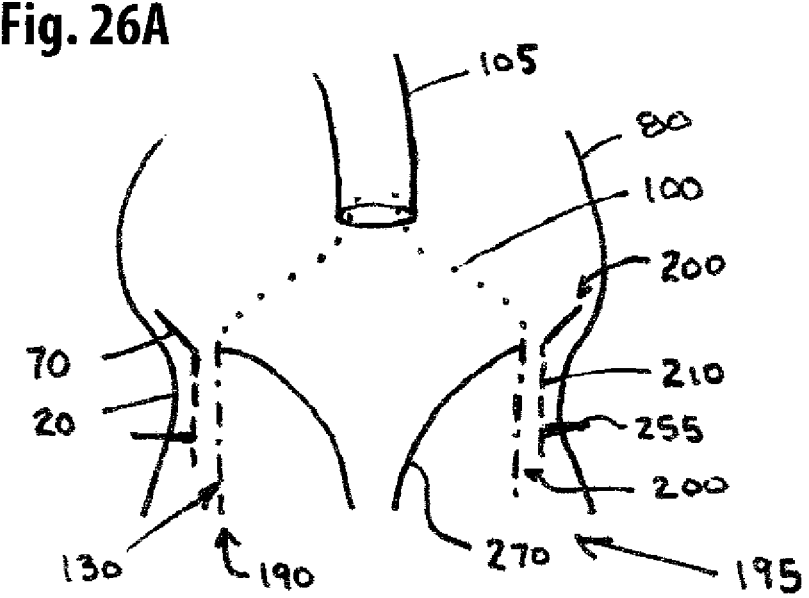
FIG. 26A is a sectional view of self-expanding second component being placed within the open central lumen of a first component or support frame; recapture struts are still attached to the valve frame of the second component.
Figure 26B:
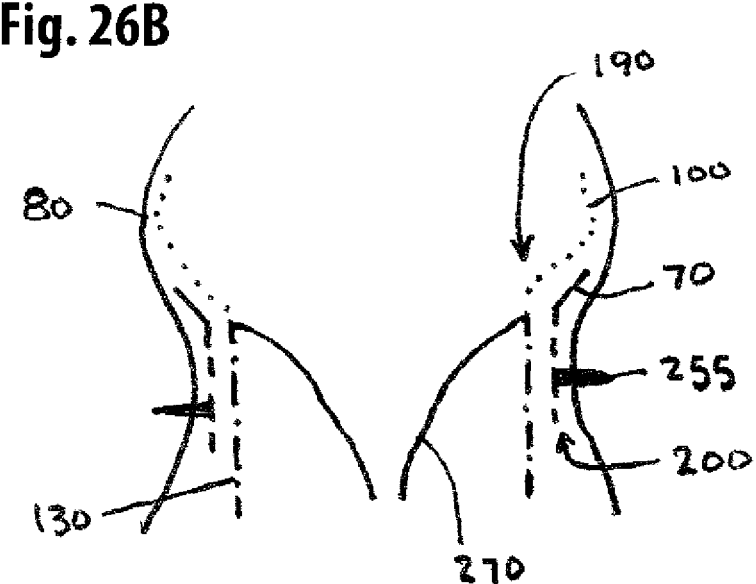
FIG. 26B is a sectional view of self-expanding second component that has been placed within the open central lumen of a first component or support frame and had its recapture struts released.

The BE stent-valve frame (15) can be delivered such that the stent frame (15) of the second component (190) of the dual member stent-valve is positioned adjacent the waist (10) of the first component (200) as shown in FIG. 25. A cylindrically-shaped dilation balloon (588) located on the luminal side (345) of the stent-valve frame (15) can apply an outward frame expansion force (405) to the frame (15) of the BE second component (190) stent valve into intimate contact with the waist (10) of the first component (200). The dilation balloon can also help to further apply an outward radial force (228) onto the barbs (25) to force the barb tips (255) outwards further into the annulus (20) or tissues of the heart valve. The limiting cables (210) located along a frame perimeter (375) of the first component (200) act to prevent over-expansion of the second component (190) to a diameter that could stretch the mitral annulus (20) potential causing injury to the patient. The limiting cables (210) also provide limit to the frame perimeter (375) that the first component (200) can attain thereby allowing the second component (190) to expand with a maximal frame outward force (65) that ensures maximal frictional contact between the second component (190) and the first component (200) thereby reducing the liklihood of migration of the second component (190) with respect to the first component (200), without the risk of over-expansion of the first component (200). The limiting cable of the first component (200) also allows the second component (190) to be expanded and deformed (by a dilation balloon, for example) such that the second component (190) forms a narrow waist (10) region adjacent to the limiting cable of the first component (200) such that the second component waist (205) of the second component (190) has an hour-glass shape that fits via a geometrical lock with the first component (200). Geometrically shaped waist (10) regions for the first and second component (190) can also help to ensure that undesirable axial movement of the second component (190) are prevented For the embodiment where the second component (190) has a SE stent-valve frame, the SE second component (190) is delivered via an external delivery sheath (105) that holds the second component (190) into a non-expanded configuration and delivers the second component (190) to a location adjacent the native mitral apparatus such that the frame waist (10) of the second component (190) is located adjacent the frame waist (10) of the first component (200) as shown in FIGS. 26A and 26B. Recapture struts (100) can be attached to the waist (10) or upper bulb (70) of the second component (190) (see FIG. 26A) to allow the second component (190) to be retrieved or repositioned as described in earlier embodiment presented in the present patent application. The second component (190) is released from the external sheath and expands outward into contact with the first component (200) as shown in FIG. 26B. Frictional forces hold the second component (190) from migration with respect to the first component (200); geometrically shaped waist (10) regions or curved waist (40) regions for the first component (200) and second component (190) also assist in preventing migration of the second component (190). Release of a SE stent-valve is provided by a pushing member contained within the delivery sheath (105) as is known in the industry for delivery of SE stented devices.

The replacement leaflet (270) for the present invention can be formed from tissues taken from animal pericardium, xenograft heart valve, allograft heart valve, or other tissue or collagen materials. Alternately, the replacement leaflets (270) can be formed from a thin layer of polymeric material such an expanded polytetrafluoroethylene (ePTFE), Dacron film, polymeric woven, braided, or knitted material. Often a polymeric material that is exposed to continued stress will tend to creep, therefore many of the polymeric films and some of the tissue or collagen materials used for valve leaflets will need to be supported by fibers or thin films made from stronger materials that will not creep under stress. Such stronger support fibers and films include Dacron fibers, thin multifilament metal fibers, thin metal films such as Nitinol films and other materials of similarly high tensile strength and low creep; such films and fibers can have diameters and thickness of 0.001 inches (range 0.0003-0.002 inches) and can be very flexible.

Figure 27A:
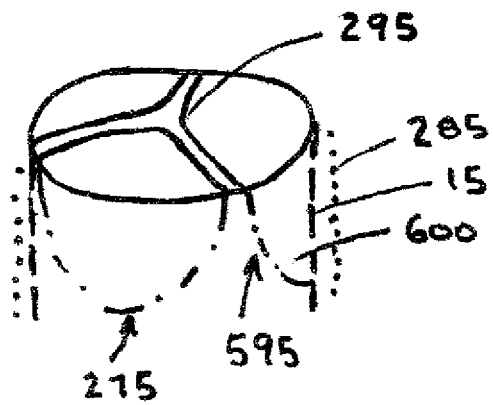
FIG. 27A is a perspective view of the semi lunar leaflets showing the crown-shaped attachment to the wall structure of the frame.
Figure 27B:
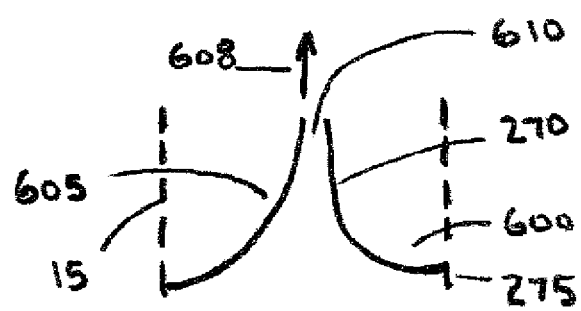
FIG. 27B is a plan view of valve leaflets showing pockets that are created as the leaflets form leaflet coaptation.
Figure 27C:
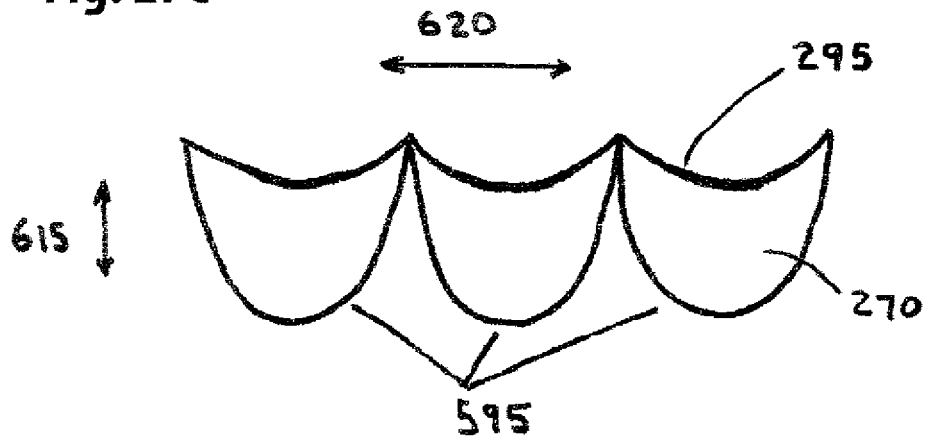
FIG. 27C is a plan view of valve leaflets splayed out showing the crown-shaped attached edge.

The semi-lunar valve leaflets of the present invention are attached to the wall of a cylindrical stent frame in a crown-shape attachment (595) path as shown in FIG. 27A. The free edge (295) of the valve leaflet comes into direct contact with a neighboring leaflet and a portion of the valve leaflet coapts with the neighboring leaflet. A leaflet pocket (600) is formed in the leaflet between the leaflet downstream surface (605) and the stent frame (15) as shown in FIG. 27B. Downstream (608) flow of blood through this valve is shown in an upward direction with blood flow leaving through the free edges (295). The leaflet pocket changes shape as the leaflet moves from an open configuration with leaflets positioned adjacent or near the wall of the stent frame (15) to a closed configuration as shown in FIGS. 27A and 27B. The leaflet pocket allows the leaflets to coapt over a coaptation surface (610) during systole when the leaflets are closed and neighboring leaflet surfaces near the free edges (270) contact each other for an axial distance of 3 mm (range 1-6 mm) forming leaflet coaptation; blood flow via a directed flow and via a recirculation pattern over the coaptation surface of the leaflets during diastole ensures that thrombus does not develop on the surfaces of the leaflets. The leaflets flex via extension in both the leaflet axial direction (615) and the circumferential direction (620) (see FIG. 27C) as they move from an open position as shown in FIG. 27C to a closed position.

The leaflet support fibers extending circumferentially can provide the required circumferential strength with minimal strain of less than 10%; axial support fibers provide more flexing and strain (i.e., 15%) to form the valve leaflet pockets and assist in leaflet coaptation. Leaflet support fibers can be attached to the leaflets to allow leaflet expansion to occur in a controlled manner, also support fibers can provide a location by which the leaflets can be attached to the stent frame (15) of the present invention, further support fibers strengthen the free edge of the leaflets to prevent the free edge from encountering irreversible stretching. An embodiment for three semi-lunar leaflets that are found as replacement leaflets (270) in the present stent-valve assembly is shown in a splayed-out manner in FIG. 27D. The crown-shaped leaflet attachment (275) path for three leaflets is shown; the crown shaped path is intended to be attached to the stent frame; the semi-lunar valve can be formed with two or four leaflets, instead of three, for example, without deviating from the present invention.

Figure 28A:
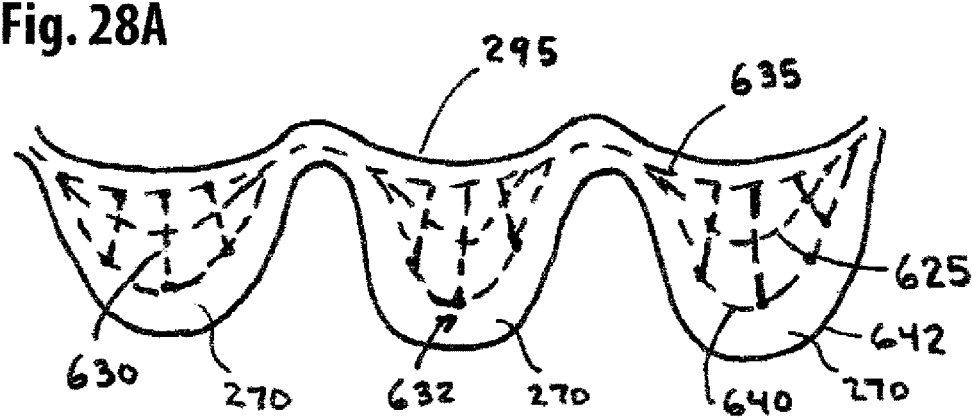
FIG. 28A is a plan view of valve leaflets showing the presence of axial and circumferential fibers attached to the leaflet surface to provide strength, control the leaflet compliance, and provide fibers to attach the leaflets to the frame.
Figure 28B:
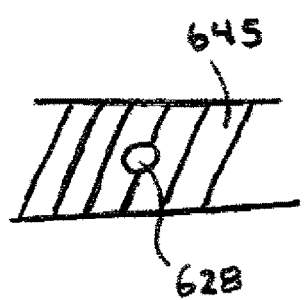
FIG. 28B is a sectional view through the thickness of a leaflet showing a fiber embedded within a polymer film.
Figure 28D:
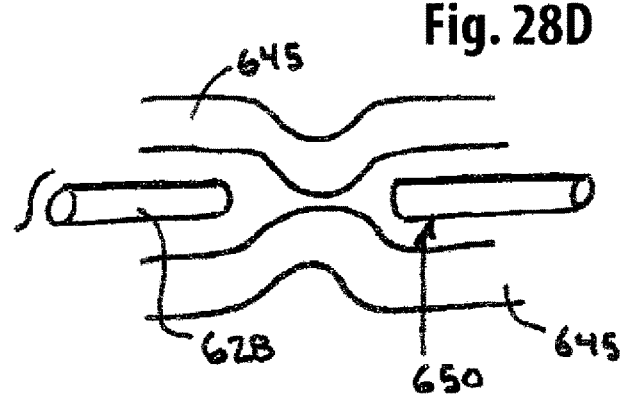
FIG. 28D is a perspective view of semilunar leaflets formed with axial fibers and circumferential fibers being attached to a frame of a stent valve.

One embodiment for the semi-lunar replacement leaflets (270) of the present invention is shown in FIG. 28A. The leaflets are formed from a polymeric film that is formed via either a film casting process, an extrusion process, or other film forming process. In this embodiment fibers (628) formed from Dacron, Nitinol, or stainless steel, for example, are embedded within the polymer matrix of the leaflet polymeric film, such as polyurethane, for example, as shown in FIG. 28A and 28B. The fiber can also be attached to collagen matrix material or tissue surfaces used to form the leaflets, the fibers can also be attached to tissue valve leaflets via adhesives, sutures, or other bonding methods. The fibers include circumferentially oriented fibers (625) and axially oriented fibers (630). A free-edge fiber (635) can extend along or near the free edges (295) of the leaflets in a circumferential direction; an attachment-edge fiber (640) can extend along the attached edge (642) of the leaflets in a circumferential direction. One or more axial fibers can extend from the free-edge fiber to the attachment-edge fiber; axial fibers can be attached to free-edge fibers or attachment-edge fibers at fiber attachment sites (632) via brazing, soldering, welding, adhesives, swaging, thermal bonding, solvent bonding, knotting, or other bonding methods. The circumferentially oriented fibers and axially oriented fibers can be embedded within the polyurethane, collagen, or tissue matrix; the polymer or tissue matrix can be solvent cast or thermally cast around the fibers as shown in FIG. 28B forming a polymeric film (645) that can be used as a valve replacement leaflet. Alternately, two separate films of polyurethane or tissue matrix can be placed onto each side of the fibers and heated to thermally bond the two film layers together or bonded together via adhesives, solvent bonding, or other bonding method thereby forming a sandwiched fiber (650) as shown in FIG. 28D; the sandwiched fiber film is used as a replacement leaflet material.

Figure 28C:
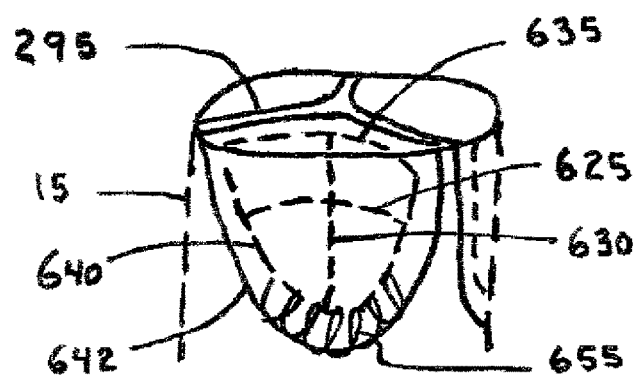
FIG. 28C is a sectional view through the thickness of a leaflet showing a fiber embedded or sandwiched between two polymer films.

The polymer or tissue matrix and fiber composite leaflets can then be attached to the stent frame (15) via a variety of methods. Sutures (655), for example can be used to sew the attachment-edge fiber to the stent frame (15) as shown in FIG. 28C. Alternately, the polymer used as the leaflet film can be used also as a covering (285) for the stent frame; the leaflet can be joined to the stent frame (15) via polymer to polymer bonding methods which include thermal bonding, solvent bonding, adhesive bonding, and other forms of bonding. The leaflet can also be contiguous with the covering (285) that is attached to the stent-valve frame.

Figure 29A:
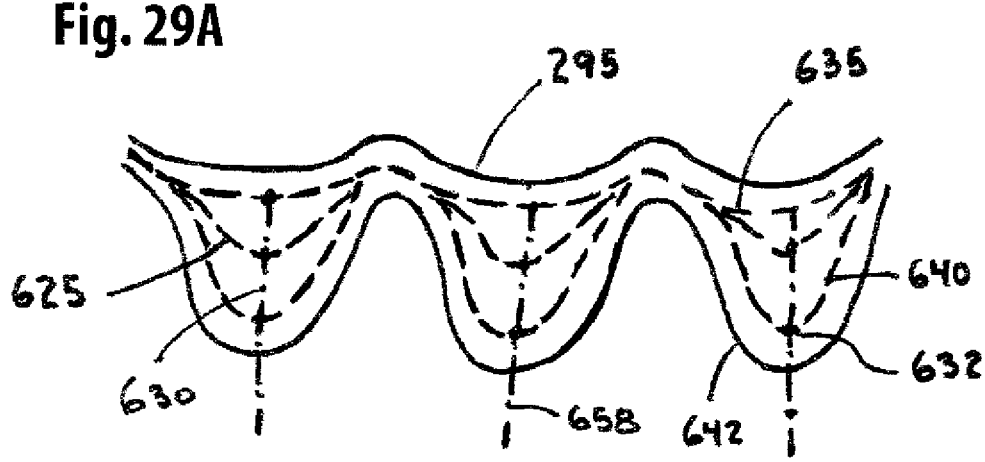
FIG. 29A is a plan view of a valve leaflets showing the presence of axial and circumferential fibers that extend within or are attached to the leaflets and have fiber extensions that allow attachment to the frame of the stent valve.
Figure 29B:
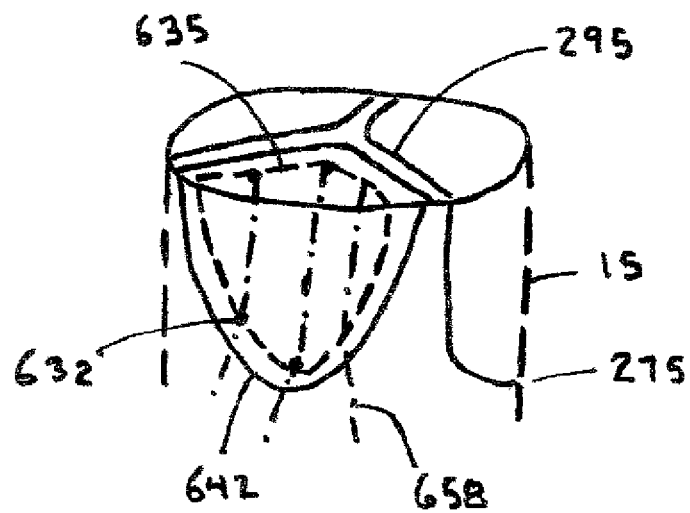
FIG. 29B is a perspective view of valve leaflets being attached to a frame via fiber extension that are embedded or attached to the leaflets.

Another embodiment for attaching the polymer and fiber composite leaflets to the stent frame (15) is shown in FIGS. 29A and 29B. In this embodiment the axial fibers are allowed to extend beyond the attached-edge fiber as shown in FIG. 29A. The axial fiber extensions can then be attached directly to the stent frame (15) via brazing, welding, swaging, adhesive bonding or other bonding methods available. The axial fibers can alternately be formed to be contiguous with the stent frame.

Figure 30:
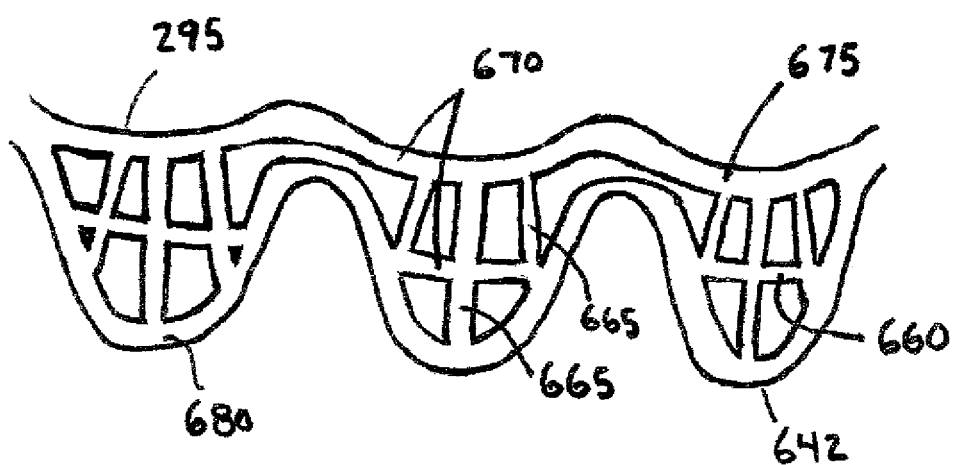
FIG. 30 is a plan view of valve leaflets having a thin film of a metal embedded within or attached to the surface of the leaflets to provide strength, compliance control, and a means for attachment.

A thin film (660) of Nitinol or other metal can be cut via laser, electric discharge method (EDM) or other methods to form a leaflet frame as shown in FIG. 30. The leaflet frame can have axial members (665) and circumferential members (670); the circumferential members can extend along the free edge forming free-edge members and along the attached edge forming attached-edge members; axial members can extend from the free-edge members to the attached-edge members. The leaflet frame can be embedded within a polymer matrix as described earlier for the fiber supported leaflet, alternately the leaflet frame can be sandwiched between to polymer films via thermal, solvent, adhesive, other bonding method used to bond two films together. The leaflet frame can be attached to the stent frame (15) via sutures, adhesive bonding, thermal bonding, welding, brazing, soldering, or other methods. Alternately, the leaflet frame can be contiguously formed along with the stent frame.

The invention claimed is:

1. A method for transcatheter delivery of an implantable device to native tissues of a heart valve, said method comprising;
    A. delivering a support frame in an unexpanded configuration within a catheter to the native tissues of the heart valve, said support frame having a torus balloon attached along a support frame perimeter, said torus balloon having an open central region,
    B. releasing at least a portion of said support frame from said catheter into an expanded configuration, said support frame being configured to contact the native tissues without having axial forces directed onto said support frame from blood flow of the heart valve through said open central region, wherein said open central region is configured to provide passage for unrestricted blood flow though said open central region with said torus balloon in an uninflated configuration,
    C. inflating said torus balloon to an inflated configuration, said torus balloon providing contact and an outward force to a plurality of barbs attached along said support frame perimeter causing said plurality of barbs to extend from an inactive configuration having said plurality of barbs located in an inside luminal region of said support frame to an active configuration having said plurality of barbs located outside of said support frame, said open central region configured to provide passage for unrestricted blood flow axially through said open central region during inflation of said torus balloon to said inflated configuration,
    D. whereby said plurality of barbs are configured to extend into the native tissues of the heart valve.

2. The method of claim 1 wherein said support frame is configured to be placed upstream of native valve leaflets of the heart valve thereby not affecting function of the native valve leaflets of the heart valve during implantation of said support frame.

3. The method of claim 1 wherein said plurality of barbs have said inactive configuration with said support frame in said expanded configuration prior to inflation of said torus balloon.

4. The method of claim 1 further comprising the step of positioning said support frame adjacent the native tissues of the heart valve prior to inflation of said torus balloon and with said barbs in said inactive configuration.

5. The method of claim 1 further comprising the step of recapturing said support frame back into said catheter following release of said portion of said support frame and prior to inflation of said torus balloon.

6. The method of claim 1 further comprising the step of detaching said torus balloon from an inflation tubing configured for inflating said torus balloon, said detaching step following inflation of said torus balloon and activation of said plurality of barbs.

7. The method of claim 6 further comprising the step of providing an open balloon inflation port on said torus balloon for drainage of inflation medium out of said torus balloon.

8. The method of claim 6 further comprising the step of retaining inflation medium within said torus balloon via a valve located within said torus balloon.

9. The method of claim 1 wherein said torus balloon is attached to said support frame and is configured to be implanted along with said support frame.

10. The method of claim 1 further comprising the step of removing said torus balloon from said support frame, said torus balloon not being configured for implantation along with said support frame.

11. The method of claim 1 wherein said support frame has a locking region, said locking region being located along said support frame perimeter and having a geometrical shape that distinguishes said locking region from neighboring regions of said support frame adjacent to said locking region in an axial direction.

12. The method of claim 1 wherein said implanted device further comprises an expandable valve frame and said method further comprising the steps;
  A. placing said expandable valve frame via a delivery sheath within said inside luminal region of said support frame, said valve frame having replacement leaflets attached to said valve frame, said replacement leaflets configured to direct the blood flow of the heart valve within said valve frame in a downstream direction,
  B. expanding said valve frame within said support frame such that said valve frame does not move axially with respect to said support frame.

13. A method of catheter delivery of a device to a heart valve and attaching said device to native tissues of a heart valve for implantation within the heart valve, said method comprising;
  A. placing a support frame contained within a catheter in an unexpanded configuration within the native tissues of the heart valve, said support frame having a torus balloon attached along a support frame perimeter in an uninflated configuration, said support frame having a plurality of barbs attached along said support frame perimeter,
  B. releasing said support frame into contact with the native tissues with said torus balloon in an uninflated configuration, said torus balloon providing said support frame with an open central region configured to provide passage for blood flow through said open central region without restriction of blood flow, said plurality of barbs having an inactive configuration in an inside luminal region of said support frame,
  C. inflating said torus balloon to an inflated configuration thereby placing said torus balloon into contact with said plurality of barbs causing said plurality of barbs to extend from said inside luminal region of said support frame to an outside region of said support frame,
  D. whereby said plurality of barbs are configured to extend into the native tissues of the heart valve and attach said support frame to the native tissues of the heart valve to prevent migration of said support frame relative to the native tissues of the heart valve.

14. The method of claim 13 further comprising the step of detaching said torus balloon from an inflation tube for said torus balloon to provide said support frame to be implanted into the native tissues of the heart valve.

15. The method of claim 13 wherein said device further comprises an expandable valve frame and said method further comprising the steps;
  A. placing said expandable valve frame within said inside luminal region of said support frame, said valve frame having replacement leaflets attached to said valve frame,
  B. expanding said valve frame within said support frame such that said valve frame locks with said support frame and said valve frame does not move axially with respect to said support frame.

16. The method of claim 13 wherein said open central region is configured to provide passage for unrestricted blood flow axially through said open central region during inflation of said torus balloon.

17. A method for placing a device delivered by a catheter within a native heart valve comprising the steps;
  A. providing a support frame, said support frame being expandable from a smaller diameter to a larger diameter, said support frame having barbs attached along a support frame perimeter, said support frame having a balloon attached to said support frame perimeter,
  B. expanding said support frame within the native heart valve while maintaining said barbs in an inactive configuration within an inside luminal region of said support frame, said balloon being in an uninflated configuration,
  C. inflating said balloon to an inflated configuration to affect an activation of said barbs, activation of said barbs placing said barbs outside of said support frame, said barbs configured to extend into the native heart valve tissue,
  D. wherein said inside luminal region of said support frame is configured to provide passage for blood flow through said inside luminal region preferably without restriction of the blood flow with said balloon in said inflated configuration.

18. The method of claim 17 further comprising the steps of;
  A. placing a valve frame within an inside luminal region of said support frame, said valve frame having replacement leaflets attached to said valve frame,
  B. expanding said valve frame within said support frame such that said valve frame contacts said support frame and said valve frame does not move axially with respect to said support frame.

* * * * *